(12) United States Patent
Murphy et al.

(10) Patent No.: US 12,082,566 B2
(45) Date of Patent: Sep. 10, 2024

(54) RODENT ANIMALS EXPRESSING HUMAN CR1

(71) Applicant: Regeneron Pharmaceuticals, Inc., Tarrytown, NY (US)

(72) Inventors: Andrew J. Murphy, Croton-on-Hudson, NY (US); Lynn MacDonald, Harrison, NY (US); Cagan Gurer, Chappaqua, NY (US); Karolina A. Meagher, Yorktown Heights, NY (US); Vera Voronina, Sleepy Hollow, NY (US); Brinda Prasad, Long Island City, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 46 days.

(21) Appl. No.: 17/490,449

(22) Filed: Sep. 30, 2021

(65) Prior Publication Data

US 2022/0104469 A1 Apr. 7, 2022

Related U.S. Application Data

(60) Provisional application No. 63/086,167, filed on Oct. 1, 2020.

(51) Int. Cl.
*A01K 67/0278* (2024.01)
*A61K 49/00* (2006.01)
*C07K 14/705* (2006.01)
*C12N 15/85* (2006.01)

(52) U.S. Cl.
CPC ...... *A01K 67/0278* (2013.01); *A61K 49/0008* (2013.01); *C07K 14/70596* (2013.01); *C12N 15/8509* (2013.01); *A01K 2207/15* (2013.01); *A01K 2217/052* (2013.01); *A01K 2227/105* (2013.01); *A01K 2267/03* (2013.01); *C12N 2015/8527* (2013.01)

(58) Field of Classification Search
CPC . A01K 67/0278; C07K 14/472; C07K 14/705
See application file for complete search history.

(56) References Cited

U.S. PATENT DOCUMENTS

2018/0243450 A1* 8/2018 Devalaraja-Narashimha ............. C07K 16/18

FOREIGN PATENT DOCUMENTS

| WO | 2005/005479 A1 | 1/2005 |
| WO | 2012/037370 A1 | 3/2012 |
| WO | 2018/157027 A1 | 8/2018 |

OTHER PUBLICATIONS

CR1 expression in The Human Protein Atlas (Year: 2023).*
NCBI Gene ID: 1378 (Year: 2020).*
Salzberg et al (Open questions: How many genes do we have? BMC Biology, vol. 16, 2018 (Year: 2018).*
Repik et al (A transgenic mouse model for studying the clearance of blood-borne pathogens via human complement receptor 1 (CR1). Clinical and Experimental Immunology, 2005, in IDS dated Jan. 27, 2022 (Year: 2005).*
B6.Cg-Tg(Gata1-CR1)1Rwf/J mouse line available from Jackson Labs (Year: 2023).*
Jackson et al (A novel mouse model expressing human forms for complement receptors CR1 and CR2. BMC Genetics, vol. 21, Sep. 9, 2020, in IDS dated Jan. 27, 2022). (Year: 2020).*
Macdonald et al (Precise and in situ genetic humanization of 6 Mb of mouse immunoglobulin genes. PNAs, vol. 111, Apr. 2014) (Year: 2014).*
Douglas et al (Complement receptor 2 polymorphisms associated with systemic lupus erythematosus modulate alternative splicing. Genes & Immunity, Apr. 2009) (Year: 2009).*
Zhao et al (Complement receptor 1 genetic variants contribute to the susceptibility to gastric cancer in Chinese population. J Cancer, Apr. 2015). (Year: 2015).*
Jackson H.M. et al., "A Novel Mouse Model Expressing Human Forms for Complement Receptors CR1 and CR2", BMC Genetics 21:101 (Sep. 9, 2020).
Repik A. et al., "A Transgenic Mouse Model for Studying the Clearance of Blood-Borne Pathogens Via Human Complement Receptor 1 (CR1)", Clinical and Experimental Immunology 140(2):230-240 (Mar. 11, 2005).
Anonymous, "Tg(Gata1-CR1) 1 Rwf Transgene Detail MGI Mouse (MGI:5140563)", Retrieved from the Internet: URL:http://www.informatics.jax.org/allele/MGI:5140563 (May 1, 2005).
International Search Report and Written Opinion dated Jan. 21, 2022 received in International Application No. PCT/US2021/052931.

* cited by examiner

*Primary Examiner* — Valarie E Bertoglio
*Assistant Examiner* — Matasha Dhar
(74) *Attorney, Agent, or Firm* — Scully, Scott, Murphy & Presser, P.C.; Trisha Agrawal

(57) ABSTRACT

Disclosed herein are genetically modified rodent animals comprising in their genome a nucleic acid which comprises a nucleotide sequence encoding a human CR1 polypeptide, wherein the rodent animals display a human-like expression of the human CR1 polypeptide. Also disclosed herein are isolated rodent cells including rodent embryonic stem cells, and rodent tissues. Further disclosed are nucleic acid vectors and methods for making the genetically modified rodent animals, as well as methods of using such genetically modified rodent animals for screening and testing candidate compounds.

9 Claims, 26 Drawing Sheets
(23 of 26 Drawing Sheet(s) Filed in Color)
Specification includes a Sequence Listing.

↑ Elevated compared to 75/25 WT    ↓ Decreased compared to 75/25 WT

| Sample ID | | GLUC_3 mg/dL | UN mg/dL | CREA_2 mg/dL | TP g/dL | ALBP g/dL | ALT U/L | AST U/L | LIP U/L | TBIL_2 mg/dL | MG mg/dL | IP mg/dL | UA mg/dL | CHOL_2 mg/dL | TRIG_2 mg/dL | DBILI mg/dL | DHDL mg/dL | ALP_3c U/L |
|---|---|---|---|---|---|---|---|---|---|---|---|---|---|---|---|---|---|---|
| 6143HO 7239WT | | ↓207 | ↑162 | ↑0.51 | 3.7 | 0.8 | ↑60 | 155 | ↑75 | 0 | 4.5 | 9.4 | 2.9 | 72 | ↓27 | 7.9 | 39.5 | 225 |
| 75/25WT | | 350 | 23 | 0.23 | 5.7 | 1.4 | 33 | 98 | 43 | 0.1 | 3.5 | 11.7 | 4.5 | 90 | 107 | 7.3 | 55 | 91 |
| 6143HO 7239HO | | ↓50 | ↑50 | ↑0.21 | 5.6 | 1.5 | ↑325 | ↑443 | 41 | 0.1 | 2.7 | 9.5 | 4.6 | 112 | 123 | 10.5 | 71.2 | 194 |

Glucose → Urea Nitrogen → Creatinine → ALT → AST → Lipase → Triglycerides

Kidney    Liver

ONLY n=1 per group

- Glucose: acute stress (heart attack, stroke, chronic renal failure, trauma)
- Urea Nitrogen: kidney dysfunction/congestive heart failure, recent heart attack
- Creatinine: congestive heart failure/glomerulonephritis
- ALT: liver damage
- AST: liver damage, myocardial infarction
- Lipase: pancreas damage, acute pancreatitis and obstruction of pancreatic duct
- Triglycerides: type I diabetes, nephrosis, liver obstruction, lipid metabolism and endocrine disorders

FIG. 3E

RODENT ANIMALS EXPRESSING HUMAN CR1

CROSS REFERENCE TO RELATED APPLICATIONS

This application claims the benefit of priority from U.S. Provisional Application No. 63/086,167, filed Oct. 1, 2020, the entire contents of which is incorporated herein by reference.

INCORPORATION BY REFERENCE OF SEQUENCE LISTING

The Sequence Listing in the ASCII text file, named as 38224_10747US01_Sequence Listing of 42 KB, created on Sep. 29, 2021 and submitted to the United States Patent and Trademark Office via EFS-Web, is incorporated herein by reference.

BACKGROUND

During preclinical drug development stage, candidate agents are typically studied based on their efficacy, toxicity, and other pharmacokinetic and pharmacodynamics properties. Candidate agents, such as antibodies, typically target a human antigen as the end goal of investigation is to develop a human therapy. The ability to sequester the complement pathway provides a significant advantage to candidate therapeutic agents. The complement pathway is part of the innate immune response and assists humoral immune responses in the recruitment of marcrophage and phagocytes to the antigenic site. Activation of the complement pathway results in cytokine release and the opsonization of the antibody-bound antigen by phagocytes. During development of therapeutic agents that are aimed at activation of complement pathway and innate immune response in order to combat human disease, a model non-human animal system that would allow studies into the mechanisms of action and/or therapeutic potential of the agent would be invaluable.

SUMMARY

In one aspect, disclosed herein is a genetically modified rodent animal comprising in its genome a nucleic acid which comprises a nucleotide sequence encoding a human CR1 polypeptide, wherein the rodent animal displays a human-like expression of the human CR1 polypeptide.

In some embodiments, the nucleotide sequence encoding the human CR1 polypeptide is a genomic DNA sequence. In some embodiments, the nucleotide sequence encoding the human CR1 polypeptide is a cDNA sequence.

In some embodiments, the nucleic acid is inserted between the rodent Cr2 gene locus and the rodent Cr1like (Cr1l) gene locus in the rodent genome. In some embodiments, the nucleic acid is inserted into the rodent genome via random integration, e.g., into an X chromosome of the rodent (such as a locus other than the rodent Gata-1 gene locus).

In some embodiments, the nucleic acid comprises a 5' regulatory region of a human CR1 gene, operably linked to the nucleotide sequence encoding the human CR1 polypeptide. In some embodiments, the 5' regulatory region comprises the promoter region of the human CR1 gene. In some embodiments, the 5' regulatory region comprises the 5' untranslated region (5' UTR) of the human CR1 gene, operably linked to the nucleotide sequence encoding the human CR1 polypeptide. In some embodiments, the 5' regulatory region comprises the promoter and the 5' untranslated region (5' UTR) of the human CR1 gene.

In some embodiments, the nucleic acid comprises a 3' regulatory region of a human CR1 gene, operably linked to the nucleotide sequence encoding the human CR1 polypeptide. In some embodiments, the 3' regulatory region comprises the 3' UTR of the human CR1 gene, operably linked to the nucleotide sequence encoding the human CR1 polypeptide. In some embodiments, the 3' regulatory region comprises the 3' UTR and an additional sequence downsteam of the 3' UTR of the human CR1 gene.

In some embodiments, the nucleic acid comprises a human genomic DNA sequence, which comprises the human CR1 coding sequence from ATG to STOP, with the 5' and 3' untranslated regions (UTRs) and intervening introns, as well as a 5' upstream sequence of at least 4000 bp directly upstream of the 5' UTR and a sequence of at least 150 bp directly downstream of the 3' UTR; and in some such embodiments, the nucleic acid is inserted between the rodent Cr2 gene locus and the rodent Cr1l gene locus.

In some embodiments, the nucleic acid comprises a 5' regulatory region of a heterologous gene (i.e., a gene that is not human CR1), operably linked to the nucleotide sequence encoding the human CR1 polypeptide. In some embodiments, the 5' regulatory region is a 5' regulatory region of a rodent Gata-1 gene. In some embodiments, the 5' regulatory region comprises the promoter region of a rodent Gata-1 gene. In some embodiments, the 5' regulatory region comprises a genomic sequence of at least 14 Kb immediately upstream of the ATG codon of a rodent Gata-1 gene.

In some embodiments, the nucleic acid comprises a 3' regulatory region of a heterologous gene (i.e., a gene that is not human CR1), operably linked to the nucleotide sequence encoding the human CR1 polypeptide. In some embodiments, the 3' regulatory region comprises the 3' UTR of a heterologous gene, e.g., the 3' UTR (including the polyadenylation sequence) of a human beta-1 globin gene.

In some embodiments, the nucleic acid comprises a human CR1 coding sequence (ATG to STOP) (e.g., in the form of cDNA), operably linked to, at the 5', a nucleotide sequence of at least 14 Kb directly upstream of ATG of a rodent Gata-1 gene (including the promoter of the rodent Gata1 gene), and at the 3', a 3' UTR sequence containing the poly(A) signal from a human beta globin gene followed by a nucleotide sequence of at least 1.5 Kb directly downstream of the STOP codon of the rodent Gata-1 gene; and in some such embodiments, the nucleic acid is integrated into an X-chromosome of the rodent (e.g., at a locus other than the rodent Gata-1 gene locus).

In some embodiments, a genetically modified rodent animal may comprise multiple nucleic acids in its genome, each comprising a nucleotide sequence encoding a human CR1 polypeptide. In some embodiments, a genetically modified rodent animal comprises in its genome a first nucleic acid comprising a first nucleotide sequence encoding a human CR1 polypeptide, wherein the first nucleic acid is inserted between the rodent Cr2 gene locus and the Cr1l gene locus in the rodent genome; and a second nucleic acid comprising a second nucleotide sequence encoding a human CR1 polypeptide in operable linkage to a 5' regulatory region of a rodent Gata-1 gene, and a 3' regulatory region comprising a polyA signal of a human beta-1 globin gene, wherein the second nucleic acid is integrated into an X chromosome of the rodent genome.

In some embodiments, a genetically modified rodent animal further comprises in its genome a replacement of a rodent C3 gene sequence at an endogenous rodent C3 locus with a human C3 gene sequence to form a modified C3 gene, wherein the rodent C3 gene sequence comprises an exon of the endogenous rodent C3 gene and the human C3 gene sequence comprises exon 2 through exon 41, or exon 1 through exon 41, of the human C3 gene. In some embodiments, expression of the modified C3 gene is under control of a human C3 promoter, or under control of rodent regulatory elements at the endogenous rodent C3 locus.

In some embodiments, a rodent animal is a male. In some embodiments, a rodent animal is a female.

In some embodiments, a rodent animal is heterozygous for a nucleic acid exogenously introduced and integrated in the genome. In some embodiments, a rodent animal is homozygous for a nucleic acid exogenously introduced and integrated in the genome.

In some embodiments, a rodent animal is a mouse. In some embodiments, a rodent animal is a rat.

In some embodiments, a rodent animal expresses a human CR1 polypeptide on red blood cells. In some embodiments, a rodent animal expresses e human CR1 polypeptide on neutrophils, e.g., netrophils from the blood, spleen or liver. In some embodiments, a rodent animal expresses a human CR1 polypeptide on red blood cells and neutrophils. In some embodiments, a rodent animal expresses a human CR1 polypeptide on red blood cells and/or neutrophils, and additionally on one or more of macrophages, monocytes, or circulating dendritic cells (cDCs).

In another aspect, provided herein is a cell or tissue isolated from a rodent animal described herein, wherein the genome of the cell or tissue comprises the nucleic acid comprising a nucleotide sequence encoding a human CR1 polypeptide. In some embodiments, the rodent cell is a rodent egg.

In a further aspect, provided herein is a rodent (such as mouse or rat) embryonic stem (ES) cell, comprising in its genome a nucleic acid which comprises a nucleotide sequence encoding a human CR1 polypeptide, as described herein. In some embodiments, the nucleic acid is inserted between the rodent Cr2 gene locus and the rodent Cr1l gene locus in the rodent genome of the ES cell, and comprises a human genomic DNA sequence, which includess the human CR1 coding sequence from ATG to STOP, with the 5' and 3' untranslated regions (UTRs) and intervening introns, as well as a 5' upstream sequence of at least 4000 bp directly upstream of the 5' UTR and a sequence of at least 150 bp directly downstream of the 3' UTR. In some embodiments, the nucleic acid is inserted into the genome (e.g., an X chromosome) of the rodent ES cell and comprises a 5' regulatory region of a rodent Gata-1 gene, and a 3' regulatory region of a human beta-1 globin gene, operably linked to the nucleotide sequence encoding the human CR1 polypeptide.

In still another aspect, disclosed herein is a method of making a genetically modified rodent animal, comprising inserting a nucleic acid into the genome of a rodent ES cell, wherein the nucleic acid comprises a nucleotide sequence encoding a human CR1 polypeptide as described herein; and making a genetically modified rodent animal using a rodent ES cell obtained. Also disclosed herein is a method of making a genetically modified rodent ES cell, comprising inserting a nucleic acid into the genome of a rodent ES cell, wherein the nucleic acid comprises a nucleotide sequence encoding a human CR1 polypeptide as described herein.

In some embodiments, the nucleotide sequence encoding the human CR1 polypeptide is a genomic DNA sequence. In some embodiments, the nucleotide sequence encoding the human CR1 polypeptide is a cDNA sequence.

In some embodiments, the nucleic acid is inserted between the rodent Cr2 gene locus and the rodent Cr1like (Cr1l) gene locus in the rodent genome. In some embodiments, the nucleic acid is inserted into the rodent genome via random integration, e.g., into an X chromosome of the rodent (such as a locus other than the rodent Gata-1 gene locus).

In some embodiments, the nucleic acid comprises a 5' regulatory region of a human CR1 gene, operably linked to the nucleotide sequence encoding the human CR1 polypeptide. In some embodiments, the 5' regulatory region comprises the promoter region of the human CR1 gene. In some embodiments, the 5' regulatory region comprises the 5' untranslated region (5' UTR) of the human CR1 gene, operably linked to the nucleotide sequence encoding the human CR1 polypeptide. In some embodiments, the 5' regulatory region comprises the promoter and the 5' untranslated region (5' UTR) of the human CR1 gene.

In some embodiments, the nucleic acid comprises a 3' regulatory region of a human CR1 gene, operably linked to the nucleotide sequence encoding the human CR1 polypeptide. In some embodiments, the 3' regulatory region comprises the 3' UTR of the human CR1 gene, operably linked to the nucleotide sequence encoding the human CR1 polypeptide. In some embodiments, the 3' regulatory region comprises the 3' UTR and an additional sequence downsteam of the 3' UTR of the human CR1 gene.

In some embodiments, the nucleic acid comprises a human genomic DNA sequence, which comprises the human CR1 coding sequence from ATG to STOP, with the 5' and 3' untranslated regions (UTRs) and intervening introns, as well as a 5' upstream sequence of at least 4000 bp directly upstream of the 5' UTR and a sequence of at least 150 bp directly downstream of the 3' UTR; and in some such embodiments, the nucleic acid is inserted between the rodent Cr2 gene locus and the rodent Cr1l gene locus.

In some embodiments, the nucleic acid comprises a 5' regulatory region of a heterologous gene (i.e., a gene that is not human CR1), operably linked to the nucleotide sequence encoding the human CR1 polypeptide. In some embodiments, the 5' regulatory region is a 5' regulatory region of a rodent Gata-1 gene. In some embodiments, the 5' regulatory region comprises the promoter region of a rodent Gata-1 gene. In some embodiments, the 5' regulatory region comprises a genomic sequence of at least 14 Kb immediately upstream of the ATG codon of a rodent Gata-1 gene.

In some embodiments, the nucleic acid comprises a 3' regulatory region of a heterologous gene (i.e., a gene that is not human CR1), operably linked to the nucleotide sequence encoding the human CR1 polypeptide. In some embodiments, the 3' regulatory region comprises the 3' UTR of a heterologous gene, e.g., the 3' UTR (including the polyadenylation sequence) of a human beta-1 globin gene.

In some embodiments, the nucleic acid comprises a human CR1 coding sequence (ATG to STOP) (e.g., in the form of cDNA), operably linked to, at the 5', a nucleotide sequence of at least 14 Kb directly upstream of ATG of a rodent Gata-1 gene (including the promoter of the rodent Gata1 gene), and at the 3', a 3' UTR sequence containing the poly(A) signal from a human beta globin gene followed by a nucleotide sequence of at least 1.5 Kb directly downstream of the STOP codon of the rodent Gata-1 gene; and in some such embodiments, the nucleic acid is integrated into an X-chromosome of the rodent (e.g., at a locus other than the rodent Gata-1 gene locus).

In another aspect, disclosed herein is a targeting vector, comprising a nucleic acid which comprises a nucleotide sequence encoding a human CR1 polypeptide, flanked by rodent nucleotide sequences for targeted insertion of the nucleic acid between the rodent Cr2 gene locus and the rodent Cr1l gene locus in the rodent genome.

In still another aspect, disclosed herein is a nucleic acid vector, comprising a nucleic acid which comprises nucleotide sequence encoding a human CR1 polypeptide in operable linkage to a 5' regulatory region of a rodent Gata-1 gene.

In a further aspect, disclosed herein is a method of assessing the pharmacokinetic properties of a compound targeting human CR1 or another component of the human complement system (such as human C3), the method comprising administering a candidate compound to a genetically modified rodent animal disclosed herein; and performing an assay to determine one or more pharmacokinetic properties of the compound.

BRIEF DESCRIPTION OF THE DRAWINGS

The file of this patent or patent application contains at least one drawing executed in color. Copies of this patent with color drawing(s) will be provided by the Patent and Trademark Office upon request and payment of the necessary fee.

FIG. 3E shows exacerbated liver injury, but ameliorated kidney injury in C3 HumIn CR1 HumIn (6149HO 7239HO) mice as compared to C3 HumIn (6149HO 7239WT) mice.

DETAILED DESCRIPTION

Figure 1A:
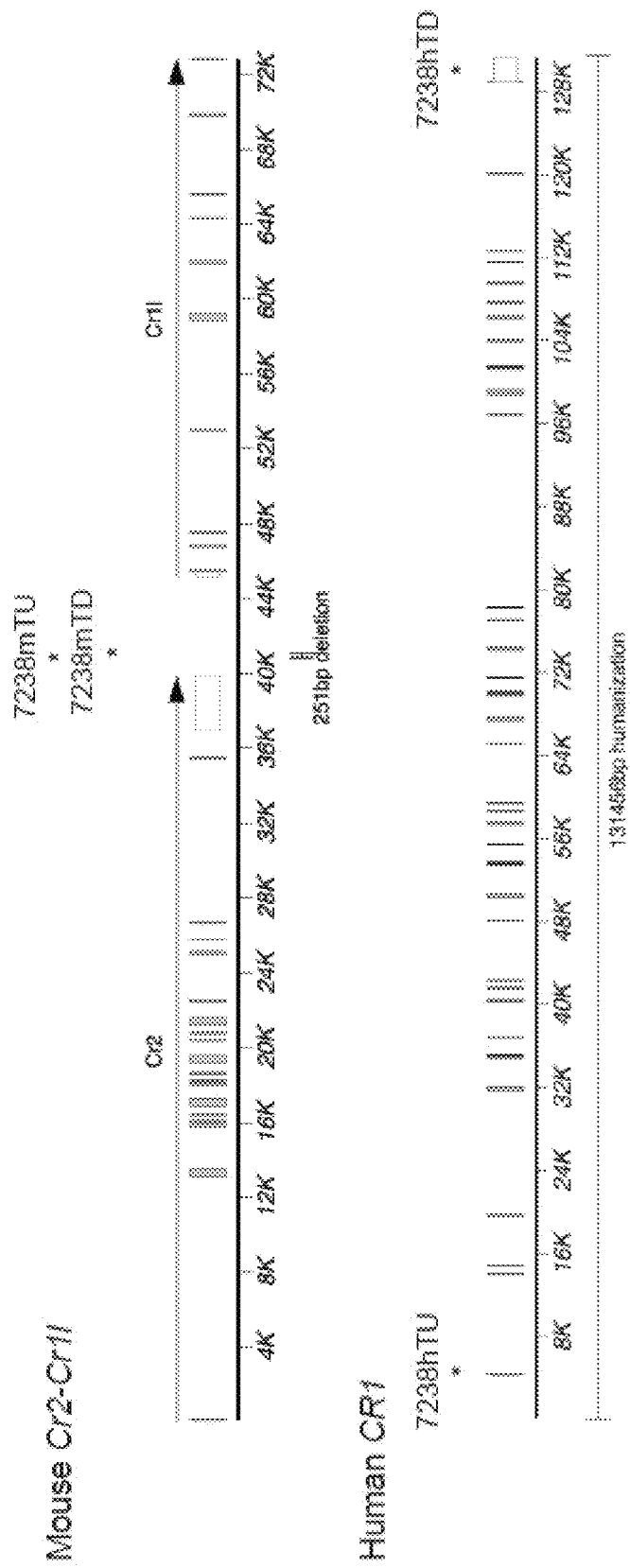
FIG. 1A depicts a mouse genomic fragment comprising the Cr2-Cr1l gene loci and a human genomic fragment comprising the CR1 gene, with exons shown as by vertical bars. The location of the mouse sequence of 251 bp to be replaced by a human CR1 genomic sequence is indicated. The locations for the primer sets and probes designed for detecting deletion of mouse sequences (loss of allele or LOA) (7238 mTU and 7238 mTD) and insertion of the human sequences (gain-of-allele or GOA) (7238 hTU and 7238 hTD) are also indicated.
Figure 1B:
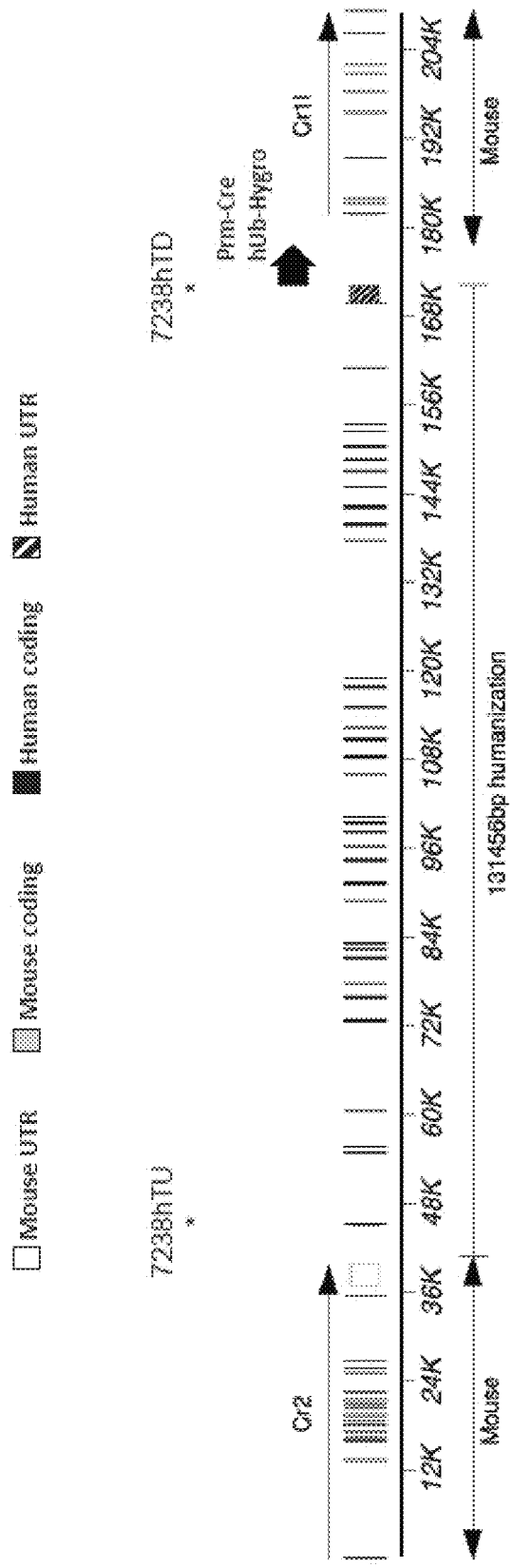
FIGS. 1B-1C depict the 7238 and 7239 alleles, respectively, having a human CR1 genomic sequence inserted between mouse Cr2 and Cr1l genes by replacing a mouse genomic sequence of 251 bp. The locations for the primer sets and probes designed for detecting insertion of the human sequences (gain-of-allele or GOA) (7238 hTU and 7238 hTD) are also indicated. The 7239 allele results from deletion of the self-deleting hygromycin resistance cassette in the 7238 allele. Following cassette deletion, a scar containing a loxP site remains.
Figure 1C:
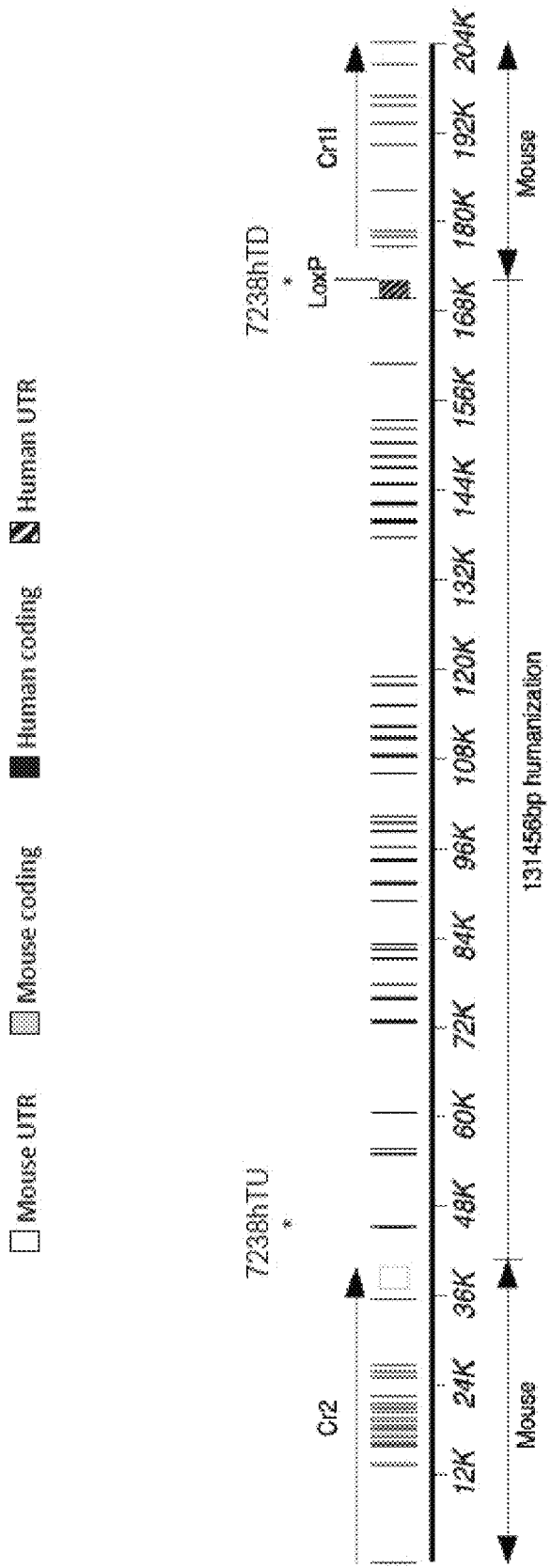

Disclosed herein are rodents (such as mice and rats) genetically modified to comprise a nucleic acid comprising a human CR1 coding sequence integrated in the genome and to display a human-like expression of the human CR1 protein. Also disclosed herein are isolated rodent tissues and cells whose genome comprises a nucleic acid encoding a human CR1 protein. Further disclosed herein are vectors and methods for making a genetically modified rodent animal which displays a human-like expression of the human CR1 protein, as well as methods of using the genetically modified rodent animal for screening candidate compounds that target human CR1 or another component of the human complement system (such as hman C3). The various aspects and embodiments are further described below.

Human CR1/CD35

Human CR1 (also known as CD35) is encoded by human CR1 gene and is known to recognize complement coated microbial surface and functions in particle adherence. CR1 functions in immune complex (IC) trafficking/immune-adherence clearance by binding to C3b/C4b opsonized IC to human erythrocytes and transports them to the liver and spleen for uptake and degradation by phagocytes.

Human CR1 is a type 1 transmembrane protein of about 200 kDa, which in addition to its presence on erythrocytes, is found on neutrophils, monocytes/macrophages, B cells, some T cells, follicular DC, glomerular podocytes, eosinophils, mast cells, and NK cells. The number of CR1 molecules decreases with aging of erythrocytes.

In addition to CR1, a CR2 gene also exisits in human and encodes CR2/CD21 protein.

Mice do not have a functional or structural homolog of human CR1, but do have CR1-like genes; for example, a Crry gene (aka Cr1like or Cr1l) which encodes a Cr1l protein which shares 10% sequence identity with human CR1; and a Cr2 gene which encodes a Cr2 protein which shares 17% sequence identity with human CR1. Mouse Cr2 and Cr1like proteins are expressed on B cells, follicular DCs, peritoneal macrophages, activated granulocytes, and platelets, but not on erythrocytes. Similar to mice, rat also has Cr1l and Cr2 genes.

Human CR1 gene is located on human chromosome 1, and an exemplary genomic sequence can be found under NCBI Gene ID number 1378. Mouse Cr1l and Cr2 genes are located on mouse chromosome 1, and exemplary genomic sequences of these genes can be found under NCBI Gene ID number 12946 and 12902, respectively. Rat Cr1l and Cr2 genes are located on rat chromosome 13, and exemplary genomic sequences of these genes can be found under NCBI Gene ID number 54243 and 289395, respectively. Examples of RefSeq mRNA IDs and Protein IDs are listed below in Table 1.

TABLE 1

| Gene Name | RefSeq mRNA IDs | UniProt ID or NCBI Protein ID | NCBI Gene ID |
|---|---|---|---|
| Human CR1 | NM_000573.4 (SEQ ID NO: 1) | P17927 (SEQ ID NO: 2) | 1378 |

TABLE 1-continued

| Gene Name | RefSeq mRNA IDs | UniProt ID or NCBI Protein ID | NCBI Gene ID |
| --- | --- | --- | --- |
| Mouse Cr2 | NM_007758.3 | Q9DC83 | 12902 |
| Mouse Cr1l | NM_013499.2 | Q64735 | 12946 |
| Rat Cr2 | NM_001105989.2 | NP_001099459.2 | 289395 |
| Rat Cr1l | NM_001005265.1 | NP_001005265.1 | 54243 |

Genetically Modified Animals Expressing Human CR1

In one aspect, provided herein is a genetically modified rodent animal (e.g., mouse or rat) comprising an exogenously introduced nucleic acid, integrated in the rodent genome (i.e., rodent germline) and directing expression of a human CR1 polypeptide in the rodent in a human-like manner The exogenously introduced nucleic acid comprises a nucleotide sequence encoding a human CR1 polypeptide. In some embodiments, the nucleic acid also comprises a 5' regulatory region, and/or and a 3' regulatory region, operably linked to the nucleotide sequence encoding a human CR1 polypeptide. In some embodiments, the transgene includes additional elements, such as a reporter gene and a selectable marker gene, among others.

The term "operably linkage" includes a linkage of nucleic acid elements in a functional relationship. A nucleic acid sequence is "operably linked" when it is placed into a functional relationship with another nucleic acid sequence. For instance, a promoter, or a 5' regulatory region containing a promoter, is considered as operably linked to a coding sequence if the promoter or the 5' regulatory region effects the transcription of the coding sequence.

The terms "5' regulatory region" and "3' regulatory region" as used herein include regulatory elements found in the 5' upstream region and the 3' downstream region of a gene. The term "regulatory elements" includes transcriptional regulatory sequences, which include both 5' transcriptional regulatory sequences such as promoter, enhancer, and suppressor elements, and 3' transcriptional regulatory sequences such as a transcriptional termination sequence. The term "regulatory elements" also includes regulatory sequences in the 5' untranslated region (5' UTR) and the 3' UTR that may affect the efficiency of transcription and the stability of transcript, as well the initiation of translation.
Nucleotide sequence encoding a human CR1 polypeptide In some embodiments, a nucleic acid that is integrated in the rodent genome comprises a nucleotide sequence encoding a human CR1 polypeptide which comprises an amino acid sequence substantially identical to SEQ ID NO: 2.

In referring to a given amino acid sequence as being "substantially identical" to a reference sequence, it includes embodiments where the given amino acid sequence is at last 90% identical, at least 95% identical, at least 98% identical, at least 98.5% identical, at least 99% identical, or at least 99.5% identical, to a reference sequence; for example, a given amino acid sequence differs from a reference sequence by 1, 2, 3, 4, or 5 amino acids, or differs by not more than 5, 4, 3, 2, or 1 amino acid(s). The differences may represent polymorphism that naturally exists for a given molecule.

In some embodiments, the human CR1 polypeptide comprises an amino acid sequence that is at least 90%, at least 95%, at least 98%, or at least 99% identical to SEQ ID NO: 2. In some embodiments, the human CR1 polypeptide comprises the amino acid sequence of SEQ ID NO: 2.

In some embodiments, a nucleotide sequence encoding a human CR1 polypeptide is a genomic DNA sequence (i.e., having intronic sequences). In some embodiments, a nucleotide sequence encoding a human CR1 polypeptide is a cDNA sequence (i.e., without intronic sequences). Examples of nucleotide sequencse encoding a human CR1 polypeptide suitable for use herein include the genomic DNA sequence as set forth in GenBank under NCBI Gene ID 1378 and the cDNA sequence as set forth in GenBank under Accession No. NM_000573.4 (SEQ ID NO: 1).

In some embodiments, a nucleotide sequence encoding a human CR1 polypeptide, either a genomic DNA or a cDNA sequence, comprises a coding sequence beginning from the ATG start codon and ending at the Stop codon of a human CR1 gene.
5' and 3' Regulatory Regions In some embodiments, a nucleic acid that is exogenously introduced and integrated in the rodent geome can additionally include a 5' regulatory region, operably linked to the nucleotide sequence encoding a human CR1 polypeptide that is included in the nucleic acid.

In some embodiments, a nucleic acid that is exogenously introduced and integrated in the rodent geome includes a 5' regulatory region, operably linked to the human CR1 coding nucleotide sequence.

In some embodiments, a 5' regulatory region includes a 5' untranslated region (5' UTR). In some embodiments, the 5' regulatory region includes a 5' UTR of a human CR1 gene, such as the 5' UTR of the human CR1 gene as set forth in GenBank under NCBI Gene ID 1378 or Accession No. NM_000573.4. In some embodiments, the 5' regulatory region includes a 5' UTR of a heterologous gene, i.e., a gene that is not a human CR1 gene, such as, e.g., a rodent Gata-1 gene.

In some embodiments, a 5' regulatory region comprises transcription regulatory elements such as promoter and/or enhancer. In some embodiments, a 5' regulatory region comprises a nucleotide sequence (including the promoter region) upstream of the 5' UTR of a human CR1 gene, such as the human CR1 gene as set forth in GenBank under NCBI Gene ID 1378. In some embodiments, the 5' regulatory region comprises comprises a nucleotide sequence that is immediately upstream of the 5' UTR of a human CR1 gene and is of at least 1000 bp, at least 1500 bp, at least 2000 bp, at least 2500 bp, at least 3000 bp, at least 3500 bp, at least 4000 bp, at least 4500 bp, at least 5000 bp, at least 6000 bp, at least 7000 bp, at least 8000 bp, at least 9000 bp, at least 10,000 bp, or longer (e.g., up to 15 Kb-20 Kb), in length. In some embodiments, the 5' regulatory region comprises a nucleotide sequence that is immediately upstream of the 5' UTR of a human CR1 gene and is of at least 4000 bp in length, such as the 4233 bp sequence (SEQ ID NO: 3) upstream of the 5' UTR of the human CR1 gene as set forth in GenBank under NCBI Gene ID 1378.

In some embodiments, a 5' regulatory region comprises a nucleotide sequence (including the promoter region) upstream of the 5' UTR of a heterologous gene, i.e., a gene different from a human CR1 gene. In some embodiments, the heterologous gene is a rodent gene that displays expression in red blood cells, e.g., a rodent Gata-1 gene. In some embodiments, a 5' regulatory region comprises a sequence upstream of the 5' UTR of a rodent (e.g., mouse) Gata-1 gene that includes the promoter of the rodent Gata-1 gene. In some embodiments, for example, a 5' regulatory region comprises a sequence immediately upstream of the 5' UTR of a rodent (e.g., mouse) Gata-1 gene that is at least 7000 bp, at least 8000 bp, at least 9000 bp, at least 10,000 bp, at least 11,000 bp, at least 12,000 bp, at least 13,000 bp, at least 14,000 bp, or longer, in length. In some embodiments, a 5' regulatory region comprises a sequence upstream of the 5'

UTR of a mouse Gata-1 gene as set forth in GenBank under NCBI Gene ID 14460. In some embodiments, a 5' regulatory region comprises a sequence that is immediately upstream of the 5' UTR of the mouse Gata-1 gene as set forth in GenBank under NCBI Gene ID 14460, and that is at least 7000 bp, at least 8000 bp, at least 9000 bp, at least 10,000 bp, at least 11,000 bp, at least 12,000 bp, at least 13,000 bp, at least 14,000 bp, at least 15,000 bp, at least 16,000 bp, at least 17,000 bp, at least 18,000 bp, at least 19,000 bp, at least 20,000 bp or longer (e.g., up to 25-35 Kb), in length.

In some embodiments, a nucleic acid that is exogenously introduced and integrated in the rodent geome can additionally include a 3' regulatory region, operably linked to the nucleotide sequence encoding a human CR1 polypeptide that is included in the nucleic acid.

In some embodiments, a 3' regulatory region includes a 3' UTR. In some embodiments, a 3' regulatory region includes the 3' UTR of a human CR1 gene, such as the 3' UTR of the human CR1 gene as set forth in GenBank under NCBI Gene ID 1378 or Accession No. NM_000573.4. In some embodiments, a 3' regulatory region includes a 3' UTR of a heterologous gene, i.e., a gene that is not a human CR1 gene, such as, e.g., a human beta-1 globin gene. In some embodiments, a 3' regulatory region includes a 3' UTR sequence (containing the ployadenylation signal) of a human beta-1 globin gene as set forth in SEQ ID NO: 4.

In some embodiments, a 3' regulatory region comprises a sequence downstream of the 3' UTR of a human CR1 gene, such as the human CR1 gene as set forth in GenBank under NCBI Gene ID 1378. In some embodiments, the 3' regulatory region comprises a nucleotide sequence that is immediately upstream of the 3' UTR of a human CR1 gene and is of at least 50 bp, at least 100 bp, at least 150 bp, at least 200 bp, at least 300 bp, at least 400 bp, at least 500 bp, at least 750 bp, at least 1000 bp, or longer (e.g., up to 2500-4000 bp), in length. In some embodiments, the 3' regulatory region comprises a nucleotide sequence that is immediately downstream of the 3' UTR of a human CR1 gene and is of at least 150 bp in length, such as the 159 bp (SEQ ID NO: 41) immediately downstream of the 3' UTR of a human CR1 gene as set forth in GenBank under NCBI Gene ID 1378.

In some embodiments, a 3' regulatory region comprises a sequence downstream of the 3' UTR of a heterologous gene. In some embodiments, the heterologous gene is a rodent gene that displays expression in red blood cells, e.g., a rodent Gata-1 gene. In some embodiments, a 3' regulatory region comprises a sequence downstream of the 3' UTR of a rodent (e.g., mouse) Gata-1 gene. In some embodiments, a 3' regulatory region comprises a sequence immediately downstream of the 3' UTR of a rodent (e.g., mouse) Gata-1 gene that is at least 250 bp, at least 500 bp, at least 1000 bp, at least 1500 bp, at least 2000 bp, at least 3000 bp, or longer, in length. In some embodiments, a 3' regulatory region comprises a sequence downstream of the 3' UTR of a mouse Gata-1 gene as set forth in GenBank under NCBI Gene ID 14460. In some embodiments, a 3' regulatory region comprises a sequence that is immediately downstream of the 3' UTR of a mouse Gata-1 gene as set forth in GenBank under NCBI Gene ID 14460, and that is at least 250 bp, at least 500 bp, at least 1000 bp, at least 1500 bp, at least 2000 bp, at least 3000 bp, or longer (e.g., up to 4000-6000 bp), in length.

Embodiments of Exogenously Introduced Nucleic Acids

In some embodiments, a nucleic acid exogenously introduced and integrated in the rodent genome comprises a human genomic DNA which includes the entire human CR1 coding sequence from ATG to STOP, with the 5' and 3' untranslated regions (UTRs) and intervening introns, as well as a 5' upstream sequence of at least 4000 bp directly upstream of the 5' UTR and a sequence of at least 150 bp directly downstream of the 3' UTR. In some embodiments, the nucleic acid integrated in the rodent genome comprises a human genomic DNA which includes the entire human CR1 coding sequencec from ATG to STOP, with the 5' and 3' untranslated regions (UTRs) and intervening introns, as well as an additional sequence of 4,233 bp directly upstream of the 5' UTR and a sequence of 159 bp directly downstream of the 3' UTR.

In some embodiments, a nucleic acid exogenously introduced and integrated in the rodent genome comprises a human CR1 coding sequence (ATG to STOP) (e.g., in the form of cDNA), operably linked to, at the 5', a nucleotide sequence of at least 14 Kb directly upstream of ATG of a rodent Gata-1 gene (including the promoter of the rodent Gata1 gene), and at the 3', a 3' UTR sequence containing the poly(A) signal from a human beta globin gene followed by a nucleotide sequence of at least 1.5 Kb directly downstream of the STOP codon of the rodent Gata-1 gene.

In some embodiments, a genetically modified rodent animal (e.g., mouse or rat) comprises multiple (i.e., two or more) exogenously introduced nucleic acids integrated in the rodent genome, with each nucleic acid being any of the nucleic acids described above and encoding a human CR1 polypeptide. Such rodent animal can be made by crossing (i.e., cross-breeding) rodent animals comprising one nucleic acid integrated in the rodent genome.

Location of an Exogenously Introduced Nucleic Acid in Rodent Genome

In some embodiments, a nucleic acid is integrated to a selected site in the rodent genome. Integration into a specific site can be accomplished by utilizing a nucleic acid construct specifically designed for targeted insertion into the site. In some embodiments, a nucleic acid comprising a human CR1 coding sequence is integrated in the rodent genome between the rodent Cr2 gene locus and the rodent Cr1l gene locus; namely, at a location 3' (downstream) from the 3' UTR of the rodent Cr2 gene and 5' (upstream) to the 5' UTR of the rodent Cr1l gene. In some embodiments, the nucleic acid is integrated in the rodent genome at a location of not more than 3000 bp, not more than 2500 bp, not more than 2000 bp, not more than 1500 bp, not more than 1250 bp, or not more than 1000 bp downstream from the 3' UTR of the rodent Cr2 gene. In some embodiments, the nucleic acid is integrated in the rodent genome at about 900 bp downstream from the 3' UTR of the rodent Cr2 gene.

In some embodiments, a nucleic acid that is integrated in the rodent genome between the rodent Cr2 gene locus and the rodent Cr1l gene locus comprises a human genomic DNA which includes the entire human CR1 coding sequence from ATG to STOP, with the 5' and 3' untranslated regions (UTRs) and intervening introns, as well as a 5' upstream sequence of at least 4000 bp directly upstream of the 5' UTR and a sequence of at least 150 bp directly downstream of the 3' UTR. In some embodiments, a nucleic acid integrated in the rodent genome between the rodent Cr2 gene locus and the rodent Cr1l gene locus comprises a human genomic DNA which includes the entire human CR1 coding sequencec from ATG to STOP, with the 5' and 3' untranslated regions (UTRs) and intervening introns, as well as an additional sequence of 4,233 bp directly upstream of the 5' UTR and a sequence of 159 bp directly downstream of the 3' UTR.

In some embodiments, a nucleic acid is integrated randomly to one or more sites in the rodent genome. In cases of random integration, multiple copies of a nucleic acid may be integrated at multiple sites in the rodent genome; or alternatively, multiple copies of a nucleic acid may be integrated in tandem into one locus of the genome. In some embodiments, only one copy of a nucleic acid encoding a human CR1 polypeptide is integrated into the rodent genome. In some embodiments, a nucleic acid is integrated through random integration to an X chromosome of the rodent genome. In some embodiments, only one copy of a nucleic acid is integrated through random integration to an X chromosome of the rodent genome. In some embodiments, one copy of a nucleic acid is integrated through random integration to a locus of an X chromosome that is not the rodent Gata-1 gene locus.

In some embodiments, a nucleic acid that is randomly integrated in the rodent genome comprises a human CR1 coding sequence (ATG to STOP) (e.g., in the form of cDNA), operably linked to, at the 5', a nucleotide sequence of at least 14 Kb directly upstream of ATG of a rodent Gata-1 gene (including the rodent Gata1 promoter), and at the 3', a 3' UTR sequence containing the poly(A) signal from a human beta globin gene followed by a nucleotide sequence of at least 1.5 Kb directly downstream of the STOP codon of a rodent Gata-1 gene; in some of such embodiments, one copy of the nucleic acid encoding a human CR1 polypeptide is integrated through random integration to an X chromosome of the rodent genome, e.g., integrated to a locus that is not the rodent Gata-1 gene locus.

In some embodiments, a genetically modified rodent animal comprising a first nucleic acid comprising a first nucleotide sequence encoding a human CR1 polypeptide integrated at a specific site in the rodent genome, and a second nucleic acid comprising a second nucleotide sequence encoding a human CR1 polypeptide integrated randomly in the rodent genome. In some embodiments, a genetically modified rodent animal comprises a first nucleic acid integrated between the rodent Cr2 gene locus and the rodent Cr1l gene locus in the rodent genome, and a second nucleic acid integrated into a locus on an X chromosome in the rodent genome; in some such embodiments, the first nucleic acid comprises a human genomic DNA which includes the entire human CR1 coding sequence from ATG to STOP, with the 5' and 3' untranslated regions (UTRs) and intervening introns, as well as a 5' upstream sequence of at least 4000 bp (e.g., a sequence of 4233 bp) directly upstream of the 5' UTR and a sequence of at least 150 bp (e.g., a sequence of 159 bp) directly downstream of the 3' UTR; and the second nucleic acid comprises a human CR1 coding sequence (ATG to STOP) (e.g., in the form of cDNA), operably linked to, at the 5', a nucleotide sequence of at least 14 Kb directly upstream of ATG of a rodent Gata-1 gene (including the rodent Gata1 promoter), and at the 3', a 3' UTR sequence containing the poly(A) signal from a human beta globin gene followed by a nucleotide sequence of at least 1.5 Kb directly downstream of the STOP codon of a rodent Gata-1 gene.

Heterozygosity/Homozygosity, Gender and Strain Background

In some embodiments, a genetically modified rodent animal is heterzogous for a nucleic acid exogenously introduced and integrated in the rodent genome. In some embodiments, a genetically modified rodent animal is homozygous for a nucleic acid exogenously introduced and integrated in the rodent genome. In embodiments where a genetically modified rodent animal comprises multiple nucleic acids each comprising a nucleotide sequence encoding a human CR1 polypeptide, the rodent animal can be heterozygous or homozygous for one nucleic acid, and independently heterozygous or homozygous for another nucleic acid.

In some embodiments, the genetically modified rodent animal is a male animal. In some embodiments, the genetically modified rodent animal is a female animal.

In some embodiments, the rodent is a mouse. In some embodiments, the rodent is a mouse of a C57BL strain, for example, a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In other embodiments, the rodent is a mouse of a 129 strain, for example, a 129 strain selected from the group consisting of 129P1, 129P2, 129P3, 129X1, 129S1 (e.g., 12951/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al. (1999), *Mammalian Genome* 10:836; Auerbach et al. (2000), *Biotechniques* 29(5):1024-1028, 1030, 1032). In some embodiments, the rodent is a mouse that is a mix of an aforementioned 129 strain and an aforementioned C57BL/6 strain. In certain embodiments, the mouse is a mix (i.e., hybrid) of aforementioned 129 strains, or a mix of aforementioned C57BL strains, or a mix of a C57BL strain and a 129 strain. In certain embodiments, the mouse is a mix of a C57BL/6 strain with a 129 strain. In specific embodiments, the mouse is a VGF1 strain, also known as F1H4, which is a hybrid of C57BL/6 and 129. In other embodiments, the mouse is a BALB strain, e.g., BALB/c strain. In some embodiments, the mouse is a mix of a BALB strain and another aforementioned strain.

In some embodiments, the rodent is a rat. In certain embodiments, the rat is selected from a Wistar rat, an LEA strain, a Sprague Dawley strain, a Fischer strain, F344, F6, and Dark Agouti. In other embodiments, the rat is a mix of two or more strains selected from the group consisting of Wistar, LEA, Sprague Dawley, Fischer, F344, F6, and Dark Agouti.

Human Like Expression of Human CR1 in a Fenetically Modified Rodent Animal

Genetically modified rodent animals provided herein express human CR1 in a human-like expression pattern. By "human-like" expression pattern it is meant that the human CR1 polypeptide is expressed on cells in a rodent characteristic of the human cells which express human CR1 in human For example, human CR1 is expressed on erythrocytes and neutrophils in human, among other cells, whereas mouse Cr2 protein is not expressed on neutrophils in mouse, yet mouse Cr1like protein is expressed on all mouse cells including erythrocytes. Thus, in some embodiments, a human-like expression pattern comprises expression of a human CR1 on erythrocytes in the rodent. In some embodiments, a human-like expression pattern comprises expression of a human CR1 on neutrophils in the rodent, e.g., neutrophils found in the blood, the spleen, and/or the liver. In some emebodiments, a human-like expression pattern comprises expression of a human CR1 on erythrocytes and neutrophils e.g., neutrophils found in the blood, the spleen, and/or the liver) in the rodent. In some embodiments, a human-like expression pattern comprises expression of a human CR1 in the rodent on one or more of macrophages (such as macrophages in the blood, large peritoneal macrophages, macrophages in the spleen, and motile macrophages in the liver), monocytes (inflammatory and/or resident monocytes), and circulating dendritic cells (cDCs), in addition to erythrocytes and/or neutrophils.

Other Genetic Modifications In a Genetically Modified Rodent

In addition to comprising a nucleic acid encoding a human CR1 polypeptide Modified C3 gene integrated in the geneome, a genetically modified rodent may comprise other genetic modifications. In some embodiments, a genetically modified rodent disclosed herein also comprises in its genome, a replacement at an endogenous rodent C3 locus of a rodent gene sequence comprising an exon of a C3 gene with a nucleic acid sequence comprising at least one exon of a human C3 gene to form a modified C3 gene, as described for example in U.S. Pat. No. 9,795,121 B1 (Regeneron Pharmaceuticals, Inc.), incorporated herein in its entirety.

In some embodiments, a nucleic acid sequence comprising at least one exon of a human C3 gene comprises coding exon 1 through coding exon 41 of the human C3 gene. In some embodiment, a nucleic acid sequence comprising at least one exon of a human C3 gene comprises 5' regulatory elements and coding exon 1 through coding exon 41 of the human C3 gene. In some embodiments, a nucleic acid sequence comprising at least one exon of a human C3 gene comprises coding exon 2 through coding exon 41 of the human C3 gene.

In some embodiments, a genetically modified rodent is a mouse, whose genome comprises a replacement of a mouse C3 genomic sequence comprising 5' regulatory elements and all of the coding exons 1 through 41 of the endogenous mouse C3 gene with a human C3 genomic sequence comprising 5' regulatory elements and all of the coding exons 1 through 41 of the human C3 gene. In some embodiments, a genetically modified rodent is a mouse, whose genome comprises a replacement of a mouse C3 genomic sequence comprising coding exons 2 through 41 of the endogenous mouse C3 gene with a human C3 genomic sequence comprising coding exons 2 through 41 of the human C3 gene.

In some embodiments, a genetically modified rodent does not express an endogenous rodent C3 protein. In some embodiments, a genetically modified rodent express an endogenous rodent C5 protein.

Genetically modified rodent animals comprising a modified C3 gene encoding human C3 are prone to high rates of spontaneous death and additionally exhibit physiological, morphological, and histological symptoms which resemble complement-related nephropathies, as well as symptoms consistent with liver fibrosis, as described in U.S. Pat. No. 10,765,762 (Regeneron Pharmaceuticals, Inc.). In accordance with this disclosure, expression of a human CR1 polypeptide can ameliorate the injury to the kidney and symptoms of complement-related nephropathy, which result from human C3 being expressed from a modified C3 gene in the rodent. Complement-related nephropathy may be reflected by one or more symptoms selected from (i) one or more of glomerulonephritis, basophilic tubules, sclerotic glomeruli, dilated tubules with protein casts, mesangial matrix expansion, glomerular hypertrophy, mononuclear interstitial inflammation, (ii) C3 protein deposition in the kidney, (iii) deposition of C5b-9 membrane attack complexes in the kidney, (iv) one or more of elevated blood urea nitrogen (BUN), serum lipase, serum cystatin C, or serum non-high density lipoproteins, (v) increased urinary albumin or C5a, (vi) spontaneous death, (vii) decreased weight, decreased bone density, and/or decreased body fat, or a combination of any one of (i) to (vii). Those skilled in the art would be able to readily assess a change, if any, in a relevant parameter or symptom, and determine whether the change is statistically significant to constitute amelioration of nephropathy in the rodent as a result of human CR1 expression and in comparison to appropriate control rodents without the human CR1 expression.

Nucleic Acid Vectors and Methods of Making A Rodent Expressing Human CR1

Targeting Vector for Targeted Insertion

Rodents comprising an exogenously introduced nucleic acid which comprises a nucleotide sequence encoding a human CR1 polypeptide can be made using various methods. In some embodiments, a targeting nucleic acid construct (i.e., a targeting vector) is constructed to carry a desired nucleic acid is constructed. The term "targeting vector" as used herein refers to vectors designed to have a nucleic acid carried on the vector to be inserted into a target locus of the rodent genome.

The nucleic acid carried on a targeting vector can be any of the nucleic acids described herein above. Depending on size (e.g., whether a genomic DNA or cDNA is used), a nucleic acid can be cloned directly from cDNA sources or synthetically made. Alternatively, bacterial artificial chromosome (BAC) libraries can provide human CR1 nucleic acid sequences.

The targeting vector can include, in addition to a nucleic acid to be integrated which comprises a nucleotide sequence encoding human CR1, flanking nucleic acid sequences that are of suitable lengths and homologous to rodent sequences at a selected endogenous rodent locus (e.g., a locus between the rodent Cr2 gene locus and the rodent Cr1l gene locus) so as to be capable of mediating homologous recombination and integration of the nucleic acid that comprises a nucleotide sequence encoding human CR1 into the endogenous rodent locus. The flanking nucleic acid sequences can be 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, in length, or any value between the above-recited lengths.

In some embodiments, a targeting vector also includes a selectable marker gene (e.g., a self deleting cassette containing a selectable marker gene, as described in U.S. Pat. Nos. 8,697,851, 8,518,392 and 8,354,389, all of which are incorporated herein by reference), which can be flanked by or comprises site-specific recombination sites (e.g., loxP, Frt, etc.). The selectable marker gene can be placed on the targeting vector adjacent to the nucleic acid that comprises a nucleotide sequence encoding human CR1, to permit easy selection of transfectants.

Transgenic Vector for Random Integration

In some embodiments, a nucleic acid that comprises a nucleotide sequence encoding human CR1, can be inserted into a rodent genome using a transgenic vector designed for random integration.

A transgenic vector comprises any of the human CR1 polypeptide-encoding nucleic acids described above. In some embodiments, a transgenic vector comprises a human CR1 coding sequence (ATG to STOP) (e.g., in the form of cDNA), operably linked to, at the 5', a nucleotide sequence of at least 14 Kb directly upstream of ATG of a rodent Gata-1 gene (including the rodent Gata1 promoter), and at the 3', a 3' UTR sequence containing the poly(A) signal from a human beta globin gene followed by a nucleotide sequence of at least 1.5 Kb directly downstream of the STOP codon of a rodent Gata-1 gene.

A transgenic vector can include additional elements, such as a selectable marker gene, placed on the transgenic vector adjacent to the human CR1 nucleic acid. The selectable marker gene can be, e.g., a self deleting cassette containing a selectable marker gene, as described in U.S. Pat. Nos. 8,697,851, 8,518,392 and 8,354,389, all of which are incorporated herein by reference, which can be flanked by or comprises site-specific recombination sites (e.g., loxP, Frt, etc.).

The transgenes disclosed herein can be made using known methods. For example, a transgene can be assembled using bacterial homologous recombination and VELOCIGENE® technology (see, e.g., U.S. Pat. No. 6,586,251 and Valenzuela et al., High-throughput engineering of the mouse genome coupled with high-resolution expression analysis, 2003, *Nature Biotech.* 21(6):652-659). An example of a transgenic vector carrying a human CR1 nucleic acid is described in Example 4 hereinbelow.

Introduction of a Vector and Integration of a Human CR1 Nucleic Acid into a Rodent Genome In some embodiments, a vector carrying a desired nucleic acid to be integrated, either a targeting vector or a transgenic vector, can be introduced into rodent embryonic stem (ES) by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference) describe mouse ES cells and the VELOCIMOUSE® method for making a genetically modified mouse; and US 2014/0235933 A1, US 2014/0310828 A1, and US 2014/0309487 A1 (all of which are incorporated herein by reference) describe rat ES cells and methods for making a genetically modified rat.

ES cells having a desired nucleic acid integrated in the rodent genome can be selected. In embodiments where a targeting vector is used, ES cells having the nucleic acid integrated into a target locus are selected. In embodiments where a transgenic vector is used, ES cells having the nucleic acid integrated into the genome are selected irrespective of the site(s) where the integration occurs; in some such embodiments, one or more copies of the nucleic acid may be integrated at one or more sites; and in some such embodiments, one copy of the nucleic acid may be integrated at one site.

ES cells having a desired nucleic acid integrated in the genome are then used as donor ES cells for injection into a pre-morula stage embryo (e.g., 8-cell stage embryo) by using the VELOCIMOUSE® method (see, e.g., U.S. Pat. Nos. 7,576,259, 7,659,442, 7,294,754, and US 2008-0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the exogenous nucleic acid can be identified by genotyping of DNA isolated from tail snips using a modification of allele (MOA) assay (Valenzuela et al., supra) that detects the presence of the exogenous nucleic acid sequence.

In other embodiments, a genetically modified rodent can be made without using ES cells. For example, the genome of a non-ES cell of a rodent (e.g., a fibroblast or an induced pluripotent cell) can be modified based on conventional transformation methods (e.g., electroporation), and the modified genome of such non-ES cell can be transferred to a suitable recipient cell, e.g., an oocyte, by employing the nuclear transfer technique. The modified cell (e.g., the modified oocyte) is then gestated under suitable conditions to form an embryo. See, e.g., Han et al., "Nuclear Transfer in Mouse Oocytes and Embryos", *Methods in Enzymology* 476: 171-184 (2010), and Zhou et al., "Generation of Fertile Cloned Rats by Regulating Oocyte Activation", *Science* 302: 1179 (2003).

Crossing and Backcrossing

Genetically modified rodent animals comprising an exogenous nucleic acid encoding a human CR1 polypeptide can be crossed with other rodent animals. A manner of preparation is to generate a series of rodent animals, each containing one of the desired nucleic acids or transgenes. Such rodent animals are bred together through a series of crosses, backcrosses and selections, to ultimately generate a single rodent animal containing all desired nucleic acids, where the mammal is otherwise congenic (genetically identical) to the wild type except for the presence of the desired nucleic acids. In one embodiment, a mouse comprising an exogenous nucleic acid a human CR1-coding sequence and comprising a human C3 gene sequence is produced in this manner In another embodiment, a mouse is prepared in this manner to comprise (i) a nucleic acid comprising a nucleotide sequence encoding a human CR1 polypeptide and integrated between the mouse Cr2 gene locus and the mouse Cr1l gene locus, and (ii) a nucleic acid comprising a nucleotide sequence encoding a human CR1 polypeptide, operably linked to a mouse Gata1 promoter and integrated in an X chromosome.

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the desired nucleic acids in the proper chromosomal location. In addition, it may be necessary to cross or backcross over several generations to ultimately obtain the desired genotype.

Use of a Genetically Modified Rodent Expressing Human CR1

Genetically modified rodent animals expressing a human CR1 can be used to screening and testing candidate drugs targeting human CR1. Because CR1 is a negative regulator of the complement system, expression of human CR1 can also be useful in abrogating complement overactivation which causes unwanted kidney and liver injury in a C3 humanized rodent, thereby facilitating generation of rodent animals with fully functional human complement activity. Genetically modified rodent animals expressing a human CR1 and human C3 can also be used to screen and test candidate drugs targeting human C3 or otherwise modulating the human complement system.

In one aspect, provided herein are methods for assessing candidate compounds targeting human CR1 or another component of the human complement system (such as human C3). The method utilizes any of the genetically modified rodents (for example, mice or rats) disclosed herein. Candidate compounds can be, without limitation, small molecule chemical compounds, antibodies, proteins, inhibitory nucleic acids, or any combination thereof.

In some embodiments, the present invention provides a method of assessing the pharmacokinetic properties of a compound targeting human CR1 or another component of the human complement system (such as human C3), the method comprising the steps of administering a compound to a genetically modified rodent animal disclosed herein; and performing an assay to determine one or more pharmacokinetic properties of the compound. Pharmacokinetic properties include, but are not limited to, how an animal processes the compound into various metabolites (or detection of the presence or absence of one or more metabolites, including, but not limited to, toxic metabolites), half-life, circulating levels of compound after administration (e.g., serum concentration of compound), anti-compound response (e.g., anti-compound antibodies), compound absorption and distribution, route of administration, routes of excretion and/or clearance of the compound. In some embodiments, pharmacokinetic and pharmacodynamic properties of compounds (e.g., human CR1 modulators) are monitored in or through the use of a genetically modified rodent animal disclosed herein.

Genetically modified rodent animals disclosed herein provide an in vivo system for assessing the on-target toxicity of a compound (e.g., a compound targeting human CR1 or human C3). In some embodiments, a compound may be delivered or administered to one or more genetically modified rodent animals disclosed herein, followed by monitoring of or performing one or more assays on the animals (or cells isolated therefrom) to determine the on-target toxic effect of the compound on the animals. Exemplary on-target effects include too high of a dose, chronic activation/inactivation, and correct action in an incorrect tissue.

Genetically modified rodent animals disclosed herein provide an in vivo system for assessing the off-target toxicity of a compound (e.g., a compound targeting human CR1 or human C3). In some embodiments, a compound may be delivered or administered to one or more genetically modified rodent animals disclosed herein, followed by monitoring of or performing one or more assays on the animals (or cells isolated therefrom) to determine the off-target toxic effect of the compound on the animals. Off-target effects can occur when a compound interacts with an unintended target (e.g., cross-reactivity to a common epitope). Exemplary off-target effects include incorrect activation/inhibition of an incorrect target regardless of the tissue in which the incorrect target is found. In some embodiments, off-target effects of a compound are determined by comparing the effects of administering the compound to non-human animals of the present invention to one or more reference non-human animals.

Exemplary parameters that may be measured in rodent animals (or in and/or using cells isolated therefrom) for assessing the pharmacokinetic properties, on-target toxicity, and/or off-target toxicity of a compound include, but are not limited to, agglutination, autophagy, cell division, cell death, complement-mediated hemolysis, DNA integrity, compound-specific antibody titer, compound metabolism, gene expression arrays, metabolic activity, mitochondrial activity, oxidative stress, phagocytosis, protein biosynthesis, protein degradation, protein secretion, stress response, target tissue compound concentration, non-target tissue compound concentration, transcriptional activity and the like.

In some embodiments, rodent animals disclosed herein are used to identify a compound capable of modulating complement activation comprising administering the compound to any of the rodent animals described herein; and assaying if complement activation in the rodent is modulated, thereby identifying a compound capable of modulating complement activation. In some embodiments, a compound modulates complement activation by increasing complement activity. In some embodiments, a compound modulates complement activation by decreasing complement activity.

In some embodiments, a candidate compound is administered directly to a rodent following experimental induction of complement activation (for example, in a kidney ischemia/reperfusion model) and the effects of the compound with respect to their ability to bind human and modulate human CR1, and/or to modulate the complement system are assessed. In other embodiments, a candidate compound is contacted with serum obtained from a rodent and complement activity is assessed using any commonly used in vitro assessment technique (such as, but not limited to $CH_{50}$ assays).

The invention can be further understood by reference to the following examples, which are provided by way of illustration and are not meant to be limiting.

EXAMPLES

The following examples are put forth so as to provide those of ordinary skill in the art with a complete disclosure and description of how the compositions and/or methods claimed herein are made and evaluated, and are intended to be purely exemplary and are not intended to limit the disclosure.

Example 1. Generation of Mouse Comprising Targeted Insertion of Human CR1

Generation of mourse having targeted insertion of human CR1—A large targeting vector (LTVEC) was generated using human and mouse bacterial artificial chromosomes (BAC) DNA and VELOCIGENE® technology (see, e.g., U.S. Pat. No. 6,586,251 and Valenzuela et al. (2003) High-throughput engineering of the mouse genome couple with high-resolution expression analysis. Nat. Biotech. 21(6): 652-659, both incorporated herein by reference). The LTVEC was constructed by replacing a genomic sequence of 251 bp between mouse Cr2 and Cr1l loci with a human genomic sequence of 131,456 bp which includes the entire CR1 locus from ATG to STOP, with the 5' and 3' untranslated regions (UTRs) and intervening introns, as well as an additional sequence of 4,233 bp (SEQ ID NO: 3) directly upstream of the 5' UTR and a sequence of 159 bp (SEQ ID NO: 41) directly downstream of the 3' UTR. The mouse sequence of 251 bp being replaced is downstream of the Cr1 3' UTR and upstream of the Cr1l 5' UTR. A self-deleting hygromycin resistance cassette (which contains a protamine-promoter driven Cre that deletes in the male germ cells) was placed directly downstream of the 131,456 bp human insert. See FIG. 1A.

The resultant vector was used to electroporate hybrid 129S6/SvEvTac:C57B1/6Ntac F1 mouse embryonic stem (ES) cells and positive selection was accomplished based on hygromycin resistance. Correctly targeted ES cells were identified by a modification of allele assay (MOA). Specific primer sets and probes were designed for detecting deletion of mouse sequences (loss of allele or LOA) and insertion of the human sequences (gain-of-allele or GOA). The locations of the primers and probes are depicted in FIG. 1A.

TABLE 2

Primer and Probes Used to Confirm Loss of Mouse Sequence (LOA) or Gain of Human Sequence (GOA)

| Description | Sequence | SEQ ID NO |
|---|---|---|
| 7238mTU | Fwd: TGAGCCTACTCAACCTTAACAGT | 5 |
| | Probe (BHQ): TCTGTCTGGTGGCAT AGTTCACTTGC | 6 |
| | Rev: TGGCCTGTTTGAAGGAATTGTTG | 7 |
| 7238mTD | Fwd: GCATGCAAACAAACCATTGGAA | 8 |
| | Probe (BHQ): AAAGGAAATGAGAAG ACAGTAAAACCTGCA | 9 |
| | Rev: CCCGTCTAAGAAACACTGAGGTA | 10 |

TABLE 2-continued

Primer and Probes Used to Confirm Loss of Mouse Sequence (LOA) or Gain of Human Sequence (GOA)

| Description | Sequence | SEQ ID NO |
|---|---|---|
| 7238hTU | Fwd: GCAGTGGAAGGCGCAGATG | 11 |
| | Probe (BHQ): AGCGGGTGCCGCACG AAATTC | 12 |
| | Rev: CAGCCGAGGCTGTGAATACAC | 13 |
| 7238hTD | Fwd: TGGGCAAAGGACATACAGCTA | 14 |
| | Probe (BHQ): TCACCAAGAAAGAAG GGCATAAAGGTGG | 15 |
| | Rev: GGCCAATTCCCAATCACTTAGTTTC | 16 |

Correctly targeted ES clones were used as donor ES cells and microinjected into 8-cell stage Swiss Webster embryos, resulting in F0 VelociMice® fully derived from the injected modified ESC (Poueymirou 2007; Nature Biotech 25(1):91-99). These F0 mice, designated MAID 7238, were subsequently bred to 100% C57B1/6NTac mice. The resistance cassette in MAID 7238 was removed by self-deleting technology, resulting in MAID 7239.

Example 2—Phenotyping of Mouse Comprising Targeted Insertion of Human CR1

Figure 2A:
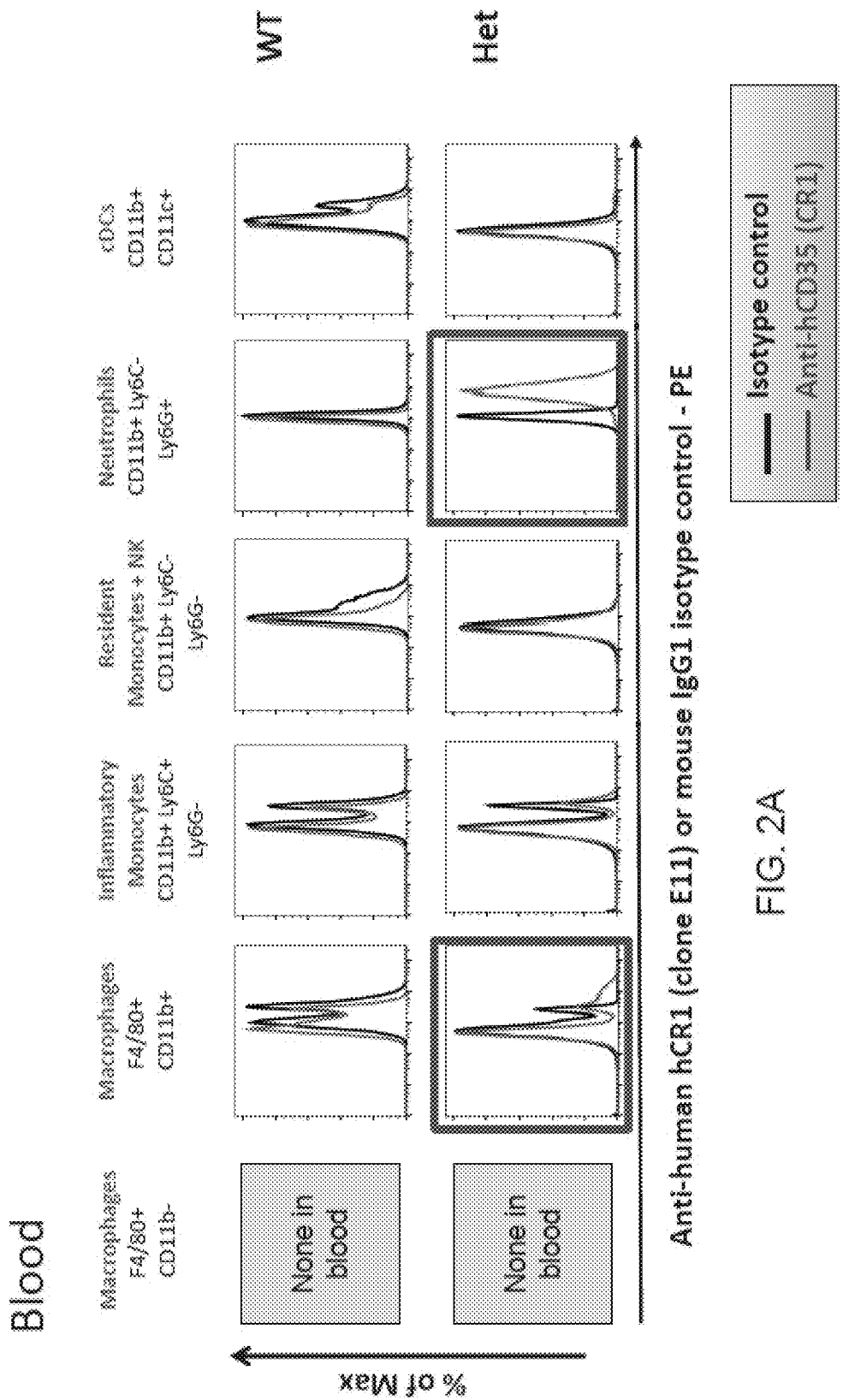
FIG. 2A. Flow cytometry analysis of blood myeloid cell populations of mice heterozygous for targeted insertion of human CR1 (MAID7239 Het, or "Het"), as compared to WT control mice having 75% B6 25%129 background ("75/25 WT") (having the same genetic background as MAID 7239 but without the targeted insertion of human CR1). Human CR1 was detected on neutrophils at a high level and on macrophages at a very low level.
Figure 2B:
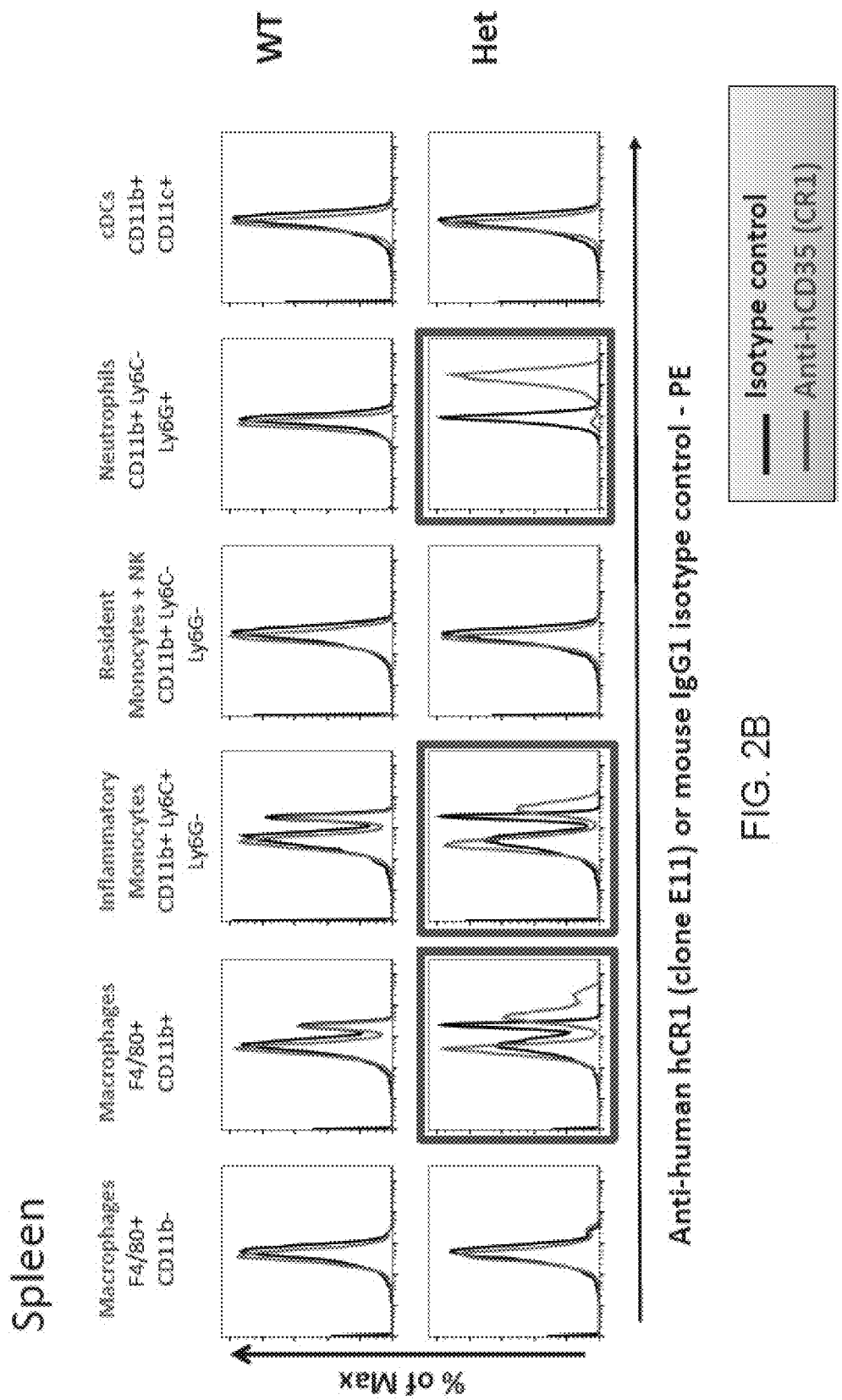
FIG. 2B. Flow cytometry analysis of myeloid splenic cell populations of mice heterozygous for targeted insertion of human CR1 (MAID 7239, or "Het"), as compared to WT control mice having 75% B6 25%129 background ("75/25 WT") (having the same genetic background as MAID 7239 but without the targeted insertion of human CR1). Human CR1 was detected on neutrophils at a high level, and on macrophages and inflammatory monocytes at a very low level.

Phenotyping of MAID 7239 Het (F1 mice heterozygous for targeted insertion of human CR1 with SDC deleted)—Flow cytometry was performed on cells from the whole blood, lysed blood, and spleen of MAID 7239 Het mice (F1: 10 wk old, males, n=3, 75%/25% B6/129 background) and MAID 7238 wild type mice (10 wk old, males, n=3, 75%/25% B6/129 background). MAID 7239 Het mice had normal myeloid cell populations in the blood and in the spleen as compared to MAID 7238 wild type mice. As shown in FIG. 2A for cells from the lysed blood, a high level of hCR1 was detected on neutrophils (at approximately the same expression level seen in human blood), and a very low level of hCR1 was detected on macrophages. However, hCR1 was not detectable on red blood cells (RBCs) from the whole blood. As shown in FIG. 2B for cells isolated from the spleen, a high level of hCR1 was detected on neutrophils, and a very low level of hCR1 was detected on macrophages and inflammatory monocytes.

Figure 2C:
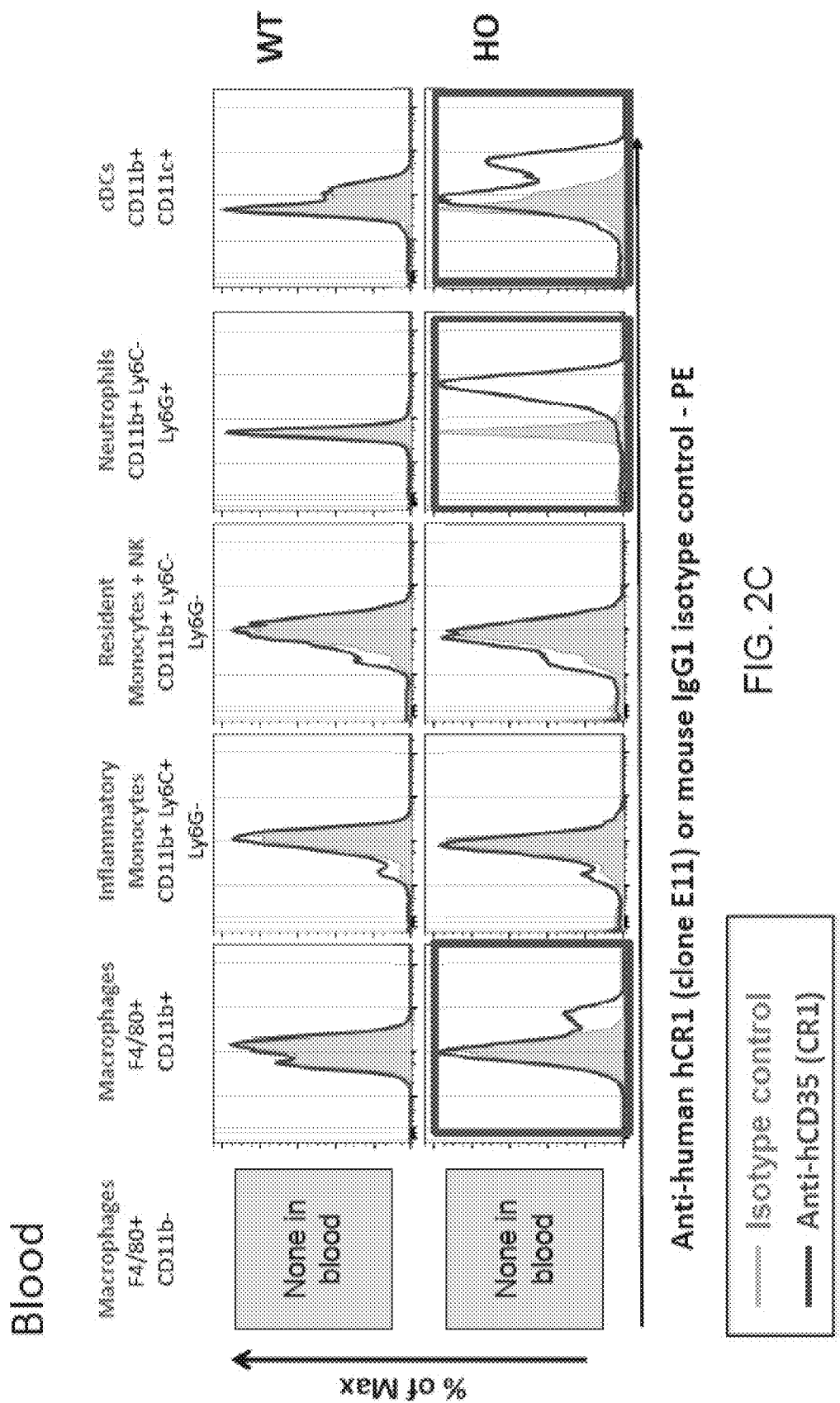
FIG. 2C. Flow cytometry analysis of myeloid blood cell populations of mice homozygous for targeted insertion of human CR1 (MAID7239 HO, or "HO"), as compared to WT control mice having 75% B6 25%129 background ("75/25 WT") (having the same genetic background as MAID 7239 but without the targeted insertion of human CR1). Human CR1 was detected on neutrophils at a high level, on circulating dendritic cells (cDCs) at a moderate level, and on macrophages at a very low level.
Figure 2D:
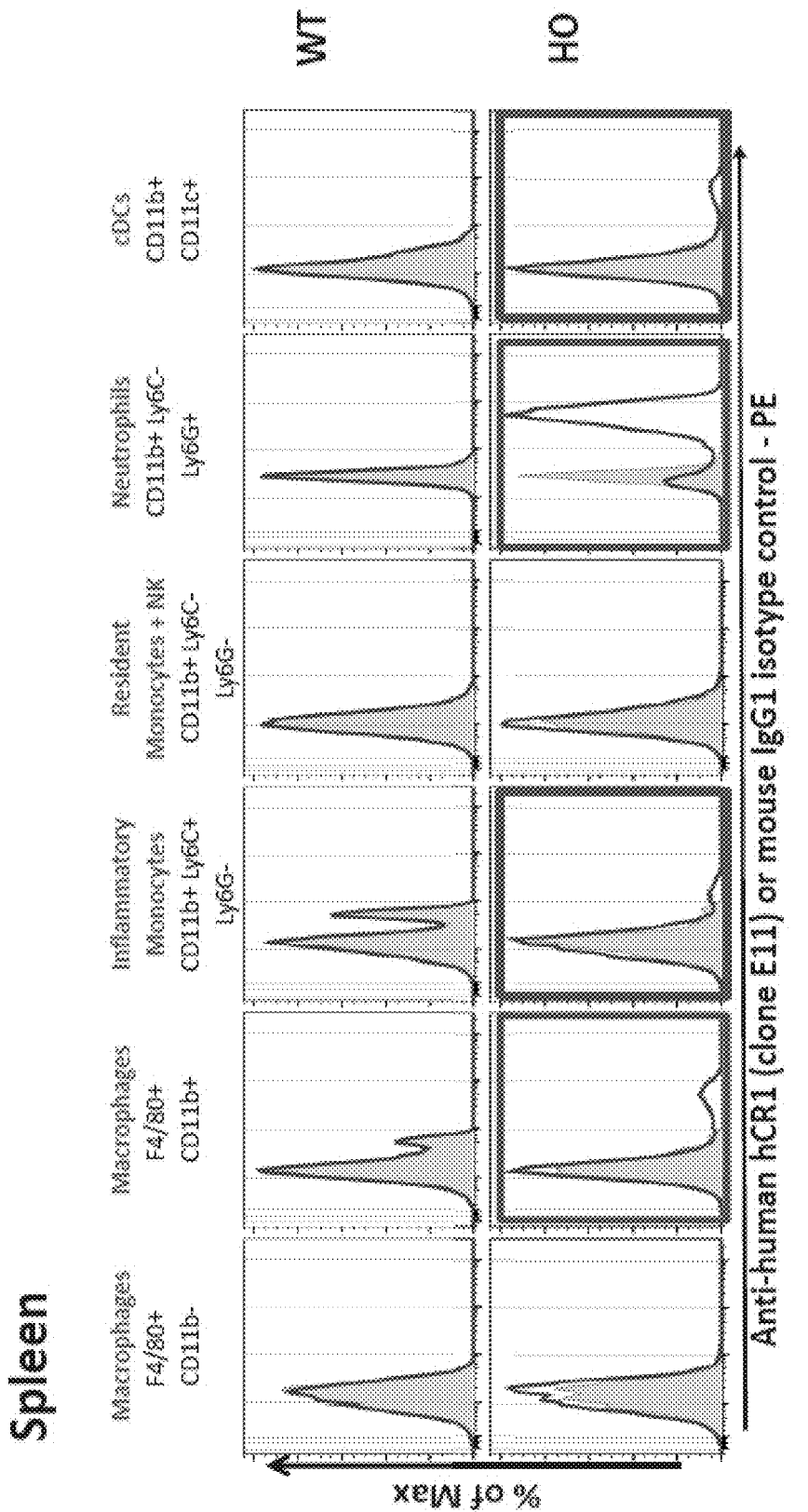
FIG. 2D. Flow cytometry analysis of myeloid splenic cell populations of mice homozygous for targeted insertion of human CR1 (MAID7239 HO, or "HO"), as compared to WT control mice having 75% B6 25%129 background ("75/25 WT") (having the same genetic background as MAID 7239 but without the targeted insertion of human CR1). Human CR1 was detected on splenic neutrophils at a high level, and on circulating dendritic cells (cDCs), macrophages and inflammatory monocytes at a very low level.
Figure 2E:
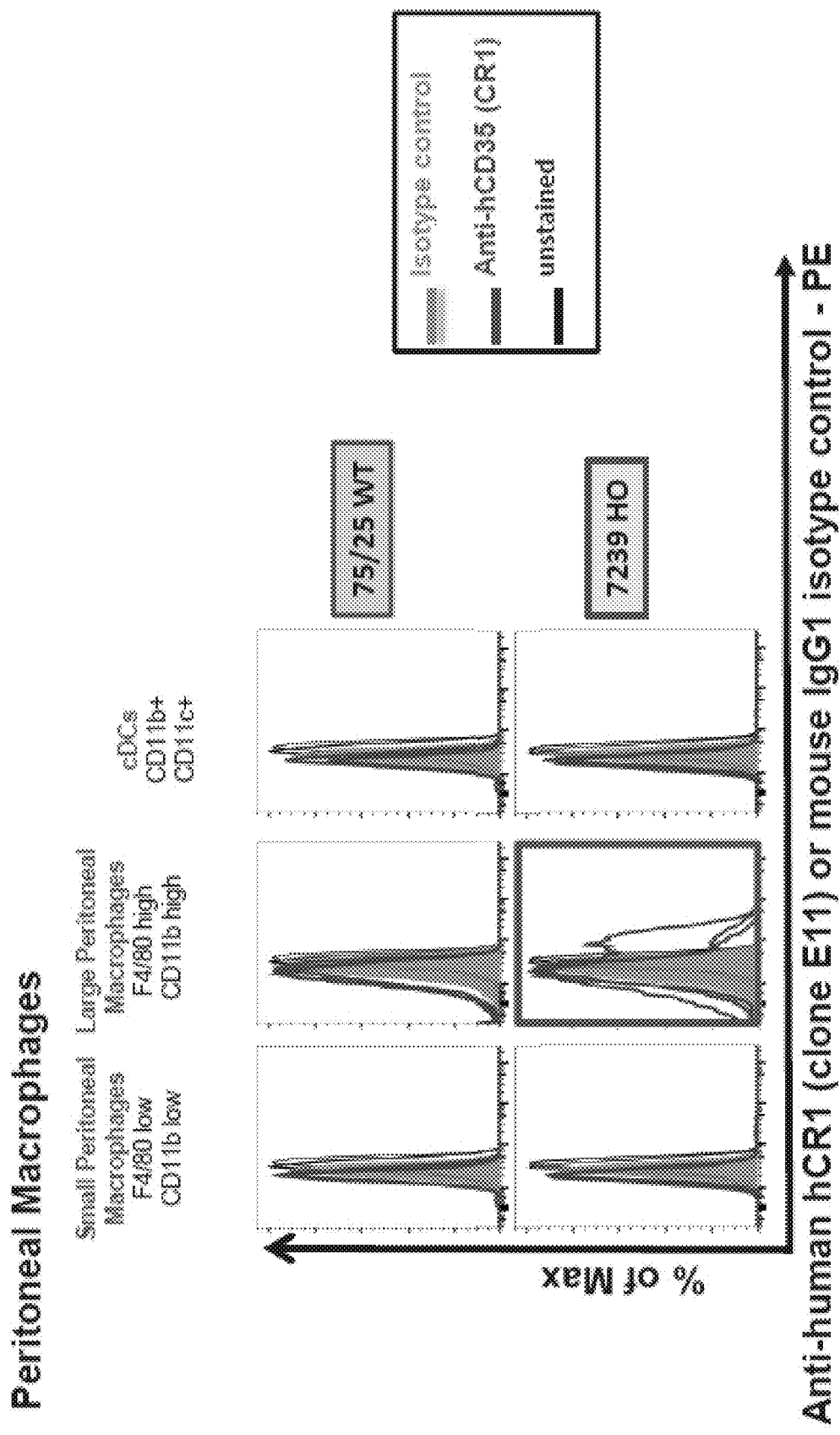
FIG. 2E. Flow cytometry analysis of macrophage populations in peritoneal cavity of mice homozygous for targeted insertion of human CR1 (MAID7239 HO, or "HO"), as compared to wild type control mice having 75% B6 25%129 background ("75/25 WT"). Large Peritoneal Macrophages are derived from fetal liver derived monocytes or yolk-sac. Small Peritoneal Macrophages are derived from bone marrow derived monocytes. hCR1 was detected on a few large (but not small) peritoneal macrophases in 1 of 3 MAID7239 HO mice examined.
Figure 2F:
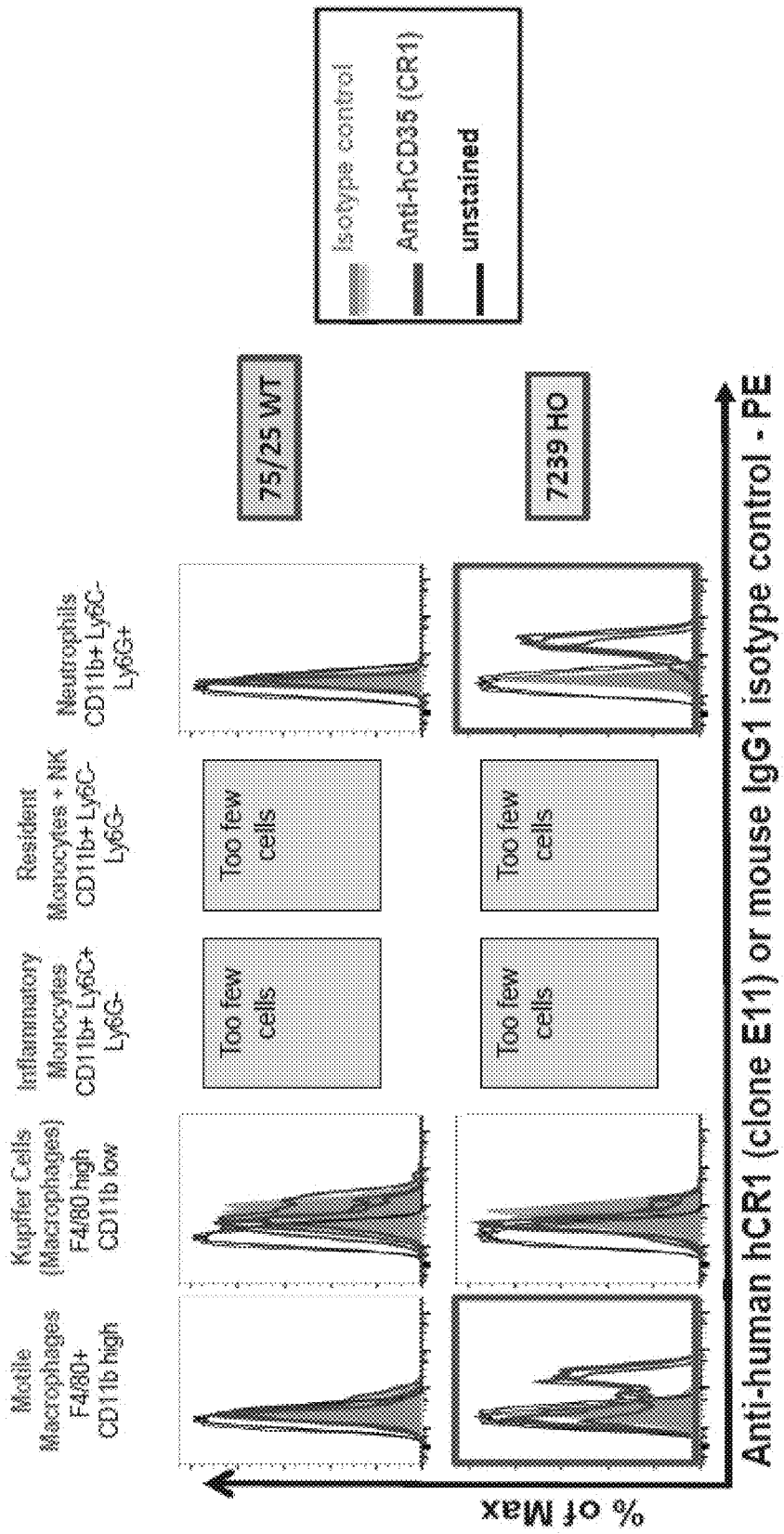
FIG. 2F. Flow cytometry analysis of macrophage populations in the liver of mice homozygous for targeted insertion of human CR1 (MAID7239 HO, or "HO"), as compared to wild type control mice having 75% B6 25%129 background ("75/25 WT"). hCR1 was detected on all neutrophils in the liver, and on approximately 50% motile macrophases (and possibly cDCs), but not on Kupffer cells, from MAID7239 HO mice.

Phenotyping of MAID 7239 HO (F2 mice homozygous for targeted insertion of human CR1 with SDC deleted)—Flow cytometry was performed on cells from the whole blood, lysed blood, and spleen of MAID 7239 HO mice (F2: 6-7 wk old, males, n=3 (data not shown); 12 week old, females, n=3; 75% B6 25%129 background) and MAID 7239 wild type mice (6-7 wk old, males, n=3 (data not shown); 12 wk old, females, n=3; 75%B6 25% 129 background). MAID 7239 HO mice had normal myeloid cell populations in the blood and in the spleen as compared to MAID 7239 wild type mice. As shown in FIG. 2C for cells from the lysed blood, a high level of hCR1 was detected on neutrophils (at approximately the same expression level seen in human blood); a moderate level of hCR1 was detected on cDCs, and a low level of hCR1 was detected on macrophages. However, hCR1 was not detectable on red blood cells (RBCs) from the whole blood. As shown in FIG. 2D for cells isolated from the spleen, a high level of hCR1 was detected on neutrophils, and a very low level of hCR1 was detected on macrophages, inflammatory monocytes and cDCs. Flow cytometry was performed on cells from the peritoneal cavity and digested liver of MAID 7239 HO mice (75% C57BL/6NTac 25% 129S6/SvEvTac background, Males n=2, Female n=1, 15 weeks old, F6) and MAID 7239 wild type mice (75/25WT (50500): 75% C57BL/6NTac 25% 129S6/SvEvTac background, Males n=2, Female n=1, 15 weeks old, F1). hCR1 was also detected on a few large (but not small) peritoneal macrophases in 1 of 3 mice examined (FIG. 2E). hCR1 was detected on all neutrophils in the liver, and on approximately 50% motile macrophages (and possibly cDCs) (FIG. 2F).

Materials and Methods

All mice were housed and bred in the specific pathogen-free conditions at Regeneron Pharmaceuticals. Mice were sacrificed, and spleens and blood were harvested. Blood was collected into BD microtainer tubes with EDTA (Cat #365973). Red blood cells from spleen and blood preparations were lysed with ACK lysis buffer, followed by washing with complete RPMI medium. In some instances, liver and peritoneal cells were harvested. Liver was collected, chopped into small pieces and digested in a mix of Liberase TH (Cat #5401151001, Roche, used at a final concentration of 0.7 U/ml) and DNase (cat #10104159001, Roche, used at a final concentration of 20 ug/ml) in HBSS for 20 min at 37° C., after which reaction was stopped with EDTA at a final concentration of 10 mM, followed by washing with complete RPMI medium and red cell lysis with ACK lysis buffer. Peritoneal macrophages were collected via peritoneal lavage by flushing peritoneal cavity with 5-6 ml of ice-cold PBS with a 27 g needed using a 10 ml syringe. Red cells were lysed with ACK, followed by washing with complete RPMI medium.

Flow cytometry on unlysed blood, lysed blood and spleen: $1 \times 10^6$ cells were incubated with anti-mouse CD16/CD32 (2.4G2, BD) on ice for 10 minutes, followed by labeling with the following antibody panels for 30 min on ice. Panel used on unlysed blood: anti-mouse PeCy7—TER119 (TER119, BD), anti-human PE-CR1 (E11, BD) or PE-IgG1, K isotype control (MOPC-21, BD). Panel used on lysed blood, spleen, liver, peritoneal lavage: anti-mouse FITC-Ly6C (HK1.4, Biolegend), PeCy7-F4/80 (BM8, Biolegend), PerCP-Cy5.5-Ly6G (1A8, BD), Pacific Blue-CD3 (17A2, BioLegend), APC-CD11c (N418, Biolegend), APC-eFlour780-CD11b (M1/70, eBioscience), A700-CD19 (1D3, BD) and anti-human PE-CR1 (E11, BD) or PE-IgG1, K isotype control (MOPC-21, BD).

Flow cytometry on liver and peritoneal lavage: $1 \times 10^6$ cells were first washed in PBS then incubated with LIVE/DEAD™ Fixable Yellow Dead Cell Stain (Cat #L34959, Invitrogen) for 30 min on ice, followed by washing in PBS, then incubation with anti-mouse CD16/CD32 (2.4G2, BD) on ice for 10 minutes, followed by labeling with the following antibody panels for 30 min on ice.

Following staining, cells were washed and fixed in 2% formaldehyde. Data acquisition was performed on a BD LSRFortessa™ Flow Cytometer and analyzed with FlowJo software.

Macrophages (F4/80+CD11b− and F4/80+CD11b+), Inflammatory Monocytes (CD11b+Ly6C+Ly6G−), Resident Monocytes & NK cells (CD11b+Ly6C−Ly6G−), Neutrophils CD11b+Ly6C−Ly6G+), cDCs (CD11b+CD11c). In the peritoneal cavity, small Peritoneal Macrophages (F4/80 lowCD11b low), Large Peritoneal Macrophages (F4/80 high CD11b high), cDCs (CD11b+CD11c+). In the liver, Motile Macrophages (F4/80+CD11b high), Kupffer Cell Macrophages (F4/80 high CD11b low), Neutrophils (CD11b+Ly6C−Ly6G+).

Example 3. Generation and Phenotyping of Mouse Comprising Targeted Insertion of Human CRI and Human C3

MAID 6149 mice were generated by replacing the mouse C3 gene locus spanning 5' regulatory elements and all of the coding exons 1 through 41 with a human genomic fragment comprising 5' regulatory elements and all of the coding exons 1 through 41 of the human C3 gene (see, e.g., U.S. Pat. No. 9,795,121 B1, incorporated herein by reference). MAID 6149 mice were shown to be prone to high rates of spontaneous death and exhibit physiological, morphological, and histological symptoms which closely resemble complement-related nephropathies and liver fibrosis. MAID7239 HO mice described in Example 1 were crossed with MAID6149 mice to produce doubly homozygous mice in order to assess the effect of CR1 humanization on disease phenotypes in MAID6149 mice.

In the experiments described in this Example, the following mice were used: C3 HumIn CR1 HumIn (6149HO 7239HO) mice: 75% C57BL/6NTac 25% 129S6/SvEvTac background, Male, n=9, F2 and Female, n=6, F2; C3 HumIn (6149HO 7239WT)—75% C57BL/6NTac 25% 129S6/SvEvTac background, Male, n=5, F2 and Female, n=2, F2; 75/25 WT (50500): 75% C57BL/6NTac 25% 129S6/SvEvTac background, Male, n=10, F1 and Female, n=4, F1.

Materials and Methods

Mice were sacrificed and serum was collected in BD tube #365967.

Mouse C3 was measured with Complement C3 Mouse ELISA Kit (Cat #ab157711, Abcam) as per manufacturer's instructions. The absorbance at 450 nm was determined on the Molecular Devices SpectraMax M5. Data was analyzed in Prism software.

Human C3 was measured with Complement C3 Human ELISA Kit (Cat #ab108822, Abcam) as per manufacturer's instructions. The absorbance at 450 nm was determined on the Molecular Devices SpectraMax M5. Data was analyzed in Prism software.

Human iC3b was measured with MicroVue Complement iC3b Human EIA Kit (Cat #ab108822, Quidel) as per manufacturer's instructions. The absorbance at 450 nm was determined on the Molecular Devices SpectraMax M5. Data was analyzed in Prism software.

Blood urea nitrogen was measured with a QuantiChrom Urea Assay Kit (Cat #DIUR-100, Bioassay Systems) as per manufactur's instructions.

Cohort #1

Visual inspection and serum BUN levels (serum biomarker of kidney injury) were used as indicator of disease progression in C3 HumIn (MAID6149HO) mice and C3 HumIn CR1 HumIn (MAID 6149HO 7239HO) mice, as compared to WT controls. Upon finding sick mice with elevated BUN levels, the mice were sacrificed to collect serum and tissues. The analysis shows moderate improvement in BUN levels in C3 HumIn CR1 HumIn (6149HO 7239HO) mice compared to C3 HumIn (6149HO) mice, despite no improvement in hC3 levels; and possible indication of exacerbated liver injury, with an improvement in kidney injury, in C3 HumIn CR1 HumIn (6149HO 7239HO) mice compared to C3 HumIn (6149HO) mice. See FIGS. 3A-3E.

Cohort #2

Figure 3A:
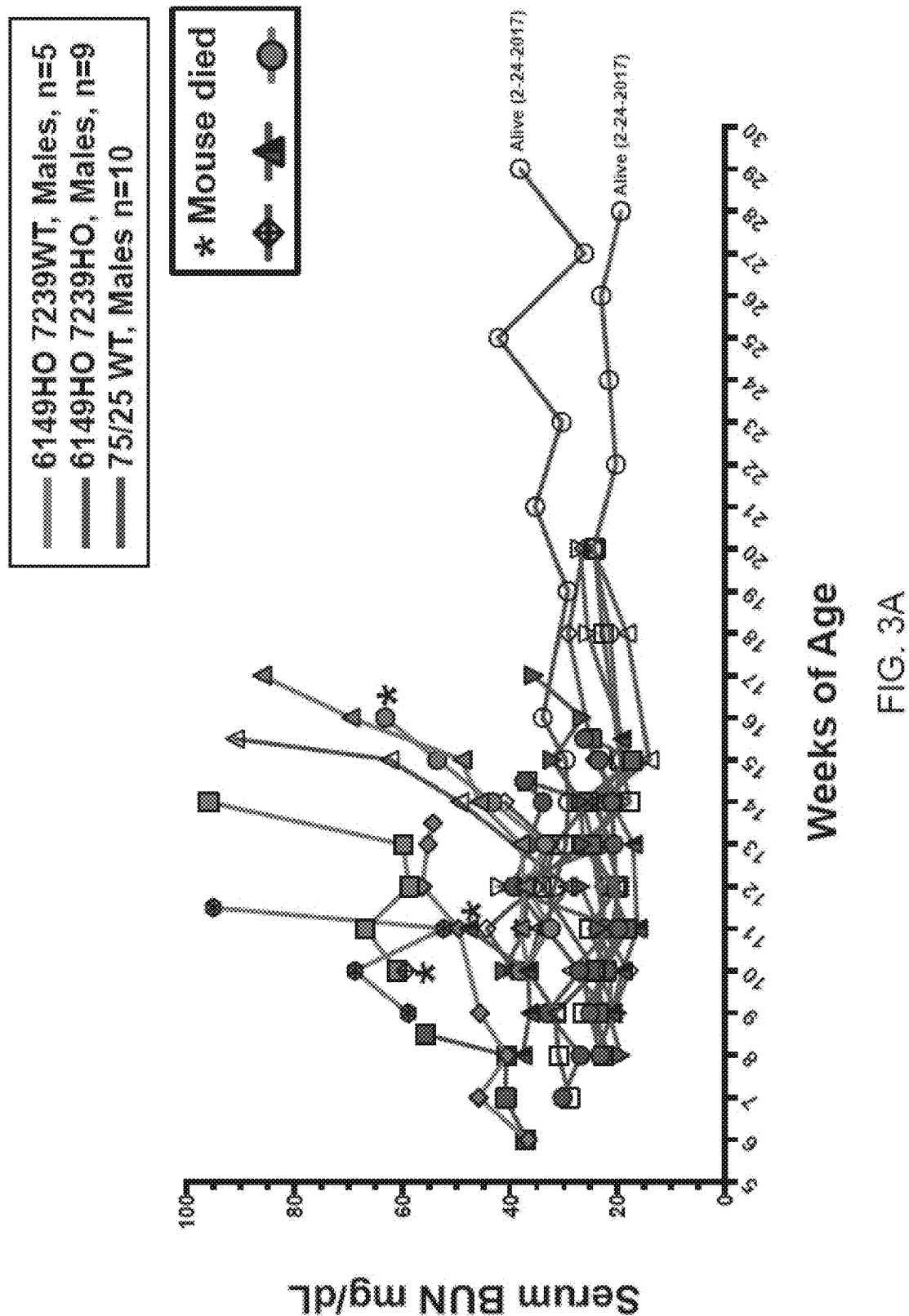
FIG. 3A shows a moderate decrease in serum BUN levels in C3 Humin CR1 Humin (6149HO 7239HO) male mice as compared to C3 Humin (6149HO 7239WT) male mice. Mice were sacrificed unless indicated with * (which indicates that the mouse died).
Figure 3B:
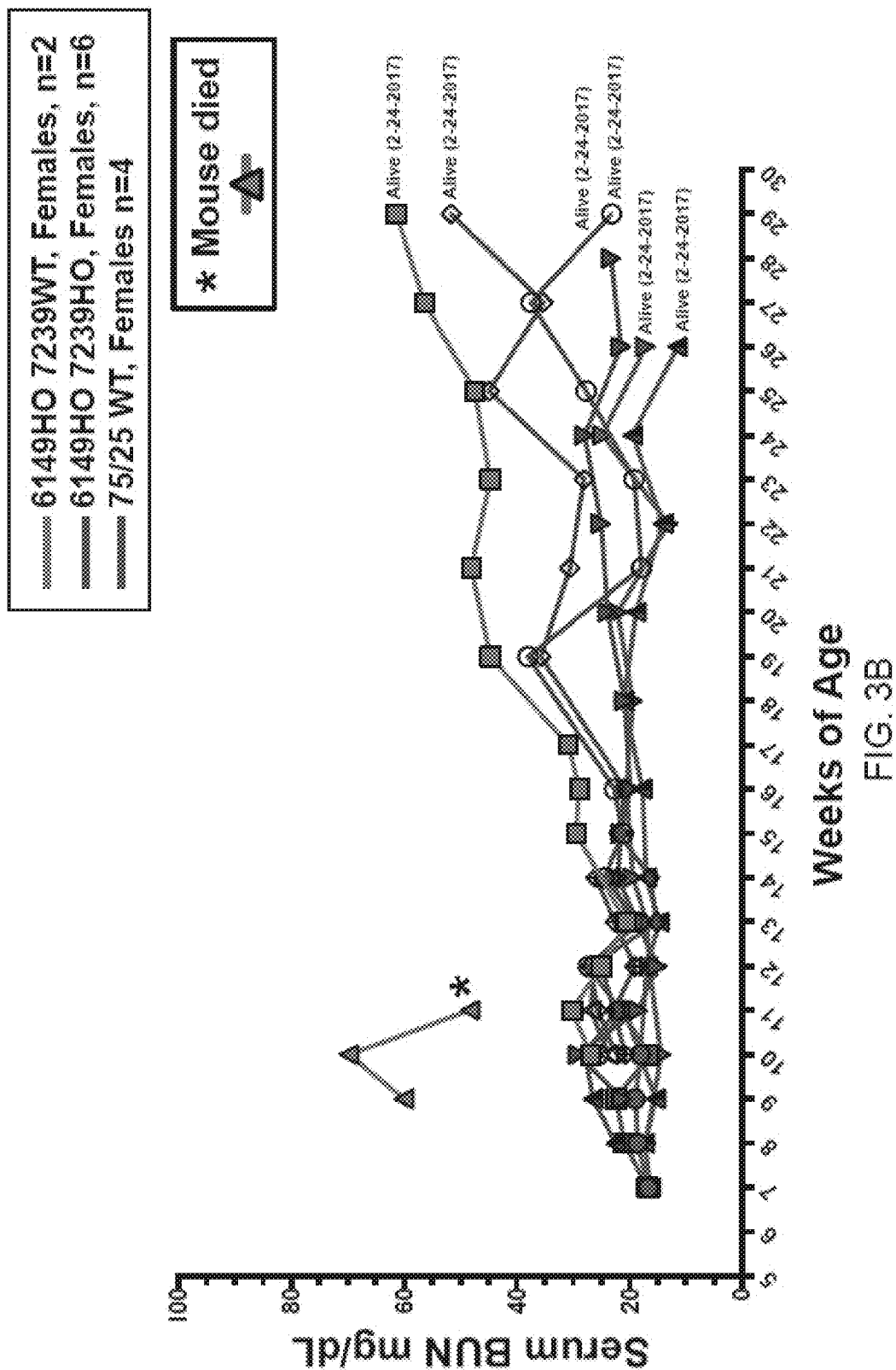
FIG. 3B shows a moderate decrease in serum BUN levels in C3 HumIn CR1 HumIn (6149HO 7239HO) female mice as compared to C3 HumIn (6149HO 7239WT) female mice. Mice were sacrifice unless indicated with * (which indicates that the mouse died).
Figure 3C:
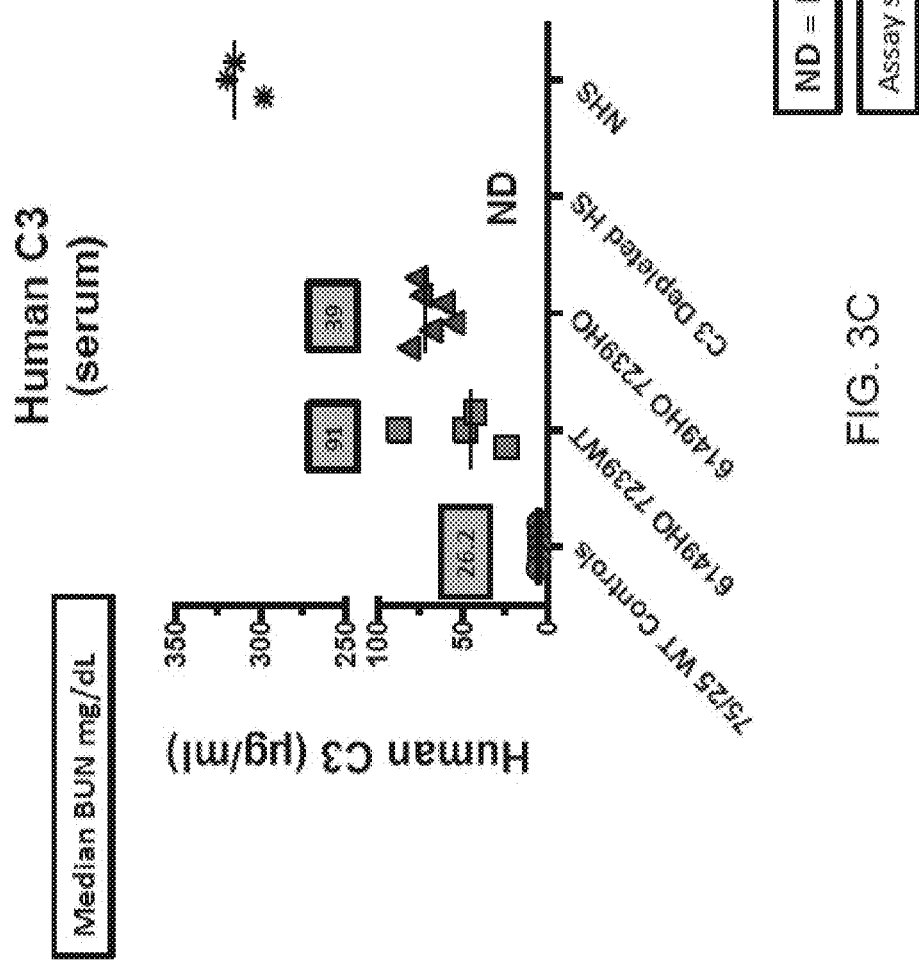
FIG. 3C shows a lack of significant improvement in hC3 serum levels in C3 HumIn CR1 HumIn (6149HO 7239HO) mice as compared to C3 HumIn (6149HO 7239WT) mice. Published C3 concentration in normal human serum is about 1200 □g/ml. Horizonal bars represent medians.
Figure 3D:
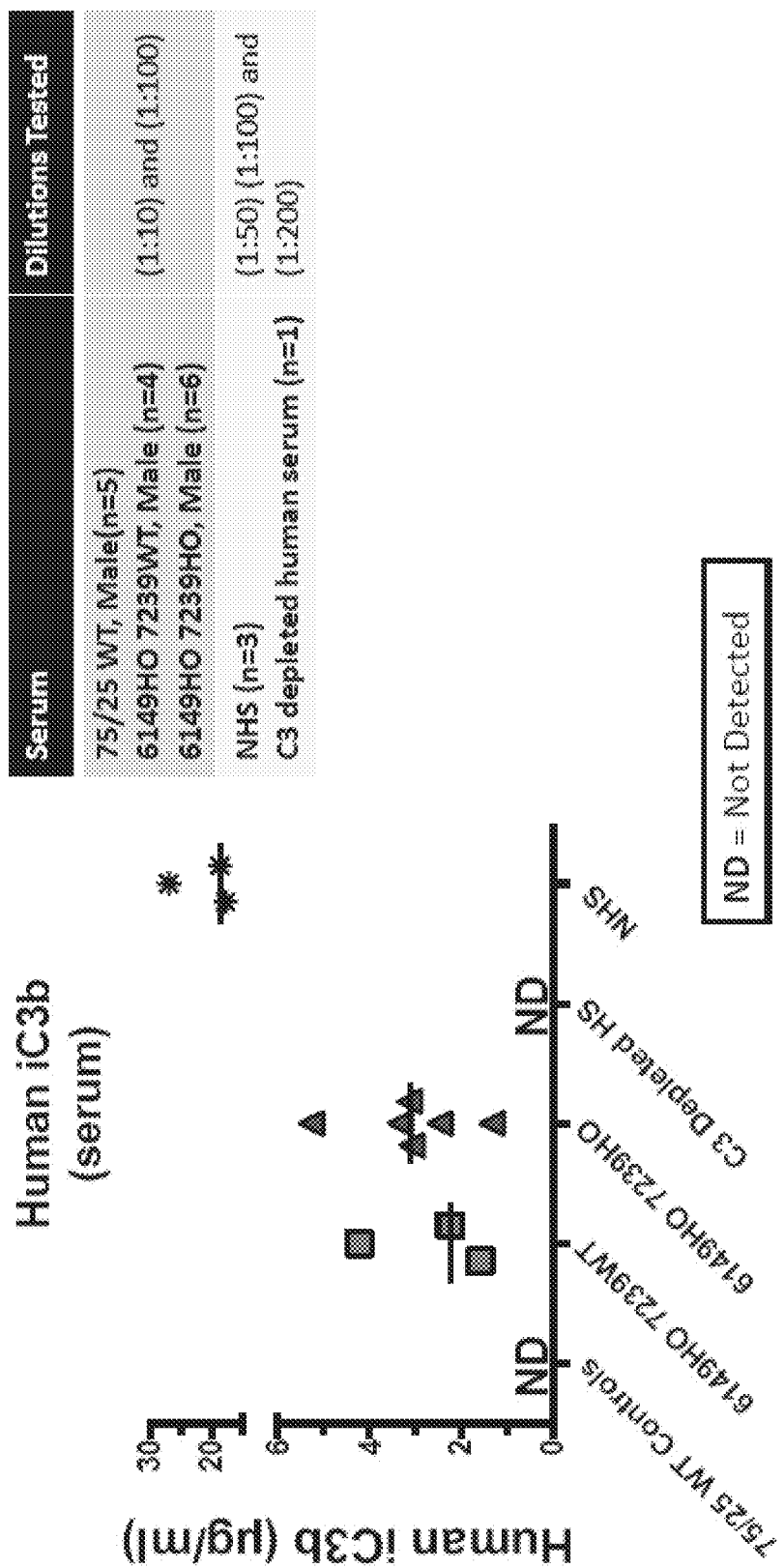
FIG. 3D illustrates that C3 HumIn CR1 HumIn (6149HO 7239HO) mice show no change in human iC3b serum levels compared to C3 HumIn (6149HO 7239WT) mice. The ratio of C3: iC3b was found to be similar between Normal Human Serum (NHS) and 6149HO 7239WT serum.
Figure 3F:
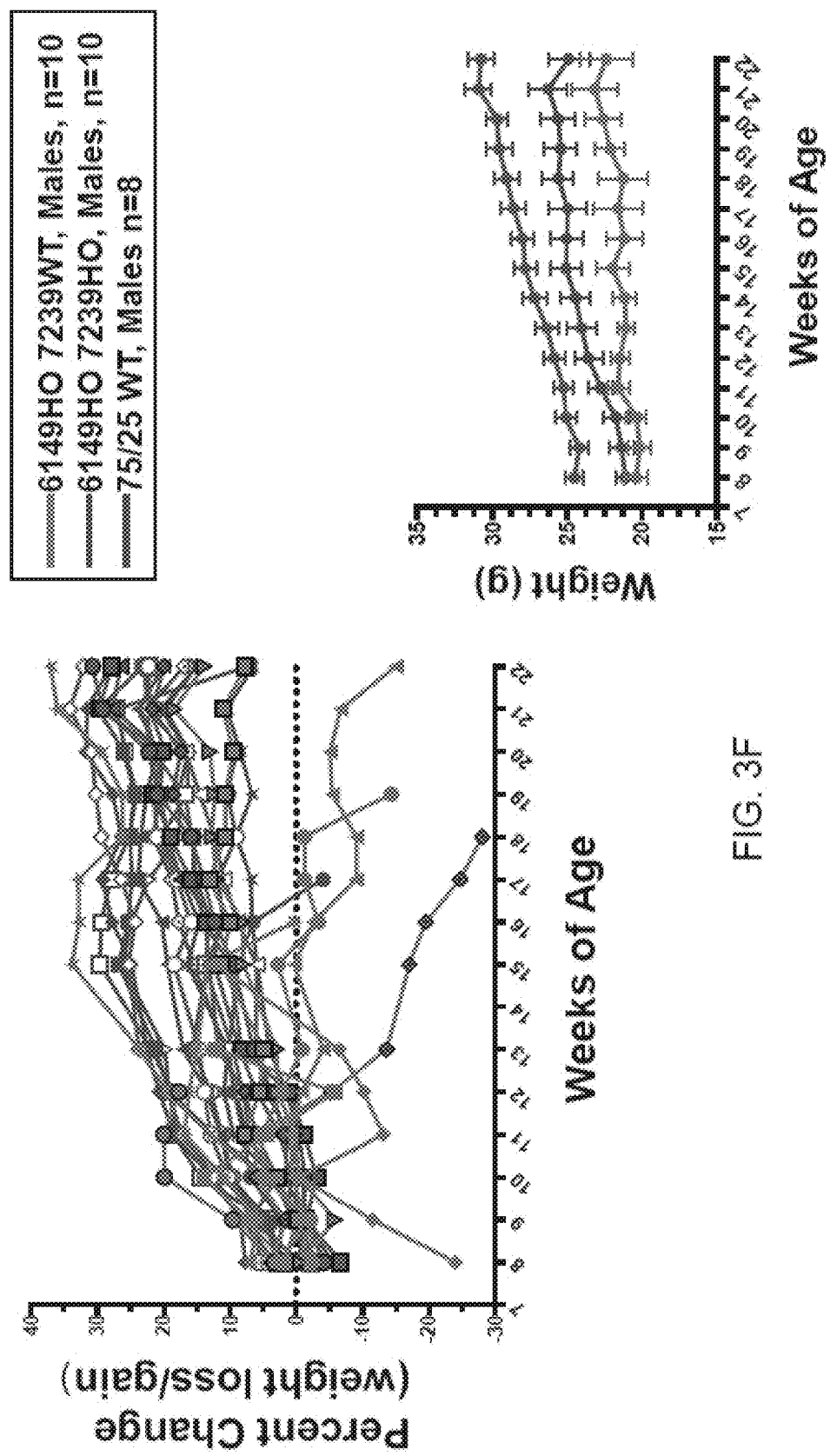
FIG. 3F shows a minor improvement in weight gain in C3 HumIn CR1 HumIn (6149HO 7239HO) mice as compared to C3 HumIn (6149HO 7239WT) mice. Both C3 HumIn CR1 HumIn and C3 HumIn mice failed to gain weight with age compared to 75/25 WT Controls.
Figure 3G:
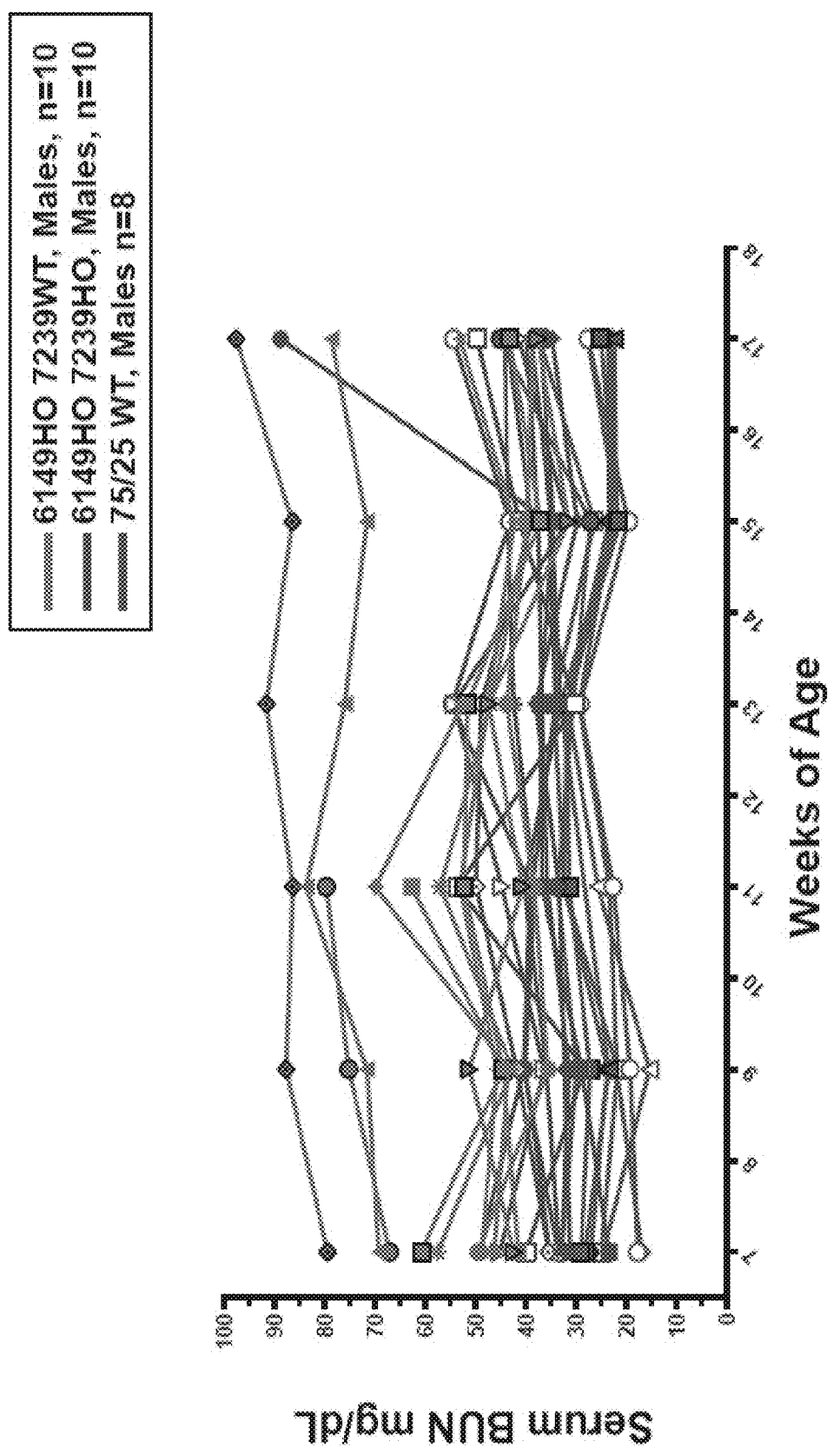
FIG. 3G shows a minor decrease in serum BUN levels in C3 HumIn CR1 HumIn (6149HO 7239HO) mice as compared to C3 HumIn (6149HO 7239WT) mice. Both C3 HumIn CR1 HumIn (6149HO 7239HO) and C3 HumIn (6149HO 7239WT) mice have elevated serum BUN levels as compared to 72/25 WT controls.
Figure 3H:
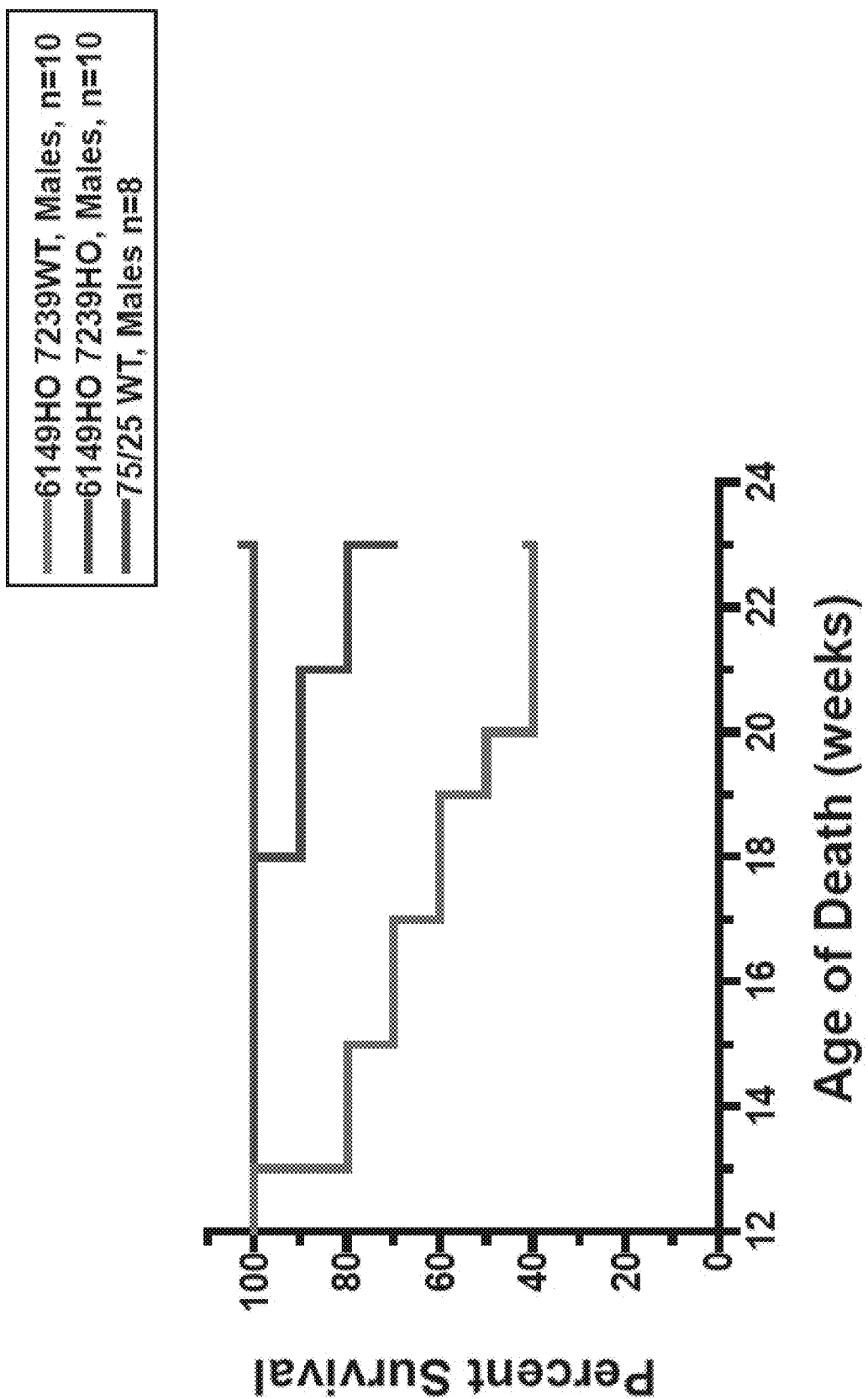
FIG. 3H shows improved survival in C3 HumIn CR1 HumIn (6149HO 7239HO) mice as compared to C3 HumIn (6149HO 7239WT) mice.

Weight gain, BUN levels (serum biomarker of kidney injury), and survival were examined in C3 HumIn (MAID6149HO) mice and C3 HumIn CR1 HumIn (MAID 6149HO 7239HO) mice, as compared to WT controls. As shown in FIGS. 3F-3H, minor improvement in weight gain/BUN levels and significant improvement in survival were observed in C3 HumIn CR1 HumIn (6149HO 7239HO) mice compared to C3 HumIn (6149HO) mice.

Example 4. Generation of Mouse Comprising Transgenic Human CRI Driven by a Mouse GATA-1 Promoter Mouse Gata1 gene is located at X chromosome, and its genomic sequence can be found under NCBI Gene ID number 14460. Examples of RefSeq mRNA ID and UniProt ID can be found under GenBank Accession No. NM_008089.2 and UniProt ID No. P17679, respectively.

Figure 4A:
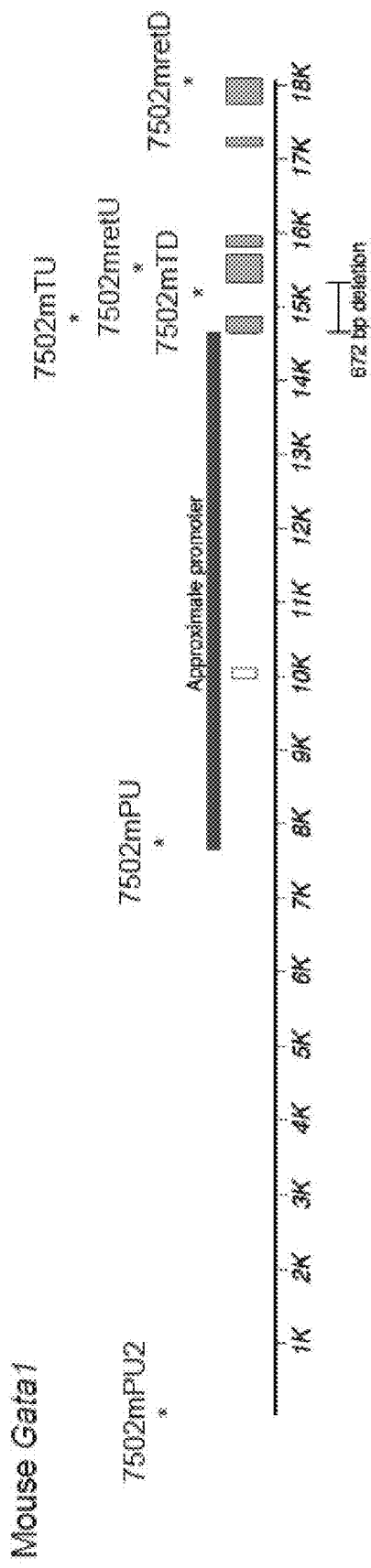
FIG. 4A shows the mouse Gata 1 gene locus, with exons being represented by vertical boxes. The location of the mouse genomic sequence of 672 bp to be deleted and replaced by a human CR1-coding sequence is indicated. The locations for the primer sets and probes designed for detecting deletion of mouse sequences (loss of allele or LOA) (7502 mTU and 7502 mTD), for confirming the presence of mouse Gata1 promoter (7502 mPU and 7502 mPU2), and for retention of mouse Gata1 sequences (7502 mretU and 7502 mretD) are also indicated.
Figure 4B:
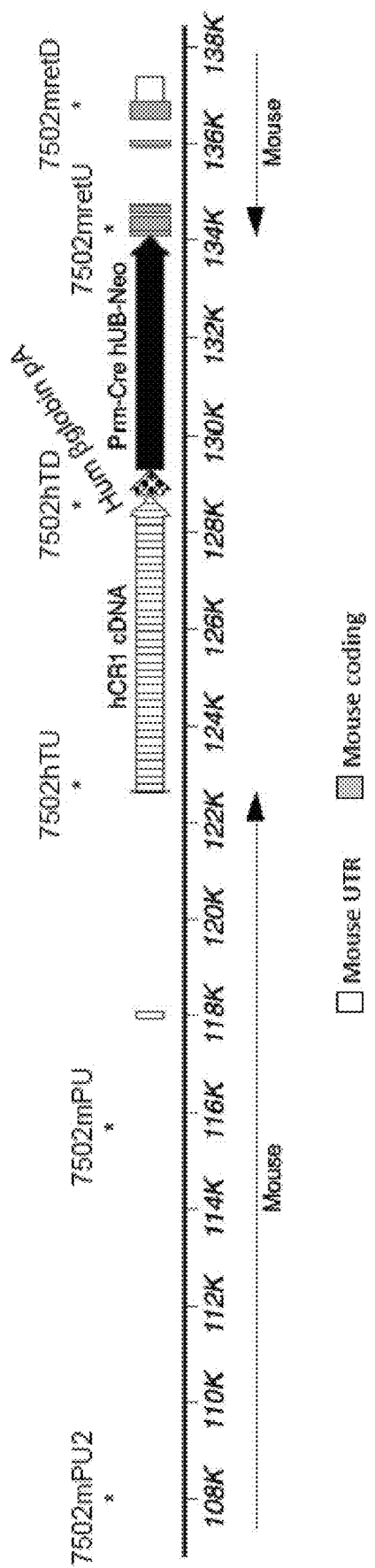
FIG. 4B shows the 7502 allele, with a mouse Gata1 promoter-human CR1 coding sequence randomly integrated and containing a self-deleting neomycin resistance cassette. Full-length human CR1 coding sequence (ATG to STOP, 6117bp) was inserted into a mouse bacterial artificial chromosome (BAC) containing Gata1 genomic sequence such that 672 bp of Gata1, encompassing mouse coding exon 1 sequence just after the ATG start codon and the following mouse intron, was replaced. The mouse BAC was chosen to include >7Kb sequence upstream of the Gata1 ATG and >1.5Kb sequence downstream of the Gata1 stop codon. A 3' UTR sequence containing the poly(A) signal (135 bp, SEQ ID NO: 4) from a human beta-1 globin gene was inserted just after the human CR1 stop, followed by a self-deleting neomycin resistance cassette (4810 bp). The locations for the primer sets and probes designed for detecting gain of human sequences (7502 hTU and 7502 hTD), for confirming the presence of mouse Gata1 promoter (7502 mPU and 7502 mPU2), and for retention of mouse Gata1 sequences (7502 mretU and 7502 mretD)are also indicated.
Figure 4C:
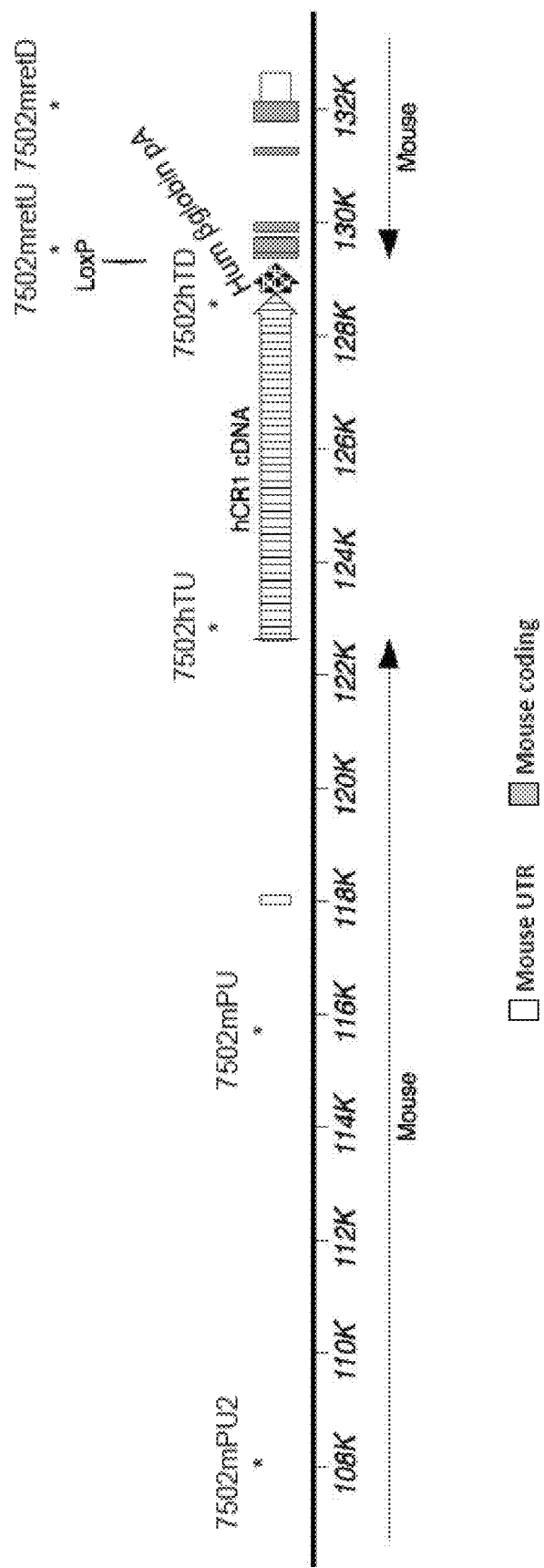
FIG. 4C shows the 7503 allele, resulting from cassette deletion from the 7502 allele shown in FIG. 4B. Following cassette deletion, a 78 bp scar containing a loxP site remains.

The genetically engineered TG$^{Gata1-CRI}$ mouse strain containing a randomly inserted copy of mouse Gata1 promoter-human CR1 cDNA-human beta globin polyA sequence was created using Regeneron's VelociGene® technology (Valenzuela 2003, supra; Poueymirou 2007, supra). Hybrid 12956/SvEvTac:C57B1/6NTac F1 embryonic stems cells (ESC) were targeted for random insertion of a mouse bacterial artificial chromosome (BAC) containing Gata1 genomic sequence (including 33 Kb upstream of ATG), modified so that a full-length human CR1 coding sequence (ATG to stop) replaced coding exon 1 and the following intron of Gata1. A 3' UTR sequence containing the poly(A) signal from a human beta globin gene, as set forth in SEQ ID NO: 4, was placed 3' to the human CR1 stop codon, followed by a neomycin resistance cassette for selection in ESCs. See FIG. 4A-4B.

To ensure that human CR1 protein would express in a Gata1 dependent manner, ESC clones were screened to ensure that at least 14 Kb (and possibly entire 33 Kb) upstream of ATG (including Gata1 promoter) (determined by TaqMan assay) and 1.5 Kb of 3' UTR (determined by Targeted Locus Amplification ("TLA") analysis) were included in transgene insertions. Clones were also screened by TaqMan to ensure that the transgene did not target endogenous Gata1 (located on the X chromosome). The sequences of the primer sets and probes are set forth in Table 3 below, with their locations depicted in FIG. 4A.

TABLE 3

Primer and Probes in Mouse Taqman LOA Assays (7502mTU and 7502mTD), Human Taqman GOA Assays (7502hTU and 7502hTD), Mouse Promoter Assays (7502mPU and 7502mPU2), and Mouse Retention Assays (7502mretU and 7502retD)

| Description | Sequence | SEQ ID NO |
|---|---|---|
| 7502mTU | Fwd: CATCAGCACTGGCCTACTACA | 17 |
| | Probe (BHQ): AAGCTGAGGCCTACAGA CACTCCC | 18 |
| | Rev: AGGCAGCCACCCAACAGTTAC | 19 |
| 7502mTD | Fwd: TGACCAGAGGGACATAGAACTCC | 20 |
| | Probe (BHQ): TCACCCAAGCAGCAAGA GACTATTGTA | 21 |
| | Rev: TCCCAACATGGTGGCTAGTTT | 22 |
| 7502hTU | Fwd: GCCAGGCCTACCAACCTA | 23 |
| | Probe (BHQ): TGATGAGTTTGAGTTTC CCATTGGGACA | 24 |
| | Rev: CAGGGCGGCATTCATAGTTCAG | 25 |

TABLE 3-continued

Primer and Probes in Mouse Taqman LOA Assays (7502mTU and 7502mTD), Human Taqman GOA Assays (7502hTU and 7502hTD), Mouse Promoter Assays (7502mPU and 7502mPU2), and Mouse Retention Assays (7502mretU and 7502retD)

| Description | Sequence | SEQ ID NO |
|---|---|---|
| 7502hTD | Fwd: TCTCGTGCACATGATGCTC | 26 |
| | Probe (BHQ): TCATAGTTGGCACTTTATCTGGTACGATC | 27 |
| | Rev: ACGCTGCTGCCTCCTTGAG | 28 |
| 7502mPU | Fwd: AGCTGGGTGGGTTAGTGGAGAA | 29 |
| | Probe (BHQ): AGTGCTAGCTGTTGGTCCAGCA | 30 |
| | Rev: TGCCGCTTGCCTTTGTAAG | 31 |
| 7502mPU2 | Fwd: TCTGCGCCATGTTTGACTTTG | 32 |
| | Probe (BHQ): TGGCTTCTACTAGGCACACGACGG | 33 |
| | Rev: GGTGCTGCATACTTCCTCTCTA | 34 |
| 7502mretU | Fwd: GGAAGGGAAGAGCAACAACAC | 35 |
| | Probe (BHQ): TCTTGGACACCTTGAAGACGGAGC | 36 |
| | Rev: CCAGCGTCAGGAGGTCTG | 37 |
| 7502mretD | Fwd: GGCCTGTCAGCCATCTTATGC | 38 |
| | Probe (BHQ): TTTCCTGGACCTCTGCTGGGATCG | 39 |
| | Rev: TGGTGCTGCTGGTGGTAG | 40 |

Transgenic ESC clones were microinjected into 8-cell Swiss Webster embryos, resulting in F0 VelociMice® fully derived from the injected modified ESC (Poueymirou 2007). These F0 mice were subsequently bred to homozygosity on a 100% C57B1/6NTac background, which were designated as MAID7502. The resistance cassette was removed by self-deleting technology, thereby generating strain MAID7503. Subsequent analysis using targeted locus amplification (TLA; Cergentis) determined that the transgene was present as a single copy on the X chromosome, but not targeted into the endogenous Gata1 locus. All animals were maintained in the Regeneron Animal Facility during the entire study period.

Figure 5A:
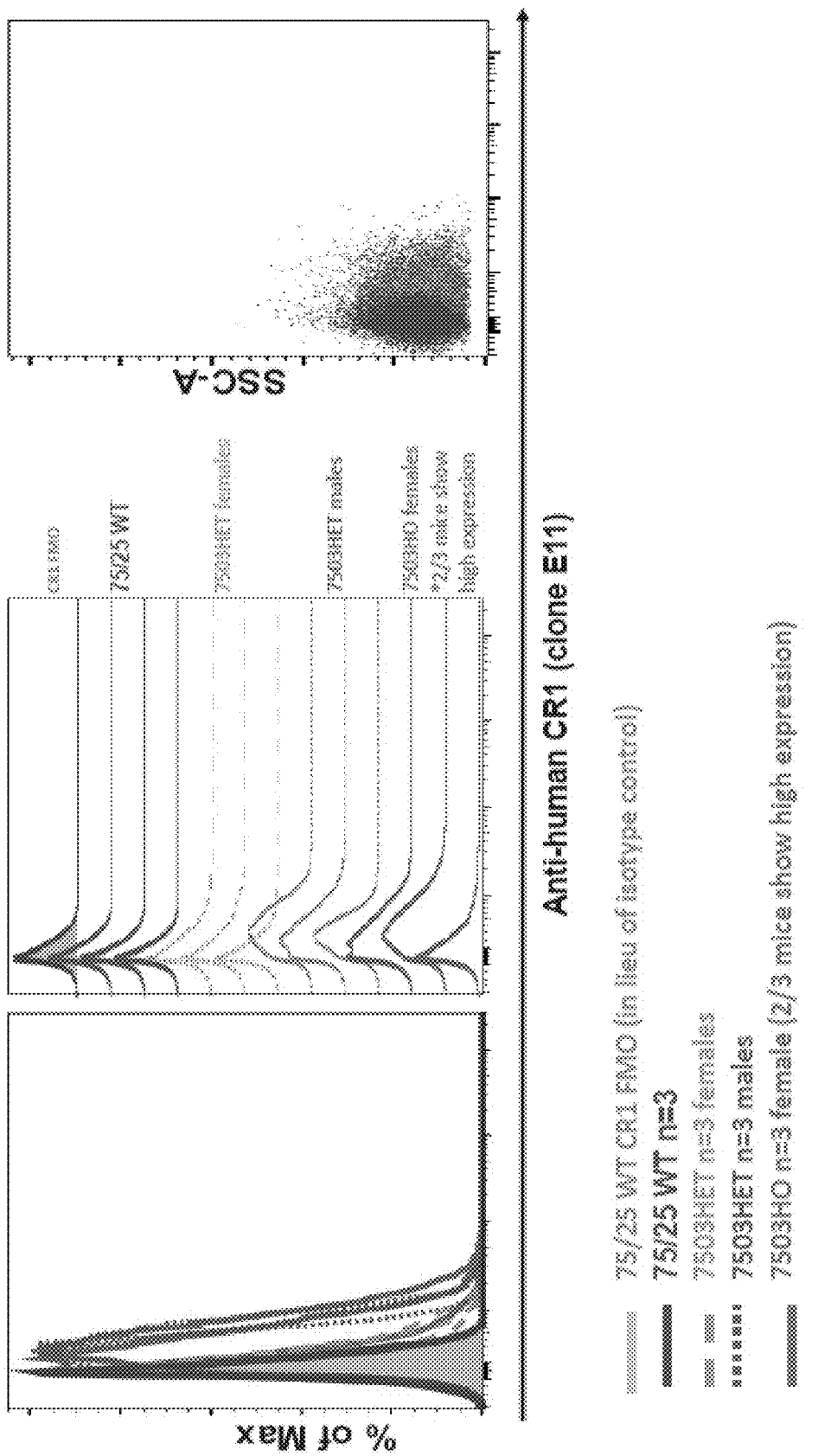
FIG. 5A shows the levels of human CR1 on peripheral blood RBCs from 75/25 WT, 7503HET females, 7503HET males, and 7503HO females. MAID7503 HET male and HO female mice show a similar level of hCR1 expression (higher than found in 7503HET females) in comparison to CR1 FMO control (in lieu of an isotype control). All plots gated on Ter119+ mouse RBCs.
Figure 5B:
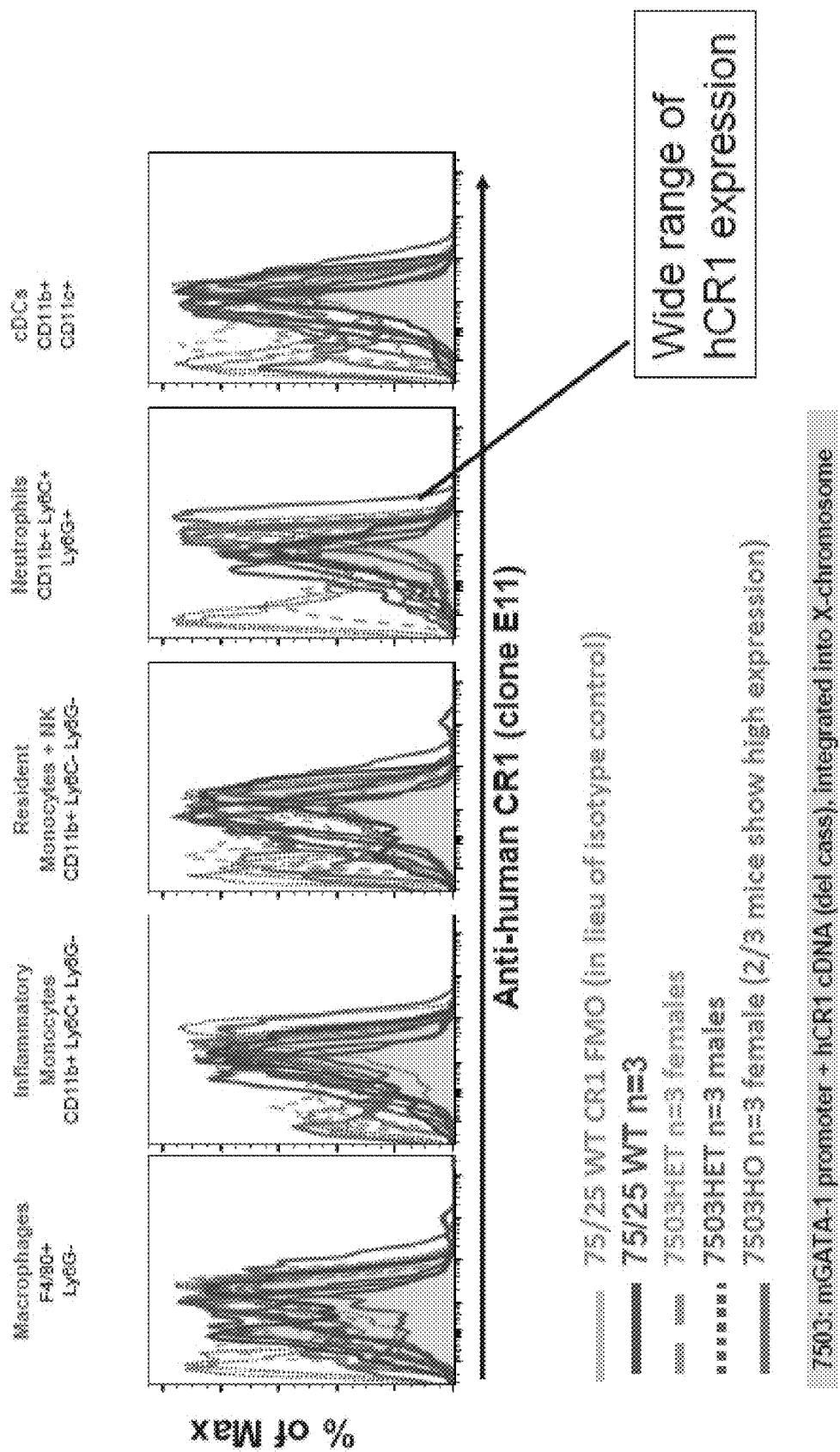
FIG. 5B shows the levels of human CR1 on cell populations from lysed blood of 75/25 WT, 7503HET females, 7503HET males, and 7503HO females in comparison to CR1 FMO control (in lieu of an isotype control). MAID7503 HET male and HO female mice show some hCR1 expression (higher than found in 7503HET females).
Figure 5C:
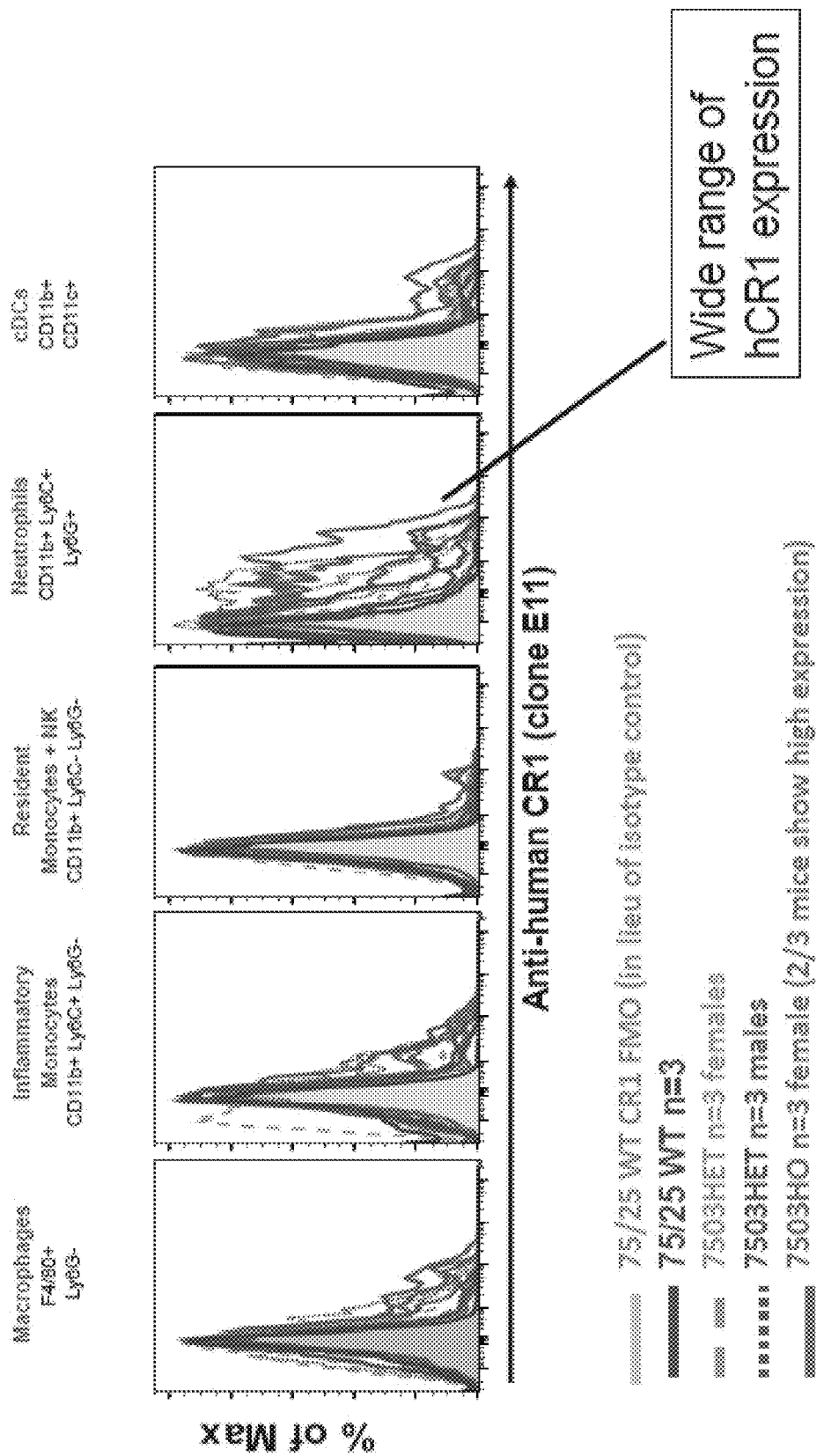
FIG. 5C shows the levels of human CR1 on cell populations from the spleen of 75/25 WT, 7503HET females, 7503HET males, and 7503HO females in comparison to CR1 FMO control (in lieu of an isotype control). MAID7503 HET male and HO female mice show some hCR1 expression (higher than found in 7503HET females).
Figure 5D:
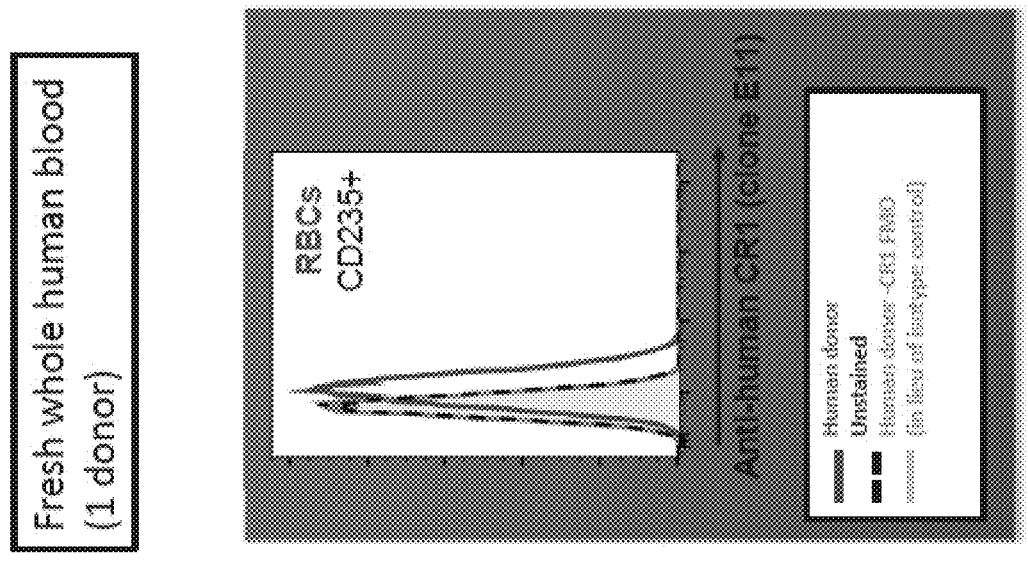
FIG. 5D demonstrates human CR1 expression on human peripheral blood RBCs, neutrophils and monocytes express CR1, in comparison to CR1 FMO control (in lieu of an isotype control).
Figure 5D:
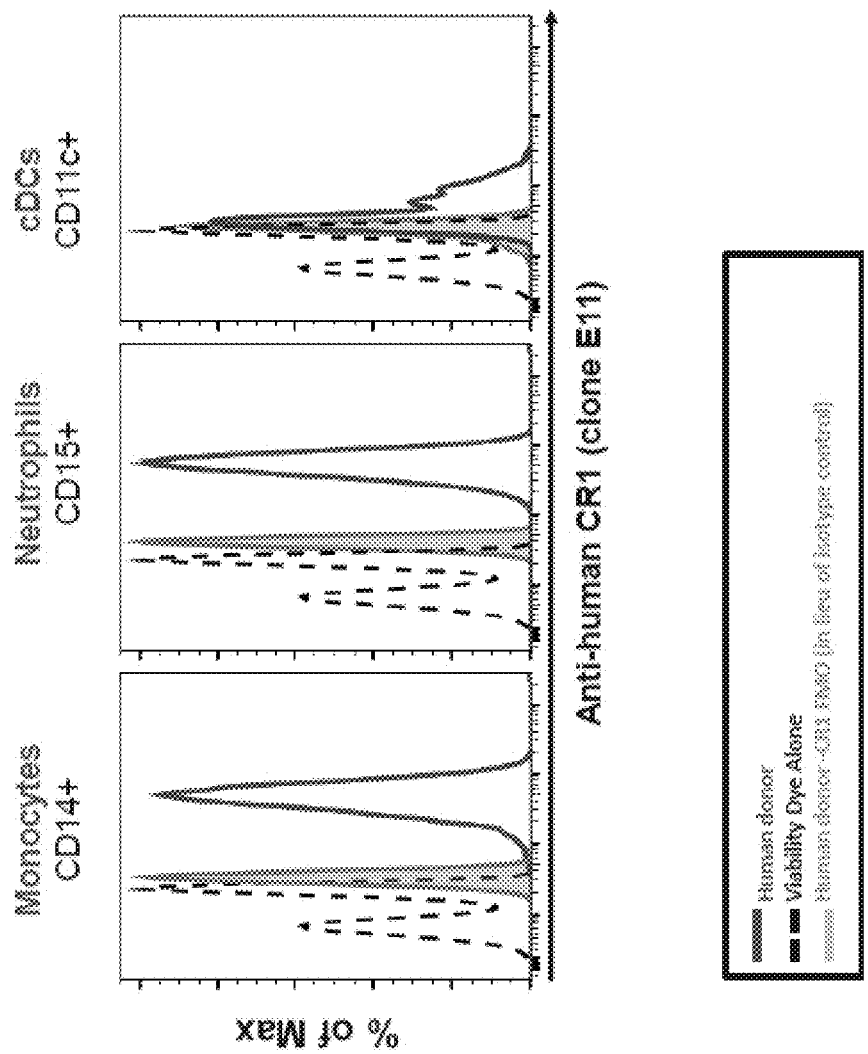
Figure 5E:
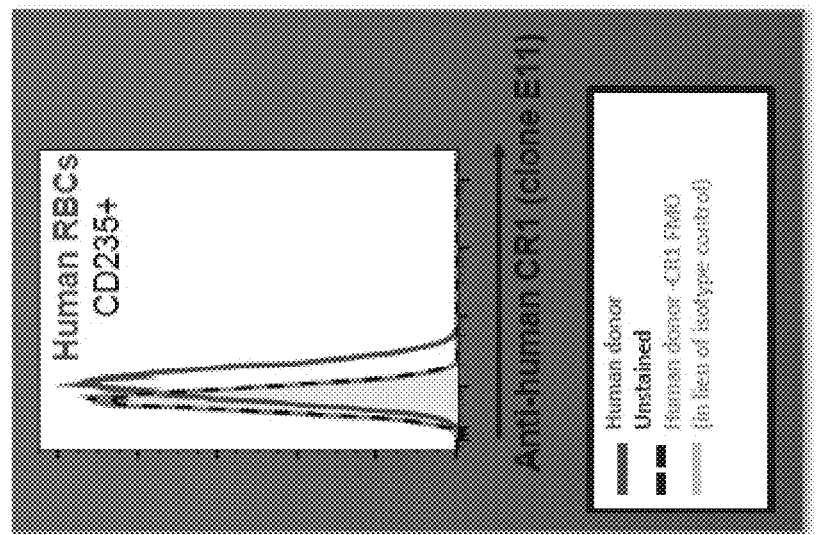
FIG. 5E shows the levels of human CR1 on peripheral blood RBCs from 75/25 WT, B6.Cg-Tg(Gata1-CR1)1Rwf/J females, 7503HO females, in comparison to CR1 FMO control (in lieu of an isotype control). RBCs show a similar level of hCR1 expression compared to human RBCs (and similar to MAID7503 HO RBCs).
Figure 5E:
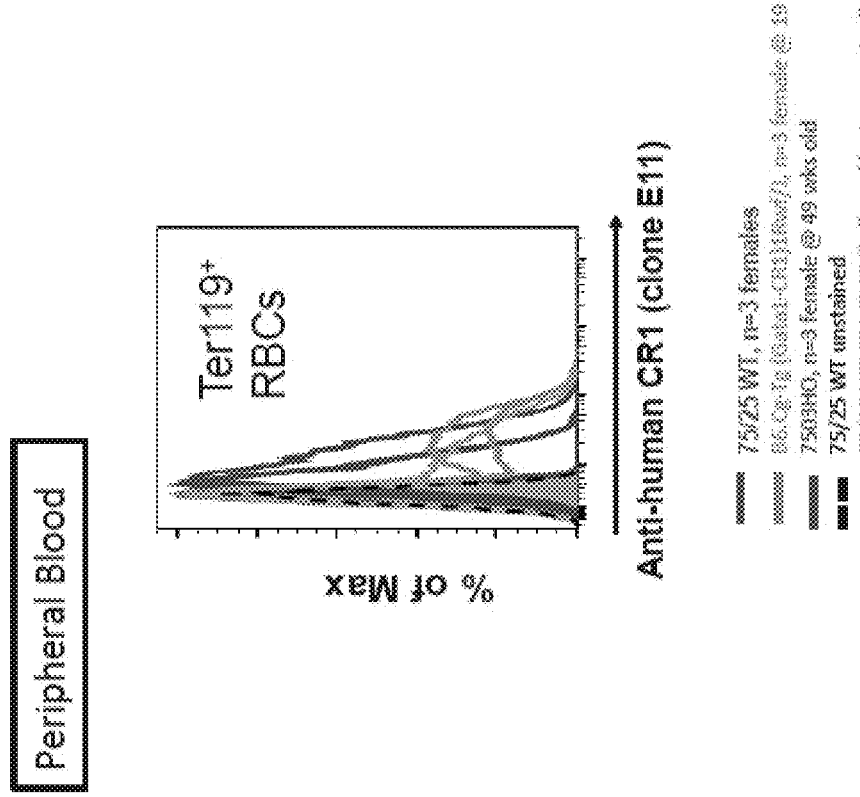
Figure 5F:
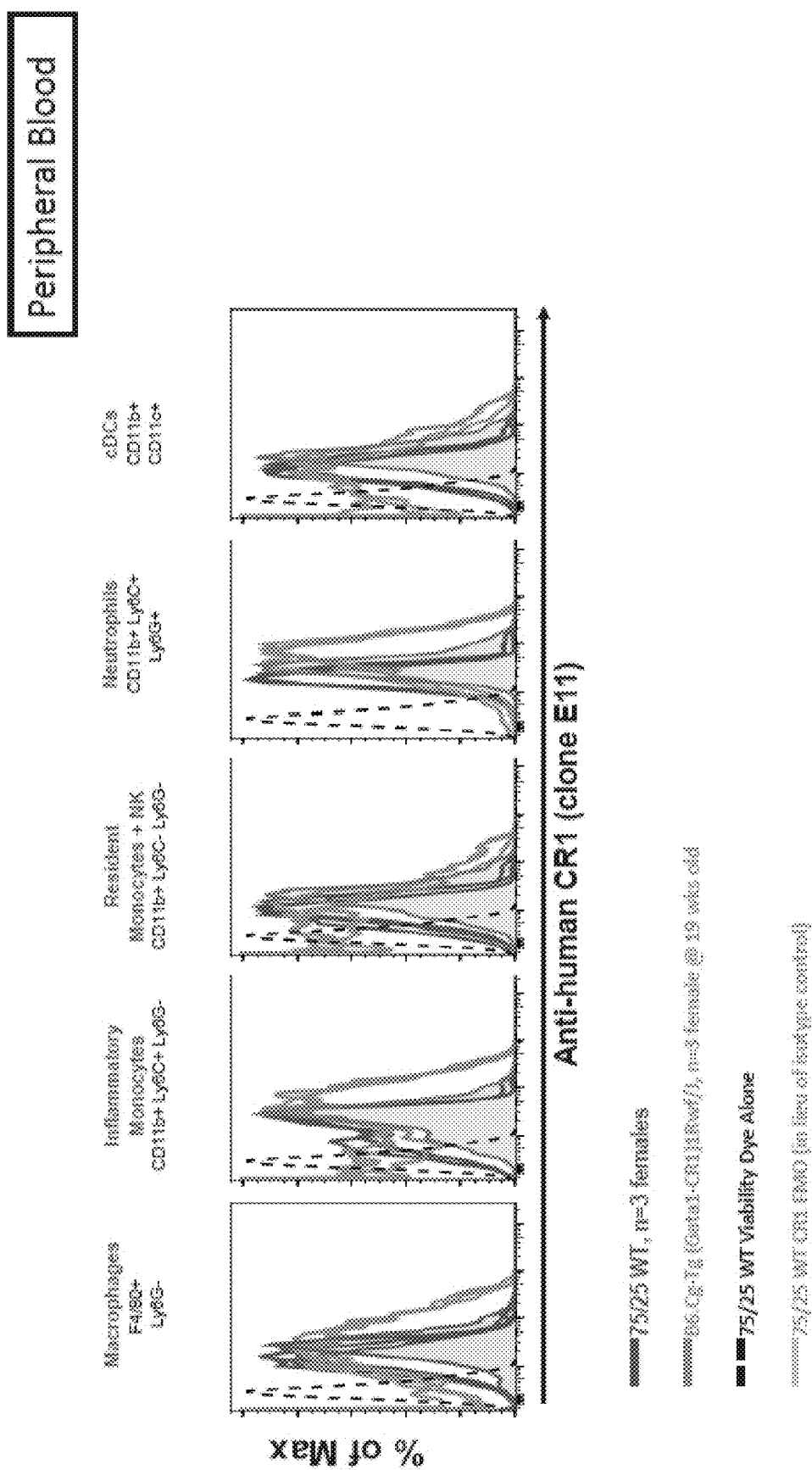
FIG. 5F shows the levels of human CR1 on cell populations in peripheral blood from 75/25 WT, B6.Cg-Tg(Gata1-CR1)1Rwf/J females, 7503HO females, in comparison to CR1 FMO control (in lieu of an isotype control). B6.Cg-Tg (Gata1-CR1)1Rwf/J blood neutrophils express very low levels of hCR1, in contrast to human blood neutrophils and monocytes.

Example 5. Phenotyping of Mouse Comprising Transgenic Human CRI Driven by a mouse GATA-1 Promoter Flow cytometry was performed on cells from the blood and spleen of MAID 7503 mice and the results are shown in FIGS. 5A-5C. RBCs from MAID7503 HET male and HO female mice showed a similar level of hCR1 expression (higher than found in 7503HET females (FIG. 5A). MAID7503 HET male and HO female mice showed some hCR1 expression (higher than found in 7503HET females) for both blood and splenic cell populations (FIGS. 5B-5C). In summary, hCR1 expression was best observed on surface of RBCs in MAID7503 HET males and 7503HO female mice. Unlike human blood leukocytes, hCR1 was weakly expressed in mouse blood and splenic monocytes/neutrophils (large variability) in MAID7503 HET male/female and HO mice.

hCR1 expression on RBCs and blood/spleen leukocytes was also examined in B6.Cg-Tg(Gata1-CR1)1Rwf/J mice (Jackson Labs, generated by Robert W. Finberg, University of Massachusetts, as described in Repik et al., *Clinical and Experimental Immunology* 140: 230-240, 2005) and human blood. hCR1 expression was observed on surface of RBCs in both B6.Cg-Tg(Gata1-CR1)1Rwf/J (Jackson Labs) and MAID7503 HO mice (FIG. 5E). Unlike in human blood leukocytes (FIG. 5D), hCR1 was very poorly expressed in mouse blood monocytes/neutrophils in B6.Cg-Tg(Gata1-CR1)1Rwf/J mice (FIG. 5F). hCR1 expression in blood monocytes/neutrophils was previously observed in MAID7503 HO mice (see FIG. 5B). No hCR1 expression was observed in splenic monocytes/neutrophils in either mouse strain.

What is claimed is:

1. A genetically modified rodent animal comprising in its genome a nucleic acid which comprises a genomic DNA of a human CR1 gene encoding a human CR1 polypeptide, wherein the genomic DNA of the human CRI gene comprises:
   (i) the coding sequence from ATG to STOP;
   (ii) the 5' untranslated region (UTR), the 3' UTR, and intervening introns;
   (iii) a 5' upstream sequence of at least 4000 bp directly upstream of the 5' UTR; and
   (iv) a sequence of at least 150 bp directly downstream of the 3' UTR;
   wherein the nucleic acid is inserted downstream of the 3' UTR of a rodent Cr2 gene and upstream to the 5' UTR of a rodent Cr1 like (Cr1l) gene;
   wherein the rodent animal expresses the human CRI polypeptide; and
   wherein the rodent animal is a mouse or a rat.

2. The rodent animal of claim 1, wherein the rodent animal is a male.

3. The rodent animal of claim 1, wherein the rodent animal is a female.

4. The rodent animal of claim 1, wherein the rodent animal is heterozygous for the nucleic acid.

5. The rodent animal of claim 1, wherein the rodent animal is homozygous for the nucleic acid.

6. The rodent animal of claim 1, further comprising in its genome a replacement of a rodent C3 gene sequence at an endogenous rodent C3 locus with a human C3 gene sequence to form a modified C3 gene, wherein the modified C3 gene comprises an exon of the endogenous rodent C3 gene and the human C3 gene sequence comprises exon 2 through exon 41, or exon 1 through exon 41, of the human C3 gene.

7. A cell or tissue isolated from a rodent of claim 1, whose genome comprises the nucleic acid comprising a nucleotide sequence encoding a human CR1 polypeptide, wherein optionally the cell is an egg.

8. A rodent embryonic stem (ES) cell, comprising in its genome a nucleic acid which comprises a genomic DNA of a human CRI gene encoding a human CR1 polypeptide, wherein the genomic DNA of the human CRI gene comprises:
   (i) the coding sequence from ATG to STOP;
   (ii) the 5' UTR, the 3'UTR, and intervening introns;
   (iii) a 5' upstream sequence of at least 4000 bp directly upstream of the 5' UTR; and
   (iv) a sequence of at least 150 bp directly downstream of the 3' UTR;
   wherein the nucleic acid is inserted downstream of the 3' UTR of a rodent Cr2 gene locus and upstream to the 5UTR of a rodent Cr1 like (Cr1l) gene.

9. A method of making a genetically modified rodent animal which is a mouse or a rat, comprising:
   a) inserting a nucleic acid into the genome of a rodent ES cell, wherein the nucleic acid comprises a genomic DNA of a human CRI gene encoding a human CR1 polypeptide, wherein the genomic DNA of the human CRI gene comprises:
   (i) the coding sequence from ATG to STOP;
   (ii) the 5' UTR, the 3' UTR, and intervening introns;
   (iii) a 5' upstream sequence of at least 4000 bp directly upstream of the 5' UTR; and
   (iv) a sequence of at least 150 bp directly downstream of the 3' UTR;
   wherein the nucleic acid is inserted downstream of the 3' UTR of a rodent Cr2 gene and upstream to the 5' UTR of a rodent Cr1 like (Cr1l) gene; and
   b) making a genetically modified rodent animal using a rodent ES cell obtained from step a)
   wherein the rodent animal expresses the human CR1 polypeptide; and
   wherein the rodent animal is a mouse or a rat.

* * * * *

SEQUENCE LISTING

<160> NUMBER OF SEQ ID NOS: 41

<210> SEQ ID NO 1
<211> LENGTH: 8587
<212> TYPE: DNA
<213> ORGANISM: Homo sapiens

<400> SEQUENCE: 1

```
acactctggg cgcggagcac aatgattggt cactcctatt ttcgctgagc ttttcctctt     60
atttcagttt tcttcgagat caaatctggt ttgtagatgt gcttggggag aatgggggcc    120
tcttctccaa gaagcccgga gcctgtcggg ccgccggcgc ccggtctccc cttctgctgc    180
ggaggatccc tgctggcggt tgtggtgctg cttgcgctgc cggtggcctg gggtcaatgc    240 aatgcccag aatggcttcc atttgccagg cctaccaacc taactgatga atttgagttt    300
cccattggga catatctgaa ctatgaatgc cgccctggtt attccggaag accgttttct    360
atcatctgcc taaaaaactc agtctggact ggtgctaagg acaggtgcag acgtaaatca    420
tgtcgtaatc ctccagatcc tgtgaatggc atggtgcatg tgatcaaagg catccagttc    480
ggatcccaaa ttaaatattc ttgtactaaa ggataccgac tcattggttc ctcgtctgcc    540
acatgcatca tctcaggtga tactgtcatt tgggataatg aaacacctat ttgtgacaga    600
```

```
attccttgtg ggctaccccc caccatcacc aatggagatt tcattagcac caacagagag    660
aattttcact atggatcagt ggtgacctac cgctgcaatc ctggaagcgg agggagaaag    720
gtgtttgagc ttgtgggtga gccctccata tactgcacca gcaatgacga tcaagtgggc    780
atctggagcg gccccgcccc tcagtgcatt atacctaaca aatgcacgcc tccaaatgtg    840
gaaaatggaa tattggtatc tgacaacaga agcttatttt ccttaaatga agttgtggag    900
tttaggtgtc agcctggctt tgtcatgaaa ggaccccgcc gtgtgaagtg ccaggccctg    960
aacaaatggg agccggagct accaagctgc tccagggtat gtcagccacc tccagatgtc   1020
ctgcatgctg agcgtaccca aagggacaag gacaacttttt cacctgggca ggaagtgttc   1080
tacagctgtg agcccggcta cgacctcaga ggggctgcgt ctatgcgctg cacaccccag   1140
ggagactgga gccctgcagc ccccacatgt gaagtgaaat cctgtgatga cttcatgggc   1200
caacttctta atggccgtgt gctatttcca gtaaatctcc agcttggagc aaaagtggat   1260
tttgtttgtg atgaaggatt tcaattaaaa ggcagctctg ctagttactg tgtcttggct   1320
ggaatggaaa gcctttggaa tagcagtgtt ccagtgtgtg aacaaatctt ttgtccaagt   1380
cctccagtta ttcctaatgg agacacaca ggaaaacctc tggaagtctt tcccttggg    1440 aaaacagtaa attacacatg cgacccccac ccagacagag gacgagctt cgacctcatt   1500 ggagagagca ccatccgctg cacaagtgac cctcaaggga tggggtttg gagcagccct   1560 gcccctcgct gtggaattct gggtcactgt caagccccag atcattttct gtttgccaag   1620
ttgaaaaccc aaaccaatgc atctgactttt cccattggga catctttaaa gtacgaatgc   1680
cgtcctgagt actacgggag gccattctct atcacatgtc tagataacct ggtctggtca   1740
agtcccaaag atgtctgtaa acgtaaatca tgtaaaactc ctccagatcc agtgaatggc   1800
atggtgcatg tgatcacaga catccaggtt ggatccagaa tcaactattc ttgtactaca   1860
gggcaccgac tcattggtca ctcatctgct gaatgtatcc tctcgggcaa tgctgcccat   1920
tggagcacga agccgccaat tgtcaacga attccttgtg ggctaccccc caccatcgcc   1980
aatggagatt tcattagcac caacagagag aattttcact atggatcagt ggtgacctac   2040
cgctgcaatc ctggaagcgg agggagaaag gtgtttgagc ttgtgggtga gccctccata   2100
tactgcacca gcaatgacga tcaagtgggc atctggagcg gcccggcccc tcagtgcatt   2160
atacctaaca aatgcacgcc tccaaatgtg gaaaatggaa tattggtatc tgacaacaga   2220
agcttatttt ccttaaatga agttgtggag tttaggtgtc agcctggctt tgtcatgaaa   2280
ggaccccgcc gtgtgaagtg ccaggccctg aacaaatggg agccggagct accaagctgc   2340
tccagggtat gtcagccacc tccagatgtc ctgcatgctg agcgtaccca aagggacaag   2400 gacaacttttt cacccgggca ggaagtgttc tacagctgtg agcccggcta tgacctcaga   2460
ggggctgcgt ctatgcgctg cacaccccag ggagactgga gccctgcagc ccccacatgt   2520
gaagtgaaat cctgtgatga cttcatgggc caacttctta atggccgtgt gctatttcca   2580
gtaaatctcc agcttggagc aaaagtggat tttgtttgtg atgaaggatt tcaattaaaa   2640
ggcagctctg ctagttattg tgtcttggct ggaatggaaa gcctttggaa tagcagtgtt   2700
ccagtgtgtg aacaaatctt ttgtccaagt cctccagtta ttcctaatgg agacacaca   2760 ggaaaacctc tggaagtctt tcccttggga aaagcagtaa attacacatg cgacccccac   2820
ccagacagag gacgagctt cgacctcatt ggagagagca ccatccgctg cacaagtgac   2880
cctcaaggga tggggtttg gagcagccct gcccctcgct gtggaattct gggtcactgt   2940
caagccccag atcattttct gtttgccaag ttgaaaaccc aaaccaatgc atctgactttt   3000
```

```
cccattggga catctttaaa gtacgaatgc cgtcctgagt actacgggag gccattctct    3060
atcacatgtc tagataacct ggtctggtca agtcccaaag atgtctgtaa acgtaaatca    3120
tgtaaaactc ctccagatcc agtgaatggc atggtgcatg tgatcacaga catccaggtt    3180
ggatccagaa tcaactattc ttgtactaca gggcaccgac tcattggtca ctcatctgct    3240
gaatgtatcc tctcaggcaa tactgcccat ggagcacga agccgccaat tgtcaacga      3300 attccttgtg ggctaccccc aaccatcgcc aatggagatt tcattagcac caacagagag    3360
aattttcact atggatcagt ggtgacctac cgctgcaatc ttggaagcag agggagaaag    3420
gtgtttgagc ttgtgggtga gccctccata tactgcacca gcaatgacga tcaagtgggc    3480
atctggagcg gccccgcccc tcagtgcatt atacctaaca aatgcacgcc tccaaatgtg    3540
gaaaatggaa tattggtatc tgacaacaga agcttatttt ccttaaatga agttgtggag    3600
tttaggtgtc agcctggctt tgtcatgaaa ggaccccgcc gtgtgaagtg ccaggccctg    3660
aacaaatggg agccagagtt accaagctgc tccagggtgt gtcagccgcc tccagaaatc    3720
ctgcatggtg agcatacccc aagccatcag acaacttttc acctgggca ggaagtgttc      3780 tacagctgtg agcctggcta tgacctcaga ggggctgcgt tctgcactg cacaccccag      3840 ggagactgga gccctgaagc cccgagatgt gcagtgaaat cctgtgatga cttcttgggt    3900
caactccctc atggccgtgt gctatttcca cttaatctcc agcttggggc aaaggtgtcc    3960
tttgtctgtg atgaagggtt tcgcttaaag ggcagttccg ttagtcattg tgtcttggtt    4020
ggaatgagaa gcctttggaa taacagtgtt cctgtgtgtg aacatatctt ttgtccaaat    4080
cctccagcta tccttaatgg gagacacaca ggaactccct ctggagatat tccctatgga    4140
aaagaaatat cttacacatg tgaccccac ccagacagag ggatgacctt caacctcatt      4200
ggggagagca ccatccgctg cacaagtgac cctcatggga atggggtttg gagcagccct    4260
gcccctcgct gtgaactttc tgttcgtgct ggtcactgta aaaccccaga gcagtttcca    4320
tttgccagtc ctacgatccc aattaatgac tttgagtttc cagtcgggac atctttgaat    4380
tatgaatgcc gtcctgggta tttgggaaaa atgttctcta tctcctgcct agaaaacttg    4440
gtctggtcaa gtgttgaaga caactgtaga cgaaaatcat gtggacctcc accagaaccc    4500
ttcaatggaa tggtgcatat aaacacagat acacagtttg gatcaacagt taattattct    4560
tgtaatgaag ggtttcgact cattggttcc ccatctacta cttgtctcgt ctcaggcaat    4620
aatgtcacat gggataagaa ggcaccttatt tgtgagatca tatcttgtga gccacctcca    4680
accatatcca atggagactt ctacagcaac aatagaacat ctttcacaa tggaacggtg      4740 gtaacttacc agtgccacac tggaccagat ggagaacagc tgtttgagct tgtgggagaa    4800
cggtcaatat attgcaccag caaagatgat caagttggtg tttggagcag ccctcccccct    4860 cggtgtattt ctactaataa atgcacagct ccagaagttg aaaatgcaat tagagtacca    4920
ggaaacagga gtttctttac cctcactgag atcatcagat ttagatgtca gcccgggttt    4980
gtcatggtag ggtcccacac tgtgcagtgc cagaccaatg gcagatgggg gcccaagctg    5040
ccacactgct ccagggtgtg tcagccgcct ccagaaatcc tgcatggtga gcataccta     5100 agccatcagg acaacttttc acctgggcag gaagtgttct acagctgtga gcccagctat    5160
gacctcagag gggctgcgtc tctgcactgc acgccccagg gagactggag ccctgaagcc    5220
cctagatgta cagtgaaatc ctgtgatgac ttcctgggcc aactccctca tggccgtgtg    5280
ctacttccac ttaatctcca gcttggggca aaggtgtcct ttgtttgcga tgaagggttc    5340
```

```
cgattaaaag gcaggtctgc tagtcattgt gtcttggctg gaatgaaagc cctttggaat    5400
agcagtgttc cagtgtgtga acaaatcttt tgtccaaatc ctccagctat ccttaatggg    5460
agacacacag gaactccctt tggagatatt ccctatggaa agaaatatc ttacgcatgc    5520 gacacccacc cagacagagg gatgaccttc aacctcattg gggagagctc catccgctgc    5580
acaagtgacc ctcaagggaa tggggtttgg agcagccctg cccctcgctg tgaactttct    5640
gttcctgctg cctgcccaca tccacccaag atccaaaacg ggcattacat tggaggacac    5700
gtatctctat atcttcctgg gatgacaatc agctacattt gtgaccccgg ctacctgtta    5760
gtgggaaagg gcttcatttt ctgtacagac cagggaatct ggagccaatt ggatcattat    5820
tgcaaagaag taaattgtag cttcccactg tttatgaatg gaatctcgaa ggagttagaa    5880
atgaaaaaag tatatcacta tggagattat gtgactttga agtgtgaaga tgggtatact    5940
ctggaaggca gtccctggag ccagtgccag gcggatgaca gatgggaccc tcctctggcc    6000
aaatgtacct ctcgtacaca tgatgctctc atagttggca ctttatctgg tacgatcttc    6060 tttatttac tcatcatttt cctctcttgg ataattctaa agcacagaaa aggcaataat    6120
gcacatgaaa accctaaaga agtggctatc catttacatt ctcaaggagg cagcagcgtt    6180
catccccgaa ctctgcaaac aaatgaagaa atagcaggg tccttccttg acaaagtact    6240
atacagctga agaacatctc gaatacaatt ttggtgggaa aggagccaat tgatttcaac    6300
agaatcagat ctgagcttca taaagtcttt gaagtgactt cacagagacg cagacatgtg    6360
cacttgaaga tgctgcccct tccctggtac ctagcaaagc tcctgcctct ttgtgtgcgt    6420
cactgtgaaa ccccccaccct tctgcctcgt gctaaacgca cacagtatct agtcagggga    6480
aaagactgca tttaggagat agaaaatagt ttggattact taaggaata aggtgttgcc    6540 tggaatttct ggtttgtaag gtggtcactg ttcttttta aaatatttgt aatatggaat    6600
gggctcagta agaagagctt ggaaaatgca gaaagttatg aaaaataagt cacttataat    6660
tatgctacct actgataacc actcctaata ttttgattca ttttctgcct atcttctttc    6720
acatatgtgt ttttttacat acgtactttt ccccctttagt ttgtttcctt ttattttata    6780
gagcagaacc ctagtctttt aaacagttta gagtgaaata tatgctatat cagttttta    6840 tttctctagg gagaaaaatt aatttactag aaaggcatga aatgatcatg ggaagagtgg    6900
ttaagactac tgaagagaaa tatttggaaa ataagatttc gatatcttct ttttttttga    6960
gatggagtct ggctctgtct cccaggctgg agtgcagtgg cgtaatctcg gctcactgca    7020
agctccgcct cccggggttga caccatttc ctgcctcagc ctcctgagta gttgggatta    7080
ccagtagatg ggactacagg cacctgccaa cacgcccggc taatttttt gtatttttag    7140 tagagacggg gtttcaccat gttagccagg atggtctgga tctcctgacc tcgtgatcca    7200
cctgcctcgg cctcccaaag tgctgcgatt acaggcatga gccaccgcgc ctggccgctt    7260
tcgatatttt ctaaacttta attcaaaagc actttgtgct gtgttctata taaaaaacat    7320
aataaaaatt gaaatgaaag aataattgtt attataaaag tactagctta cttttgtatg    7380
gattcagaat atactaaatt aactttttaa aacacaactt ttaaaaaatg tatcaaaata    7440
ataaacgtgt tctgatattt ttaaaataag tgaccttgtg ttctttaacc agtccacatc    7500
tttagagaac aaaaatgtgt tatgatatta tgggccatgc taatgacctc tagaaaacat    7560
cagaatattt ctggatattt aataatagct ttatatatga ctaatgctca tttctatgta    7620
attctgttta atagttgctt taaaggtgaa ttttgccaca tttactttga cagcagtata    7680
aggagtgaga tagacatgaa cctgaatttc aatttaaaat catggaagag agggaaaaaa    7740
```

```
aaccagctta agaaaaatca actgataaac tgcaagaaaa aaatgcaact tacatcacaa    7800
aagctaattg ctttattatt tagagagtac ttaaaaatta aagaccaaac ttctctccac    7860
ccaacaaaaa tgggcaaagg acatacagct aggtcaccaa gaaagaaggg caaataggtg    7920
gtgagtatat gtaaagatac ttgataggac ttttgcttag ttgaatcttt agcaaatctc    7980
ttttatttct tgggattttg aagaagtaat ttttaaagga ggactagaaa ctaagtgatt    8040
gggaattggc cttttttagaa ttaaaatttc ccattacaag aaaaaaaaat cctgtgttct    8100 ttttttttc cagaatggag taggtcagtg agcaatgtga ttaataaata tttcaatgtc     8160
tgtgactttt gatttatttt ggagacaggg tcttgctctg ttacccaggc tggagtgcag    8220
tggtgctatc taggcttact gcaacctcac ctgtcacttt ttaattgcaa gaaagctgaa    8280
aggttttttt ctattatatc agttataatg ataaatactg tatatactaa ctatgagtaa    8340
aatactatat tgcctaactt gtattattaa gcaattctgc taacctgtga ccttacattt    8400
tcatctgaaa agcaggggct ggacaccaat tgccctatga agctattgct agtcctaaca    8460
ttctttgttt tgtttgcttt tttggcacac ttaagtgtgt actatgaagt ttatgatgct    8520
ttaatgaaat tttctgtctc taccattgta atgagaaagg aataaaatac tttattttgc    8580
aaatcta                                                              8587

<210> SEQ ID NO 2
<211> LENGTH: 2039
<212> TYPE: PRT
<213> ORGANISM: Homo sapiens

<400> SEQUENCE: 2

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
        195                 200                 205

Gly Glu Pro Ser Ile Tyr Cys Thr Ser Asn Asp Asp Gln Val Gly Ile
```

```
                  210                 215                 220
Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                    245                 250                 255

Ser Leu Asn Glu Val Val Glu Phe Arg Cys Gln Pro Gly Phe Val Met
                260                 265                 270

Lys Gly Pro Arg Arg Val Lys Cys Gln Ala Leu Asn Lys Trp Glu Pro
            275                 280                 285

Glu Leu Pro Ser Cys Ser Arg Val Cys Gln Pro Pro Pro Asp Val Leu
        290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                    325                 330                 335

Ser Met Arg Cys Thr Pro Gln Gly Asp Trp Ser Pro Ala Ala Pro Thr
                340                 345                 350

Cys Glu Val Lys Ser Cys Asp Asp Phe Met Gly Gln Leu Leu Asn Gly
            355                 360                 365

Arg Val Leu Phe Pro Val Asn Leu Gln Leu Gly Ala Lys Val Asp Phe
        370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                    405                 410                 415

Glu Gln Ile Phe Cys Pro Ser Pro Pro Val Ile Pro Asn Gly Arg His
                420                 425                 430

Thr Gly Lys Pro Leu Glu Val Phe Pro Phe Gly Lys Thr Val Asn Tyr
            435                 440                 445

Thr Cys Asp Pro His Pro Asp Arg Gly Thr Ser Phe Asp Leu Ile Gly
        450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                    485                 490                 495

Asp His Phe Leu Phe Ala Lys Leu Lys Thr Gln Thr Asn Ala Ser Asp
                500                 505                 510

Phe Pro Ile Gly Thr Ser Leu Lys Tyr Glu Cys Arg Pro Glu Tyr Tyr
            515                 520                 525

Gly Arg Pro Phe Ser Ile Thr Cys Leu Asp Asn Leu Val Trp Ser Ser
        530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                    565                 570                 575

Ile Asn Tyr Ser Cys Thr Thr Gly His Arg Leu Ile Gly His Ser Ser
                580                 585                 590

Ala Glu Cys Ile Leu Ser Gly Asn Ala Ala His Trp Ser Thr Lys Pro
            595                 600                 605

Pro Ile Cys Gln Arg Ile Pro Cys Gly Leu Pro Pro Thr Ile Ala Asn
        610                 615                 620

Gly Asp Phe Ile Ser Thr Asn Arg Glu Asn Phe His Tyr Gly Ser Val
625                 630                 635                 640
```

-continued

Val Thr Tyr Arg Cys Asn Pro Gly Ser Gly Arg Lys Val Phe Glu
                645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
        675                 680                 685

Thr Pro Pro Asn Val Glu Asn Gly Ile Leu Val Ser Asp Asn Arg Ser
    690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
        755                 760                 765

Gly Gln Glu Val Phe Tyr Ser Cys Glu Pro Gly Tyr Asp Leu Arg Gly
    770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
                805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
        835                 840                 845

Tyr Cys Val Leu Ala Gly Met Glu Ser Leu Trp Asn Ser Ser Val Pro
    850                 855                 860

Val Cys Glu Gln Ile Phe Cys Pro Ser Pro Pro Val Ile Pro Asn Gly
865                 870                 875                 880

Arg His Thr Gly Lys Pro Leu Glu Val Phe Pro Phe Gly Lys Ala Val
                885                 890                 895

Asn Tyr Thr Cys Asp Pro His Pro Asp Arg Gly Thr Ser Phe Asp Leu
            900                 905                 910

Ile Gly Glu Ser Thr Ile Arg Cys Thr Ser Asp Pro Gln Gly Asn Gly
        915                 920                 925

Val Trp Ser Ser Pro Ala Pro Arg Cys Gly Ile Leu Gly His Cys Gln
930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
                965                 970                 975

Tyr Tyr Gly Arg Pro Phe Ser Ile Thr Cys Leu Asp Asn Leu Val Trp
            980                 985                 990

Ser Ser Pro Lys Asp Val Cys Lys Arg Lys Ser Cys Lys Thr Pro Pro
        995                 1000                1005

Asp Pro Val Asn Gly Met Val His Val Ile Thr Asp Ile Gln Val
    1010                1015                1020

Gly Ser Arg Ile Asn Tyr Ser Cys Thr Thr Gly His Arg Leu Ile
    1025                1030                1035

Gly His Ser Ser Ala Glu Cys Ile Leu Ser Gly Asn Thr Ala His
    1040                1045                1050

```
Trp Ser Thr Lys Pro Pro Ile Cys Gln Arg Ile Pro Cys Gly Leu
    1055            1060                1065

Pro Pro Thr Ile Ala Asn Gly Asp Phe Ile Ser Thr Asn Arg Glu
    1070            1075                1080

Asn Phe His Tyr Gly Ser Val Val Thr Tyr Arg Cys Asn Leu Gly
    1085            1090                1095

Ser Arg Gly Arg Lys Val Phe Glu Leu Val Gly Glu Pro Ser Ile
    1100            1105                1110

Tyr Cys Thr Ser Asn Asp Asp Gln Val Gly Ile Trp Ser Gly Pro
    1115            1120                1125

Ala Pro Gln Cys Ile Ile Pro Asn Lys Cys Thr Pro Pro Asn Val
    1130            1135                1140

Glu Asn Gly Ile Leu Val Ser Asp Asn Arg Ser Leu Phe Ser Leu
    1145            1150                1155

Asn Glu Val Val Glu Phe Arg Cys Gln Pro Gly Phe Val Met Lys
    1160            1165                1170

Gly Pro Arg Arg Val Lys Cys Gln Ala Leu Asn Lys Trp Glu Pro
    1175            1180                1185

Glu Leu Pro Ser Cys Ser Arg Val Cys Gln Pro Pro Pro Glu Ile
    1190            1195                1200

Leu His Gly Glu His Thr Pro Ser His Gln Asp Asn Phe Ser Pro
    1205            1210                1215

Gly Gln Glu Val Phe Tyr Ser Cys Glu Pro Gly Tyr Asp Leu Arg
    1220            1225                1230

Gly Ala Ala Ser Leu His Cys Thr Pro Gln Gly Asp Trp Ser Pro
    1235            1240                1245

Glu Ala Pro Arg Cys Ala Val Lys Ser Cys Asp Asp Phe Leu Gly
    1250            1255                1260

Gln Leu Pro His Gly Arg Val Leu Phe Pro Leu Asn Leu Gln Leu
    1265            1270                1275

Gly Ala Lys Val Ser Phe Val Cys Asp Glu Gly Phe Arg Leu Lys
    1280            1285                1290

Gly Ser Ser Val Ser His Cys Val Leu Val Gly Met Arg Ser Leu
    1295            1300                1305

Trp Asn Asn Ser Val Pro Val Cys Glu His Ile Phe Cys Pro Asn
    1310            1315                1320

Pro Pro Ala Ile Leu Asn Gly Arg His Thr Gly Thr Pro Ser Gly
    1325            1330                1335

Asp Ile Pro Tyr Gly Lys Glu Ile Ser Tyr Thr Cys Asp Pro His
    1340            1345                1350

Pro Asp Arg Gly Met Thr Phe Asn Leu Ile Gly Glu Ser Thr Ile
    1355            1360                1365

Arg Cys Thr Ser Asp Pro His Gly Asn Gly Val Trp Ser Ser Pro
    1370            1375                1380

Ala Pro Arg Cys Glu Leu Ser Val Arg Ala Gly His Cys Lys Thr
    1385            1390                1395

Pro Glu Gln Phe Pro Phe Ala Ser Pro Thr Ile Pro Ile Asn Asp
    1400            1405                1410

Phe Glu Phe Pro Val Gly Thr Ser Leu Asn Tyr Glu Cys Arg Pro
    1415            1420                1425

Gly Tyr Phe Gly Lys Met Phe Ser Ile Ser Cys Leu Glu Asn Leu
    1430            1435                1440

Val Trp Ser Ser Val Glu Asp Asn Cys Arg Arg Lys Ser Cys Gly
```

-continued

```
            1445                1450                1455
Pro Pro Pro Glu Pro Phe Asn Gly Met Val His Ile Asn Thr Asp
        1460                1465                1470
Thr Gln Phe Gly Ser Thr Val Asn Tyr Ser Cys Asn Glu Gly Phe
        1475                1480                1485
Arg Leu Ile Gly Ser Pro Ser Thr Thr Cys Leu Val Ser Gly Asn
        1490                1495                1500
Asn Val Thr Trp Asp Lys Lys Ala Pro Ile Cys Glu Ile Ile Ser
        1505                1510                1515
Cys Glu Pro Pro Pro Thr Ile Ser Asn Gly Asp Phe Tyr Ser Asn
        1520                1525                1530
Asn Arg Thr Ser Phe His Asn Gly Thr Val Val Thr Tyr Gln Cys
        1535                1540                1545
His Thr Gly Pro Asp Gly Glu Gln Leu Phe Glu Leu Val Gly Glu
        1550                1555                1560
Arg Ser Ile Tyr Cys Thr Ser Lys Asp Asp Gln Val Gly Val Trp
        1565                1570                1575
Ser Ser Pro Pro Pro Arg Cys Ile Ser Thr Asn Lys Cys Thr Ala
        1580                1585                1590
Pro Glu Val Glu Asn Ala Ile Arg Val Pro Gly Asn Arg Ser Phe
        1595                1600                1605
Phe Ser Leu Thr Glu Ile Ile Arg Phe Arg Cys Gln Pro Gly Phe
        1610                1615                1620
Val Met Val Gly Ser His Thr Val Gln Cys Gln Thr Asn Gly Arg
        1625                1630                1635
Trp Gly Pro Lys Leu Pro His Cys Ser Arg Val Cys Gln Pro Pro
        1640                1645                1650
Pro Glu Ile Leu His Gly Glu His Thr Leu Ser His Gln Asp Asn
        1655                1660                1665
Phe Ser Pro Gly Gln Glu Val Phe Tyr Ser Cys Glu Pro Ser Tyr
        1670                1675                1680
Asp Leu Arg Gly Ala Ala Ser Leu His Cys Thr Pro Gln Gly Asp
        1685                1690                1695
Trp Ser Pro Glu Ala Pro Arg Cys Thr Val Lys Ser Cys Asp Asp
        1700                1705                1710
Phe Leu Gly Gln Leu Pro His Gly Arg Val Leu Leu Pro Leu Asn
        1715                1720                1725
Leu Gln Leu Gly Ala Lys Val Ser Phe Val Cys Asp Glu Gly Phe
        1730                1735                1740
Arg Leu Lys Gly Arg Ser Ala Ser His Cys Val Leu Ala Gly Met
        1745                1750                1755
Lys Ala Leu Trp Asn Ser Ser Val Pro Val Cys Glu Gln Ile Phe
        1760                1765                1770
Cys Pro Asn Pro Pro Ala Ile Leu Asn Gly Arg His Thr Gly Thr
        1775                1780                1785
Pro Phe Gly Asp Ile Pro Tyr Gly Lys Glu Ile Ser Tyr Ala Cys
        1790                1795                1800
Asp Thr His Pro Asp Arg Gly Met Thr Phe Asn Leu Ile Gly Glu
        1805                1810                1815
Ser Ser Ile Arg Cys Thr Ser Asp Pro Gln Gly Asn Gly Val Trp
        1820                1825                1830
Ser Ser Pro Ala Pro Arg Cys Glu Leu Ser Val Pro Ala Ala Cys
        1835                1840                1845
```

| | | | | | | | | | |
|---|---|---|---|---|---|---|---|---|---|
| Pro | His | Pro | Pro | Lys | Ile | Gln | Asn | Gly | His | Tyr | Ile | Gly | Gly | His |
| | 1850 | | | | 1855 | | | | 1860 |

Val Ser Leu Tyr Leu Pro Gly Met Thr Ile Ser Tyr Ile Cys Asp
    1865                   1870                  1875

Pro Gly Tyr Leu Leu Val Gly Lys Gly Phe Ile Phe Cys Thr Asp
    1880                   1885                   1890

Gln Gly Ile Trp Ser Gln Leu Asp His Tyr Cys Lys Glu Val Asn
    1895                   1900                 1905

Cys Ser Phe Pro Leu Phe Met Asn Gly Ile Ser Lys Glu Leu Glu
    1910                   1915                1920

Met Lys Lys Val Tyr His Tyr Gly Asp Tyr Val Thr Leu Lys Cys
    1925                   1930                1935

Glu Asp Gly Tyr Thr Leu Glu Gly Ser Pro Trp Ser Gln Cys Gln
    1940                   1945                1950

Ala Asp Asp Arg Trp Asp Pro Pro Leu Ala Lys Cys Thr Ser Arg
    1955                   1960                1965

Thr His Asp Ala Leu Ile Val Gly Thr Leu Ser Gly Thr Ile Phe
    1970                   1975                1980

Phe Ile Leu Leu Ile Ile Phe Leu Ser Trp Ile Ile Leu Lys His
    1985                   1990                1995

Arg Lys Gly Asn Asn Ala His Glu Asn Pro Lys Glu Val Ala Ile
    2000                   2005                2010

His Leu His Ser Gln Gly Gly Ser Ser Val His Pro Arg Thr Leu
    2015                   2020                2025

Gln Thr Asn Glu Glu Asn Ser Arg Val Leu Pro
    2030                   2035

```
<210> SEQ ID NO 3
<211> LENGTH: 4233
<212> TYPE: DNA
<213> ORGANISM: Homo sapiens

<400> SEQUENCE: 3
```

| | |
|---|---|
| ggatatctag gaaagatctc actgagaagg tatcttcgag taaagactag aatgaaatga | 60 |
| gggagctggc cactggggct attcaggaga aaacaatct ggacagagca acaagaccc | 120 |
| tccgagggca aaggaccca gtcagagtgc aaagaatact agagcagcaa aggccattgt | 180 |
| ggccagaggg agaaaagaag gagaaaaggg tcaaagatga actcagagaa gttaaaggaa | 240 |
| agcagatcac attggactga atggatcata gttatgacat tgccttctac tttgaatgag | 300 |
| ataggaaatt attggagggt ttggagcaga aggcagtgat ttcttttttc ctgacaaaca | 360 |
| tgtaaacagg atcactgcaa gatactagac caacacac tcatctacag aggagttgag | 420 |
| tttttgtgtt gctgagaagt gtttattaat aaaaatatat ttgggaaatt tatgagggca | 480 |
| gacaagaata agcatgaaaa gaatcatgaa tctaactgta aaataaatga aacaatacac | 540 |
| gtgcaagaag aaaacatgga tgaattattg tgtaacctgg agaatggttt ttaaaaccat | 600 |
| ggctcctaat ccagatgcaa taaagaaaa gatttatcaa cttgactgca ttaaaacaga | 660 |
| caatgcttac aaggcaaaac gatgccataa acaaagtcaa aagacaactg acaaactggg | 720 |
| aggaaacatt tgcaaaacac atccagaata acaatcctaa tatatataaa taagtctcaa | 780 |
| acattgagag aggaaaaggc aaatatacat gataaaaata tatttttataa atgttcagcg | 840 |
| ttactcatag ggaatgcaaa ttaaagctac actgagataa aatgtctcat ttattagact | 900 |
| gactaaaatt taaaaccatg atgacagcac attagattaa tgaggtgctc tcacacagtt | 960 |

```
ttgtaggaat atatgtggta caactcttat taaggaaatt tggcaatatc taacaaacct    1020
acatatgtgt ttaccatttg acccagcaat cccacttcta ggaatttgaa ctgaagacat    1080
gcttctaaca gcagaaaaat aaatattcac aaagttactc tttagagcat taaaaacaac    1140
caaactgtcc atacataggg agatggttga ataaactatg gcatatccac acagtgaagt    1200
attgcatgca actgtaaaaa tgaatgagga atatttgaat ttgtaggaaa tagtggattc    1260
cagcatattt gttaagttaa aaagaaatg tgcaaaagaa tacctatagc atgcttttaa    1320
aatgtaataa aaaaggagaa ctaagaagac aaatgtgtag cagctcattt gagcaaaact    1380
aaggacaaac cagaaactac tgaaattgag tacctatggt ggagaggata gaggtgatgg    1440
agagaagtga catttcccctt ttattgtgtc tttttatatc aatctgacat ttgggactac    1500
gttaatgttt tatttaagca aaaaaaaatc aaaaagattg aggggaaact aaaatagaat    1560
acaaagagaa acaaattaac agtattttga atgaataaca atcacactga agagggggaa    1620
taatctgagt aactttggaa cacaacaatg ctgttttat attttcgggc tataaacaaa    1680
ataaaacttt aaaaacgagt agatttgatt tccatcatag tatagaaata gcaattttaa    1740
acttctttct gtgtattcta ggattaagca aataagtaaa tatattgtgg atctaggtgt    1800
ctcactgttg aagaagggag ttacacatgc agaaagaggg aaggacagaa tgaactctat    1860
gctaacggac tgaaattgga agaatcactg tgaattcatg acatatataa atatagatat    1920
gggaatggat atacatatat atatataata catatccttg ctctgtctgc tgagagggtg    1980
cggaaacaat gatactccaa taaaaatgaa cacacttagc atccaattct ggcatctaaa    2040
tgccattctc tgccagaaag aaccagcatt ccttggagaa acagcaaatt ccagtgtcag    2100
gtctagaggt gagtctggag cattttttt tgtgtgtgtg ccagaaagta aggaagtgct    2160
caaagaacaa taagaacaag tcaaaatgac ataggaacta ttttgagggc tcccactggc    2220
ccgatcaggg agaatttaag catcaaaata aataatggta gccatgaatt atgacccatt    2280
gagtaaataa ataaaattca tattgatata gtttatgctg atatagataa atgaataaat    2340
aaatagagaa gggaaaactt ttatttacag taaaatgcca acagatgaat atagaagtaa    2400
ttattaaatt aggaaaaaac ccctttgac aaccatcata gtaaaaattg attcaagaaa     2460
ggatcatcaa tagacgctaa aatttgtggg taaaaatttg atgaaaaaat gaggaattta    2520
catagtttta aagtatctcc ctataaaata cttattaatt acaaagggaa aaatactgag    2580
tctacactaa gaaacatggc aggcaccatc ttaactaagt gatcaaagtt accaccacca    2640
gtaataggac aaatagacaa catatgcctc cccgtaagga taagacatcc tttctggtat    2700
tcctgtcaaa taattagatt caataacctg aatctatcat gaagaaatga tagacaaatc    2760
caaattgtgg ggtgtgatcc tgtctcctga cattaccatc cacgtatact gccctcctac    2820
actgaaaagg gctgatctgt acaatcaatt ggatattctg gagttaacat attgtgattt    2880
ctgaggacag gtcacaaagg acattatggc ttcttcttc ttgttctcag agacgctagc     2940
tggcatgtca cgaggacact caacacacaa gcagcgagcc ctatggcaaa atccacgtgg    3000
tgaagaatga agcttccagc caaaggctgg taagtgagcc atcttagatg tggattcgcc    3060
tatcccagtt aaccctccag atgactgcac ctccagctgg tgtcttaact gcaatctcct    3120
gagcgatccc aagccagaac cacctgaccg acccacagaa actgtgagat cataaatgtt    3180
tattcttgct ttcaccact accttcaggg taatttgtta ttataataga taacggactt     3240
aaaagtcatt ctccaaaaat aattgtggtg tattcgtcaa aaatgtaaag gtcatgcaat    3300
```

```
accaaaaatg ctgaggacat ttttccagaa taaagaactg ggggtggggg gaaggcataa    3360
tgatcaaaca caatacatga tcctgaaatg attctggacc aggaaaaaca aaggttggtt    3420
tctattgttg ttattgtttt taccataaca caggttattg agatgattgt caaaatttaa    3480
atacagatgg tagcttatag tcttgtgtca atgttaagtt cttattttg atcattgcac     3540 tctagttatg gaacagaaag tccttagtga accatttaga ataggaataa atgctagatg    3600
gttccaaagt aataattata taattataat tatataatca catatatgta catatatgtc    3660
tatagagaaa gaatagagaa tggtaaagaa aatacagcaa atgttaaca tgcagagaat     3720 ctgggtgaca agtatatggg aattctctgc agtactcttg aaacttttct gtagagatta    3780
cttcaaaata aagaacagag cagaagtggc tgctgttcct aaattcccta agtaaactta    3840
cactgctttt tcaaactggg agatgaatcc actaataggt tttgaaatga gtttggtgga    3900
tttctaataa gaataggata gcctagccta gtctagcata acacagcatg gcacagagga    3960
cgaacattgt agattactaa gggtgagtac taacttgtga agttttgtt taagttctag     4020 taagagaaac aagtgagtgt agtgggttgc gtggtcaaaa aagtggggaa gccaccgcaa    4080
cgaggggtga gtctgagcca aagagtggct cagagctccc cgcccacctc gtgccgggcc    4140
gtccctcccg cttgtcccac cctcaccggc gccgcgtcag cccccaggcc gcctgcaggt    4200
gtgcgctcag aactagcacg tgtgccggac act                                  4233

<210> SEQ ID NO 4
<211> LENGTH: 135
<212> TYPE: DNA
<213> ORGANISM: Homo sapiens

<400> SEQUENCE: 4
agctcgcttt cttgctgtcc aatttctatt aaaggttcct tgttccta agtccaacta      60 ctaaactggg ggatattatg aagggccttg agcatctgga ttctgcctaa taaaaaacat    120
ttattttcat tgcaa                                                     135

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
tgagcctact caaccttaac agt                                             23

<210> SEQ ID NO 6
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 6
tctgtctggt ggcatagttc acttgc                                          26

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 7
```
tggcctgttt gaaggaattg ttg                                           23

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
gcatgcaaac aaaccattgg aa                                            22

<210> SEQ ID NO 9
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 9
aaaggaaatg agaagacagt aaaacctgca                                    30

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 10
cccgtctaag aaacactgag gta                                           23

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
gcagtggaag gcgcagatg                                                19

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 12
agcgggtgcc gcacgaaatt c                                             21

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
cagccgaggc tgtgaataca c                                             21

<210> SEQ ID NO 14
<211> LENGTH: 21
<212> TYPE: DNA

<213> ORGANISM: Artificial Sequence
<220> FEATURE:
<223> OTHER INFORMATION: Synthetic Oligonucleotide

<400> SEQUENCE: 14
tgggcaaagg acatacagct a                                             21

<210> SEQ ID NO 15
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 15
tcaccaagaa agaagggcaa ataggtgg                                      28

<210> SEQ ID NO 16
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 16
ggccaattcc caatcactta gtttc                                         25

<210> SEQ ID NO 17
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 17
catcagcact ggcctactac a                                             21

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 18
aagctgaggc ctacagacac tccc                                          24

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
aggcagccac ccaacagtta c                                             21

<210> SEQ ID NO 20
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 20
tgaccagagg gacatagaac tcc                                           23

<210> SEQ ID NO 21
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 21
tcacccaagc agcaagagac tattgta                                27

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 22
tcccaacatg gtggctagtt t                                      21

<210> SEQ ID NO 23
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 23
gccaggccta ccaaccta                                          18

<210> SEQ ID NO 24
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 24
tgatgagttt gagtttccca ttgggaca                               28

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
cagggcggca ttcatagttc ag                                     22

<210> SEQ ID NO 26
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 26
tctcgtgcac atgatgctc                                         19

<210> SEQ ID NO 27
<211> LENGTH: 29
<212> TYPE: DNA
<213> ORGANISM: Artificial Sequence
<220> FEATURE:

<223> OTHER INFORMATION: Synthetic Oligonucleotide

<400> SEQUENCE: 27
tcatagttgg cactttatct ggtacgatc                                29

<210> SEQ ID NO 28
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 28
acgctgctgc ctccttgag                                           19

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
agctgggtgg gttagtggag aa                                       22

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 30
agtgctagct gttggtccag ca                                       22

<210> SEQ ID NO 31
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 31
tgccgcttgc ctttgtaag                                           19

<210> SEQ ID NO 32
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 32
tctgcgccat gtttgacttt g                                        21

<210> SEQ ID NO 33
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 33
tggcttctac taggcacacg acgg                                     24

```
<210> SEQ ID NO 34
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 34
ggtgctgcat acttcctctc ta                                              22

<210> SEQ ID NO 35
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 35
ggaagggaag agcaacaaca c                                               21

<210> SEQ ID NO 36
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 36
tcttggacac cttgaagacg gagc                                            24

<210> SEQ ID NO 37
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 37
ccagcgtcag gaggtctg                                                   18

<210> SEQ ID NO 38
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 38
ggcctgtcag ccatcttatg c                                               21

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 39
tttcctggac ctctgctggg atcg                                            24

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 40
tggtgctgct ggtggtag                                                    18

<210> SEQ ID NO 41
<211> LENGTH: 159
<212> TYPE: DNA
<213> ORGANISM: Homo sapiens

<400> SEQUENCE: 41
cttatggaat atagttctgt acctgattgt tttcataatc cctgtgttga tgtgtaatgc      60
cacagacatg ctcttgatag taacaggaaa gaaaatcaga cacagctaaa cataaaggtc     120
agttggctgg caggtgctta gcaggtgtaa atagaggcc                            159
```